United States Patent [19]

Fischer et al.

[11] Patent Number: 4,889,848

[45] Date of Patent: Dec. 26, 1989

[54] TRICYCLIC PYRIDINE DERIVATIVES

[75] Inventors: Ulf Fischer, Frenkendorf; Fernand Schneider, Basel; Ulrich Widmer, Rheinfelden, all of Switzerland

[73] Assignee: Hoffmann-La Roche Inc., Nutley, N.J.

[21] Appl. No.: 141,022

[22] Filed: Jan. 5, 1988

Related U.S. Application Data

[62] Division of Ser. No. 793,511, Oct. 31, 1985, Pat. No. 4,735,940.

[51] Int. Cl.$^4$ .................. A61K 31/435; C07D 221/04
[52] U.S. Cl. ................. 514/212; 514/222.2; 514/233.2; 514/253; 514/294; 540/597; 544/54; 544/58.4; 544/126; 544/361; 546/95
[58] Field of Search ................. 540/597; 544/54, 58.4, 544/126, 361; 546/95; 514/212, 222.2, 233.2, 253, 294

[56] References Cited

U.S. PATENT DOCUMENTS 4,236,010 11/1980 Imhof et al. .................. 546/138

FOREIGN PATENT DOCUMENTS 0157346 10/1985 European Pat. Off. .

OTHER PUBLICATIONS

Monatsh. Chem. 98, 2148–2156, (1967).
Chem. Pharm. Bull., 2294, 744–751, (1974).
Monatsh. Chem., 100, 1726–1734, (1969).
Chem. Pharm. Bull., 21, (5), 921–925, (1973).
J. Heterocyclic Chem., 18, 1451–1456, (1981).
Chemical Abstracts, 87, 84933n, (1977).
Chemical Abstracts, 89, 107293n, (1978).
Pharmazie 23, 301–303, (1968).
Chemical Abstracts, 89, 197, 445r, (1978).
Chemical Abstracts, 92, 215321r, (1980).
J. Org. Chem., 50, 1666–1676, (1985).
J. Org. Chem., 50, 1677–1681, (1985).
Can. J. Chem., 63, 882–886, (1985).
J. Org. Chem., 37(11), 1823–1825, (1972).

*Primary Examiner*—Mary C. Lee
*Assistant Examiner*—Mary Sue Howard
*Attorney, Agent, or Firm*—George M. Gould; Bernard S. Leon; William G. Isgro

[57] ABSTRACT

Compounds of the formula

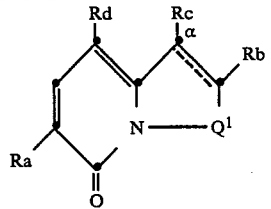

I wherein $Q^1$ and the nitrogen atom taken together are a group of the formula >N—CH$_2$CH$_2$— (a), >N—CH$_2$CH$_2$CH$_2$— (b), >N—CH=CH— (c), >N—CH$_2$—CH=CH— (d), >N—CH$_2$—S(O)$_p$— (e), >N—CH$_2$CH$_2$—S(O)$_p$— (f) or >N—CH=CH—S-(O)$_p$— (g), p is the integer 0, 1 or 2, Ra is a phenyl, pyridyl or thienyl group which is optionally substituted by halogen, trifluoromethyl, nitro, lower alkyl or lower alkoxy, Rb and Rc each, independently, are hydrogen, halogen, trifluoromethyl, lower alkyl, lower alkoxy or nitro and the dotted line signifies an optional bond, or Rb and Rc together with the carbon atom denoted by α are a group of the formula >Cα—S—CH=CH— (h), >Cα—CH=CH—S— (i) or >Cα—CH=CH—CH= CH— (j) which is optionally substituted by halogen, trifluoromethyl, lower alkyl, lower alkoxy, nitro, amino or mono- or di(lower alkyl)amino, and the dotted line signifies an additional bond, Rd is the group of the formula —(A$^1$)$_m$—(CO)$_n$—(Q$^2$A$^2$)$_q$—R$^1$, m, m and q each, independently, are the integer 0 or 1, A$^1$ is lower alkylene, A$^2$ is lower alkylene, a direct bond or the group —CO—, Q$^2$ is an oxygen atom or the group —NR$^2$—, R$^1$ is hydrogen, hydroxy, cyano, nitro, halogen, lower alkoxy, lower alkyl, lower alkoxycarbonyl, aryl, a group of the formula —NR$^3$R$^4$ or a 5-membered, saturated, partially unsaturated or aromatic heterocycle which is attached via a carbon atom and which is optionally substituted by one or two lower alkyl groups and optionally substituted by a (C$_{3-6}$)-cycloalkyl, hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or alkylenedioxy group, R$^2$ is hydrogen, lower alkyl or aryl, R$^3$ and R$^4$ each, independently, are hydrogen, lower alkyl, lower alkoxyalkyl, lower dialkoxyalkyl, lower alkylenedioxyalkyl, lower cyanoalkyl, lower haloalkyl, lower hydroxyalkyl, lower dihydroxyalkyl, lower alkanoyl, lower alkoxycarbonyl or a (C$_{3-7}$)-cycloalkyl group which is optionally substituted by hydroxy, lower alkoxy, lower alkanoyloxy, lower hydroxyalkyl, lower alkoxyalkyl, lower alkanoyloxyalkyl, oxo, carbamoyl, mono- or di(lower alkyl)carbamoyl or by lower alkylenedioxy or together with the nitrogen atom is a 3- to 7-membered, saturated N-heterocycle which is optionally substituted by one or two lower alkyl groups and optionally substituted by one or two hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or lower alkylenedioxy (Abstract continued on next page.)

groups and which can contain as a ring member an oxygen or sulfur atom or the group $>N-R^5$, and $R^5$ is hydrogen, lower alkyl, lower hydroxyalkyl, lower alkoxyalkyl, lower alkanoyloxyalkyl, lower alkanoyl, lower alkoxycarbonyl, carbamoyl or mono- or di(lower alkyl) carbamoyl, with the proviso that n is 0 when q is 1 and $A^2$ is the group —CO—, that $R^1$ is other than cyano, nitro, halogen or lower alkoxycarbonyl when q is 0 and n is 1 or when q is 1 and $A^2$ is —CO—, and that $R^1$ is other than hydroxy, cyano, nitro, halogen, lower alkoxycarbonyl, lower alkoxy and —$NR^3R^4$ when q is 1 and $A^2$ is a direct bond, or a pharmaceutically acceptable acid addition salt of a compound of formula I which has one or more basic substituents, are described.

The compounds of formula I possess pronounced muscle relaxant, sedative-hypnotic, anticonvulsive and anxiolytic properties and have low toxicity.

34 Claims, No Drawings

TRICYCLIC PYRIDINE DERIVATIVES

This is a division, of application Ser. No. 793,511 filed Oct. 31, 1985, now U.S. Pat. No. 4,735,940.

BRIEF SUMMARY OF THE INVENTION

The invention relates to compounds of the formula

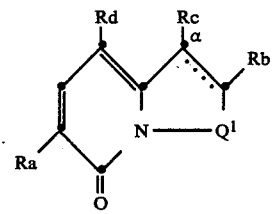

wherein $Q^1$ and the nitrogen atom taken together are a group of the formula >N—CH$_2$CH$_2$— (a), >N—CH$_2$CH$_2$CH$_2$— (b), >N—CH=CH— (c), >N—CH$_2$—CH=CH— (d), >N—CH$_2$—S(O)$_p$— (e), >N—CH$_2$CH$_2$—S(O)$_p$— (f) or >N—CH=CH—S(O)$_p$— (g), p is the integer 0, 1 or 2, Ra is a phenyl, pyridyl or thienyl group which is optionally substituted by halogen, trifluoromethyl, nitro, lower alkyl or lower alkoxy, Rb and Rc each, independently, are hydrogen, halogen, trifluoromethyl, lower alkyl, lower alkoxy or nitro and the dotted line signifies an optional bond, or Rb and Rc together with the carbon atom denoted by $\alpha$ are a group of the formula >C$_\alpha$—S—CH=CH— (h), >C$_\alpha$—CH=CH—S— (i) or >C$_\alpha$—CH=CH—CH=CH— (j) which is optionally substituted by halogen, trifluoromethyl, lower alkyl, lower alkoxy, nitro, amino or mono- or di(lower alkyl)amino, and the dotted line signifies an additional bond, Rd is the group of the formula —(A$^1$)$_m$—(CO)$_n$—(Q$^2$A$^2$)$_q$—R$^1$, m, n and q each, independently, are the integer 0 or 1, A$^1$ is lower alkylene, A$^2$ is lower alkylene, a direct bond or the group —CO—, Q$^2$ is an oxygen atom or the group —NR$^2$—, R$^1$ is hydrogen, hydroxy, cyano, nitro, halogen, lower alkoxy, lower alkyl, lower alkoxycarbonyl, aryl, a group of the formula —NR$^3$R$^4$ or a 5-membered, saturated, partially unsaturated or aromatic heterocycle which is attached via a carbon atom and which is optionally substituted by one or two lower alkyl groups and optionally substituted by a (C$_{3-6}$)-cycloalkyl, hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or alkylenedioxy group, R$^2$ is hydrogen, lower alkyl or aryl, R$^3$ and R$^4$ each, independently, are hydrogen, lower alkyl, lower alkoxyalkyl, lower dialkoxyalkyl, lower alkylenedioxyalkyl, lower cyanoalkyl, lower haloalkyl, lower hydroxyalkyl, lower dihydroxyalkyl, lower alkanoyl, lower alkoxycarbonyl or a (C$_{3-7}$)-cycloalkyl group which is optionally substituted by hydroxy, lower alkoxy, lower alkanoyloxy, lower hydroxyalkyl, lower alkoxyalkyl, lower alkanoyloxyalkyl, oxo, carbamoyl, mono- or di(lower alkyl)carbamoyl or by lower alkylenedioxy or together with the nitrogen atom is a 3- to 7-membered, saturated N-heterocycle which is optionally substituted by one or two lower alkyl groups and optionally substituted by one or two hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or lower alkylenedioxy groups and which can contain as a ring member an oxygen or sulfur atom or the group >N—R$^5$, and R$^5$ is hydrogen, lower alkyl, lower hydroxyalkyl, lower alkoxyalkyl, lower alkanoyloxyalkyl, lower alkanoyl, lower alkoxycarbonyl, carbamoyl or mono- or di(lower alkyl)carbamoyl, with the proviso that n is 0 when q is 1 and A$^2$ is the group —CO—, that R$^1$ is other than cyano, nitro, halogen or lower alkoxycarbonyl when q is 0 and n is 1 or when q is 1 and A$^2$ is —CO—, and that R$^1$ is other than hydroxy, cyano, nitro, halogen, lower alkoxycarbonyl, lower alkoxy and —NR$^3$R$^4$ when q is 1 and A$^2$ is a direct bond, and pharmaceutically acceptable acid addition salts of the compounds of formula I which have one or more basic substituents.

The bi- and tricyclic pyridone derivatives of formula I have muscle relaxant, sedative-hypnotic, anxiolytic and/or anticonvulsive activity and accordingly are useful in the control or prevention of muscle tensions, stress conditions, insomnia, anxiety states and/or convulsions.

DETAILED DESCRIPTION OF THE INVENTION

The invention relates to compounds of the formula

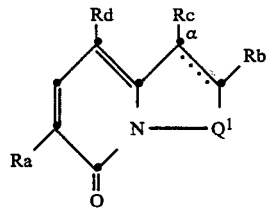

wherein $Q^1$ and the nitrogen atom taken together are a group of the formula >N—CH$_2$CH$_2$— (a), >N—CH$_2$CH$_2$CH$_2$— (b), >N—CH=CH— (c), >N—CH$_2$—CH=CH— (d), >N—CH$_2$—S(O)$_p$— (e), >N—CH$_2$CH$_2$—S(O)$_p$— (f) or >N—CH=CH—S(O)$_p$— (g), p is the integer 0, 1 or 2, Ra is a phenyl, pyridyl or thienyl group which is optionally substituted by halogen, trifluoromethyl, nitro, lower alkyl or lower alkoxy, Rb and Rc each, independently, are hydrogen, halogen, trifluoromethyl, lower alkyl, lower alkoxy or nitro and the dotted line signifies an optional bond, or Rb and Rc together with the carbon atom denoted by $\alpha$ are a group of the formula >C$_\alpha$—S—CH=CH— (h), >C$_\alpha$—CH=CH—S— (i) or >C$_\alpha$—CH=CH—CH=CH— (j) which is optionally substituted by halogen, trifluoromethyl, lower alkyl, lower alkoxy, nitro, amino or mono- or di(lower alkyl)amino, and the dotted line signifies an additional bond, Rd is the group of the formula —(A$^1$)$_m$—(CO)$_n$—(Q$^2$A$^2$)$_q$—R$^1$, m, n and q each, independently, are the integer 0 or 1, A$^1$ is lower alkylene, A$^2$ is lower alkylene, a direct bond or the group —CO—, Q$^2$ is an oxygen atom or the group —NR$^2$—, R$^1$ is hydrogen, hydroxy, cyano, nitro, halogen, lower alkoxy, lower alkyl, lower alkoxycarbonyl, aryl, a group of the formula —NR$^3$R$^4$ or a 5-membered, saturated, partially unsaturated or aromatic heterocycle which is attached via a carbon atom and which is optionally substituted by one or two lower alkyl groups and optionally substituted by a (C$_{3-6}$)-cycloalkyl, hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or alkylenedioxy group, $R^2$ is hydrogen, lower alkyl or aryl, $R^3$ and $R^4$ each, independently, are hydrogen, lower alkyl, lower alkoxyalkyl, lower dialkoxyalkyl, lower alkylenedioxyalkyl, lower cyanoalkyl, lower haloalkyl, lower hydroxyalkyl, lower dihydroxyalkyl, lower alkanoyl, lower alkoxycarbonyl or a $(C_{3-7})$cycloalkyl group which is optionally substituted by hydroxy, lower alkoxy, lower alkanoyloxy, lower hydroxyalkyl, lower alkoxyalkyl, lower alkanoyloxyalkyl, oxo, carbamoyl, mono- or di(lower alkyl)carbamoyl or by lower alkylenedioxy or together with the nitrogen atom is a 3- to 7-membered, saturated N-heterocycle which is optionally substituted by one or two lower alkyl groups and optionally substituted by one or two hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or lower alkylenedioxy groups and which can contain as a ring member an oxygen or sulfur atom or the group $>N-R^5$, and $R^5$ is hydrogen, lower alkyl, lower hydroxyalkyl, lower alkoxyalkyl, lower alkanoyloxyalkyl, lower alkanoyl, lower alkoxycarbonyl, carbamoyl or mono- or di(lower alkyl)carbamoyl, with the proviso that n is 0 when q is 1 and $A^2$ is the group —CO—, provided that $R^1$ is other than cyano, nitro, halogen or lower alkoxycarbonyl when q is 0 and n is 1 or when q is 1 and $A^2$ is —CO—, and that $R^1$ is other than hydroxy, cyano, nitro, halogen, lower alkoxycarbonyl, lower alkoxy and —$NR^3R^4$ when q is 1 and $A^2$ is a direct bond,
and pharmaceutically acceptable acid addition salts of the compounds of formula I which have one or more basic substituents.

The bi- and tricyclic pyridone derivatives of formula I have valuable pharmacological properties and can be used for the control or prevention of illnesses. In particular, they have muscle relaxant, sedative-hypnotic, anxiolytic and/or anticonvulsive activity and accordingly are useful in the control or prevention of muscle tensions, stress conditions, insomnia, anxiety states and/or convulsions.

The invention comprises the compounds of formula I and their salts per se and as therapeutically active substances, a process and intermediates for their preparation, the preparation of the intermediates and their use for the preparation of therapeutically active substances, medicaments based on these active substances and their preparations, the use of the active substances in the control or prevention of illnesses, as well as their use for the preparation of medicaments having muscle relaxant, sedative-hypnotic, anxiolytic and/or anticonvulsive activity.

As used herein, the term "lower" denotes residues and compounds having a maximum of seven, preferably a maximum of four, carbon atoms. The term "alkyl", alone or in combinations such as alkanoyl, alkanoyloxy and alkoxyalkyl, denotes straight-chain or branched, saturated hydrocarbon residues such as methyl, ethyl, isopropyl and t-butyl. The term "cycloalkyl" denotes cyclic, saturated hydrocarbon residues such as cyclohexyl. The term "alkoxy" denotes alkyl groups attached via an oxygen atom, such as methoxy and ethoxy. The term "hydroxyalkyl" denotes alkyl groups substituted by hydroxy, such as 2-hydroxyethyl. The terms "alkanoyl" and "alkanoyloxy" denote fatty acid residues such as acetyl and acetoxy, respectively. The term "alkylene" denotes straight-chain or branched, saturated hydrocarbon residues having two free valencies, such as methylene, 1,2-ethylene and 1,3-propylene. The term "halogen" denotes the four forms fluorine, chlorine, bromine and iodine.

The term "aryl" preferably denotes phenyl groups which are optionally substituted by halogen, trifluoromethyl, lower alkyl, lower alkoxy, nitro, amino or mono- or di(lower alkyl)amino.

The 5-membered, saturated, partially unsaturated or aromatic heterocycles which are attached via a carbon atom preferably contain as the hetero ring member(s) an oxygen or sulfur atom or an imino or lower alkylimino group and optionally one or two nitrogen atoms, with the carbon atom via which the heterocycle is attached being preferably situated adjacent to one hetero atom or between two hetero atoms. Examples of such heterocycles, which can be substituted as indicated earlier, are, 2-oxazolin-2-yl, 3-methyl-1,2,4-oxadiazol-5-yl, 2-thiazolin-2-yl, 2-tetrahydrofuryl, 2-thiazolyl and the like.

The term "3- to 7-membered, saturated N-heterocycle which can contain as a ring member an oxygen or sulfur atom or the group $>N-R^5$" as a possible value for —$NR^3R^4$ denotes on the one hand heterocycles having only one hetero atom, namely the nitrogen atom via which they are attached, and on the other hand heterocycles having two hetero atoms, namely the aforementioned nitrogen atom and an oxygen or sulfur atom or a second nitrogen atom. Examples of such heterocycles, which can be substituted as indicated earlier, are, 2-(lower alkoxyalkyl)-1-azetidinyl, 3-(lower alkoxy)-1-azetidinyl, 3-hydroxy-1-azetidinyl, 2-(lower hydroxyalkyl)-1-azetidinyl, 2-(lower alkanoyloxyalkyl)-1-pyrrolidinyl, 3-oxo-1-pyrrolidinyl, 2-(lower alkoxycarbonyl)-1-pyrrolidinyl, 3-(lower alkoxy)-1-pyrrolidinyl, 3-hydroxy-1-pyrrolidinyl, 2-(lower alkoxyalkyl)-1-pyrrolidinyl, 2-(lower hydroxyalkyl)-1-pyrrolidinyl, 2-(lower hydroxyalkyl)-4-hydroxy-1-pyrrolidinyl, 2-(lower alkoxyalkyl)-4-(lower alkoxy)-1-pyrrolidinyl, 4-morpholinyl, 2,6-di(lower alkyl)-4-morpholinyl, 4-thiomorpholinyl, 1-piperazinyl, 1-(lower alkyl)-4-piperazinyl, 1-(lower alkoxyalkyl)-4-piperazinyl, 1-(lower alkanoyl)-4-piperazinyl, 4-(lower hydroxyalkyl)-1-piperidinyl, 4-oxo-1-piperidinyl, 4-(lower alkoxy)-1-piperidinyl, 4-(lower alkoxycarbonyl)-1-piperidinyl, 4-hydroxy-1-piperidinyl, 4-(lower alkylcarbamoyl)-1-piperidinyl, 4-(lower alkanoyloxy)-1-piperidinyl, 2-(lower alkoxyalkyl)-1-piperidinyl, 2-(lower hydroxyalkyl)-1-piperidinyl, 3-(lower alkoxy)-1-piperidinyl, 4,4-(lower alkylendioxy)-1-piperidinyl, 3-hydroxy-1piperidinyl, and the like.

The symbol $Q^1$ and the nitrogen atom together preferably are the group of the formula $>N-CH_2CH_2-$ (a) or $>N-CH=CH-$ (c). The symbol Ra preferably is a phenyl group which is optionally substituted by m-halogen or m-trifluoromethyl, with the value phenyl being especially preferred. The symbols Rb and Rc together with the carbon atom denoted by α preferably are a group of the formula $>C_\alpha-S-CH=CH-$ (h) or $>C_\alpha-CH=CH-CH=CH-$ (j) which is optionally substituted by halogen, especially the group of the formula $>C_\alpha-S-CH=CH-$ or $>C_\alpha-CH=C-Cl-CH=CH-$, and the dotted line is an additional bond. In a preferred embodiment, $Q^2$ is an oxygen atom, $A^2$ is the group —CO—, $R^1$ is the group —$NR^3R^4$, $R^3$ is lower alkoxyalkyl and $R^4$ is hydrogen or lower alkyl or $R^3$ and $R^4$ together with the nitrogen atom are a 4-, 5- or 6-membered, saturated N-heterocycle which is optionally substituted by one or two lower alkyl groups and optionally substituted by a hydroxy, lower alkoxy, lower hydroxyalkyl or lower alkoxyalkyl group and which can contain as a ring member an oxygen atom, and either m and q is 0 and n is 1 or m and q is 1 and n is 0. In an especially preferred embodiment, $A^1$ is methylene, $Q^2$ is an oxygen atom, $A^2$ is the group —CO—, $R^1$ is the group —$NR^3R^4$, $R^3$ is lower alkoxyalkyl and $R^4$ is hydrogen or lower alkyl or $R^3$ and $R^4$ together with the nitrogen atom is a 1-azetidinyl, 1-pyrrolidinyl, -piperidinyl or 4-morpholinyl group which is optionally substituted by one or two lower alkyl groups and optionally substituted by a hydroxy, lower alkoxy, lower hydroxyalkyl or lower alkoxyalkyl group and either m and q are 0 and n is 1, or m and q are 1 and n is 0. In a particularly preferred embodiment, $A^1$ is methylene, $Q^2$ is an oxygen atom, $A^2$ is the group —CO—, $R^1$ is the group —$NR^3R^4$, $R^3$ is 2-(lower alkoxy)ethyl and $R^4$ is hydrogen or lower alkyl or $R^3$ and $R^4$ together with the nitrogen atom are 3-(lower alkoxy)-1-azetidinyl, 3-(lower alkoxy)-1-pyrrolidinyl, 2-(lower alkoxyalkyl)-1-pyrrolidinyl, 2-(lower hydroxyalkyl)-1-pyrrolidinyl, 4-hydroxy-1-piperidinyl, 4-(lower alkoxy)-1-piperidinyl, 4-morpholinyl or 2,6-di(lower alkyl)-4-morpholinyl and either m and q are 0 and n is 1 or m and q are 1 and n is 0. In a special embodiment, m and q are 0, n is 1 and $R^1$ is hydroxy or lower alkoxy.

Particularly preferred compounds of formula I of the invention are:

10-Chloro-6,7-dihydro-N-(2-methoxyethyl)-4-oxo-3-phenyl-4H-benzo[a]quinolizine-1-carboxamide,
1-[(10-chloro-6,7-dihydro-4-oxo-3-phenyl-4H-benzo[a]quinolizin-1-yl)carbonyl]-4-piperidinol,
(4,5-dihydro-7-oxo-8-phenyl-7H-thieno[2,3-a]quinolizin-10-yl)methyl 4-morpholinecarboxylate,
4-[(6,7-dihydro-4-oxo-3-phenyl-10-chloro-4H-benzo[a]quinolizin-1-yl)carbonyl]-2,6-dimethylmorpholine,
(S)-1-[(7-oxo-8-phenyl-7H-thieno[2,3-a]quinolizin-10-yl)carbonyl]-2-pyrrolidinemethanol,
(S)-2-methoxymethyl-1-[(7-oxo-8-phenyl-7H-thieno[2,3-a]quinolizin-10-yl)carbonyl]pyrrolidine,
1-[(10-chloro-4-oxo-3-phenyl-4H-benzo[a]quinolizin-1-yl)-carbonyl]-3-methoxypyrrolidine,
(S)-1-[(10-chloro-4-oxo-3-phenyl-4H-benzo[a]quinolizin-1-yl)carbonyl]-2-pyrrolidinemethanol,
cis-4-[(4,5-dihydro-7-oxo-8-phenyl-7H-thieno[2,3-a]quinolizin-10-yl)carbonyl]-2,6-dimethylmorpholine,
1-(10-chloro-6,7-dihydro-4-oxo-3-phenyl-4H-benzo[a]quinolizin-1-yl)-4-methoxypiperidine,
1-[(10-chloro-3-phenyl-4-oxo-4H-benzo[a]quinolizin-1-yl)carbonyl]-4-methoxypiperidine,
N-ethyl-N-(2-methoxyethyl)-7-oxo-8-phenyl-7H-thieno[2,3-a]quinolizine-10-carboxamide,
N-(2-methoxyethyl)-N-methyl-7-oxo-8-phenyl-7H-thieno[2,3-a]quinolizine-10-carboxamide,
(R)-2-(methoxymethyl)-1-[(7-oxo-8-phenyl-7H-thieno[2,3-a]quinolizin-10-yl)carbonyl]pyrrolidine,
1-[(10-chloro-6,7-dihydro-4-oxo-3-phenyl-4H-benzo[a]quinolizin-1-yl)carbonyl]-3-methoxypyrrolidine,
1-[(10-chloro-6,7-dihydro-4-oxo-3-phenyl-4H-benzo[a]quinolizin-1-yl)carbonyl]-3-ethoxypyrrolidine,
(R)-3-methoxy-1-[(7-oxo-8-phenyl-7H-thieno[2,3-a]quinolizin-10-yl)carbonyl]pyrrolidine,
(S)-3-methoxy-1-[(7-oxo-8-phenyl-7H-thieno[2,3-a]quinolizin-10-yl)carbonyl]pyrrolidine,
(S)-1-[(10-chloro-6,7-dihydro-4-oxo-3-phenyl-4H-benzo[a]quinolizin-1-yl)carbonyl]-2-(methoxymethyl)pyrrolidine,
1-[(4,5-dihydro-7-oxo-8-phenyl-7H-thieno[2,3-a]quinolizin-10-yl)carbonyl]-3-methoxypyrrolidine,
3-methoxy-1-[(7-oxo-8-phenyl-7H-thieno[2,3-a]quinolizin-10-yl)carbonyl]azetidine,
(R)-1-[(10-chloro-4-oxo-3-phenyl-4H-benzo[a]quinolizin-1-yl)carbonyl]-2-pyrrolidinemethanol,
(S)-1-[(10-chloro-4-oxo-3-phenyl-4H-benzo[a]quinolizin-1-yl)carbonyl]-2-(methoxymethyl)pyrrolidine and
(R)-1-[(10-chloro-4-oxo-3-phenyl-4H-benzo[a]quinolizin-1-yl)carbonyl]-2-(methoxymethyl)pyrrolidine.

Other preferred compounds of formula I are:

Methyl 8-(m-fluorophenyl)-4,5-dihydro-7-oxo-7H-thieno[2,3-a]quinolizine-10-carboxylate,
methyl 4,5-dihydro-7-oxo-8-phenyl-7H-thieno[2,3-a]quinolizine-10-carboxylate,
ethyl 4,5-dihydro-7-oxo-8-phenyl-7H-thieno[2,3-a]quinolizine-10-carboxylate,
isopropyl 4,5-dihydro-7-oxo-8-phenyl-7H-thieno[2,3-a]quinolizine-10-carboxylate,
tert-butyl 4,5-dihydro-7-oxo-8-phenyl-7H-thieno[2,3-a]quinolizine-10-carboxylate,
methyl 8-(m-chlorophenyl)-4,5-dihydro-7-oxo-7H-thieno[2,3-a]quinolizine-10-carboxylate,
methyl 10-chloro-6,7-dihydro-4-oxo-3-phenyl-4H-benzo[a]quinolizine-1-carboxylate and
methyl 6,7-dihydro-3-phenyl-4-oxo-4H-benzo[a]quinolizine-1-carboxylate.

The compounds of formula I and the pharmaceutically acceptable acid addition salts of compounds of formula I which have a basic substituent can be prepared in accordance with the invention by (a) reacting a compound of the formula

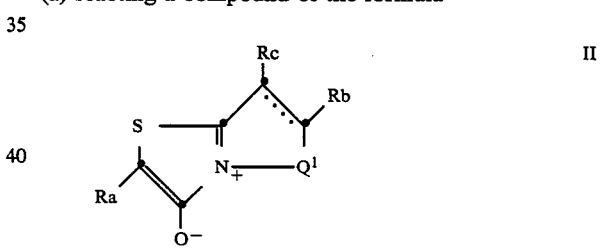

II wherein $Q^1$, Ra, Rb, Rc and the dotted line have the above significance,
at an elevated temperature with a compound of the formula HC.C-Rd′    III or H$_2$C=CH-Rd′    IV wherein Rd′ is cyano, nitro or the group of the formula —CO—$(Q^2A^2)_q$—$R^1$ and q, $A^2$, $Q^2$ and $R^1$ have the above significance,
or with phenylvinyl sulfoxide and, if necessary, treating the cycloaddition product obtained with a strong base,
or (b) reacting a compound of the formula ROOC—C(Ra)=CHR′    V wherein R is lower alkyl, R′ is hydrogen or lower alkoxy and Ra has the above significance,
with a compound of the formula

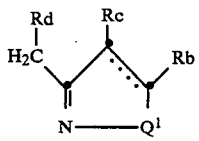     VI wherein $Q^1$, Rb, Rc, Rd and the dotted line have the above significance,
at an elevated temperature when R' is hydrogen or in the presence of a strong base when R' is lower alkoxy and dehydrogenating the cyclocondensation product obtained when R' is hydrogen, or
(c) hydrolyzing a compound of formula I which contains an esterified carboxy group, or
(d) esterifying a carboxylic acid of the formula

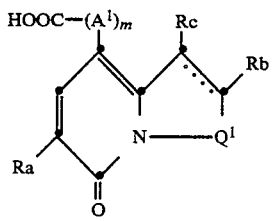     Ia wherein $A^1$, $Q^1$, Ra, Rb, Rc, m and the dotted line have the above significance,
with an alcohol of the formula

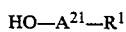     VII wherein $A^{21}$ is lower alkylene or a direct bond and $R^1$ has the above significance,
or
(e) converting a carboxylic acid of formula Ia above or a carboxylic acid of the formula

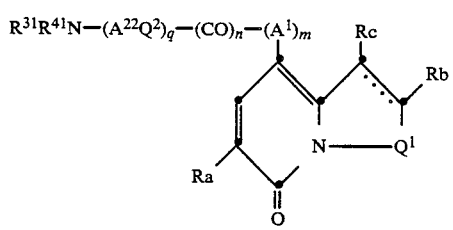     VIIIa wherein $A^{22}$ is lower alkylene or the group —CO— and $R^{31}$ and $R^{41}$ together with the nitrogen atom is a 3- to 7-membered, saturated N-heterocycle which is optionally substituted by one or two lower alkyl groups and which is substituted by a carboxy group and which can contain as a ring member an oxygen or sulfur atom or the group >N—$R^5$ and $A^1$, $Q^1$, $Q^2$, Ra, Rb, Rc, $R^5$, m, n, q and the dotted line have the above significance,
or a reactive derivative thereof into the corresponding amide with an amine of the formula

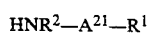     IX or

     X wherein $A^{21}$, $R^1$, $R^2$, $R^3$ and $R^4$ have the above significance,
or with ammonia or a mono- or di(lower alkyl)amine, respectively, or
(f) reacting a compound of the formula

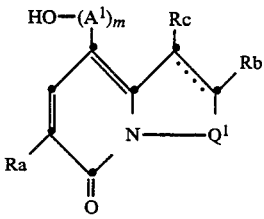     Ib' wherein $A^1$, $Q^1$, Ra, Rb, Rc, m and the dotted line have the above significance,
in the presence of a base with a compound of the formula

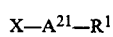     XI wherein X is a leaving group and $R^{21}$ and $R^1$ have the above significance,
or reacting a compound of formula I which contains a free hydroxy group with a compound of the formula

R—X     XII wherein R is lower alkyl and X has the above significnce,
or
(g) reacting a compound of the formula

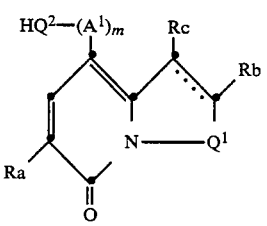     Ib wherein $A^1$, $Q^1$, $Q^2$, Ra, Rb, Rc, m and the dotted line have the above significance,
in the presence of an acid-binding agent with a reactive derivative of a carboxylic acid of the formula $R^1$—COOH     XIII wherein $R^1$ has the above significance,
or
(h) reacting a compound of the formula

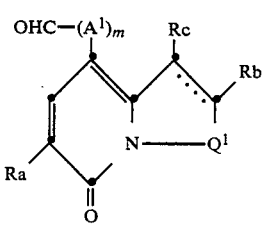     Ic wherein $A^1$, $Q^1$, Ra, Rb, Rc, m and the dotted line have the above significance, in the presence of a reduction agent with an amine of formula IX or X above, or (i) reducing a compound of the formula

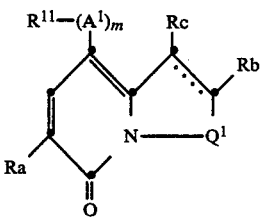   Id wherein $R^{11}$ is nitro, cyano or lower alkoxycarbonyl and $A^1$, $Q^1$, Ra, Rb, Rc, m and the dotted line have the above significance, or a compound of formula Ia above or a reactive derivative thereof, or (j) oxidizing an alcohol of formula Ib' above or an alcohol of the formula

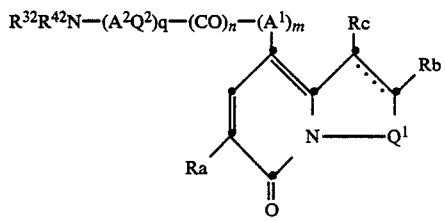   Ie wherein $A^1$, $A^2$, $Q^1$, $Q^2$, Ra, Rb, Rc, m, n, q and the dotted line have the above significance and $R^{32}$ and $R^{42}$ together with the nitrogen atom is a 3- to 7-membered, saturated N-heterocycle which is optionally substituted by one or two lower alkyl groups and which is substituted by a hydroxy group and which can contain as a ring member an oxygen or sulfur atom or the grop $>N-R^5$ and $R^5$ has the above significance, or (k) reacting an isocyanate of the formula

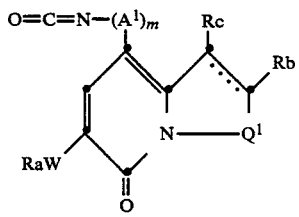

VIIIb           or $O=C-N-R^{33}$ XIV wherein $A^1$, $Q^1$, Ra, Rb, Rc, m and the dotted line have the above significance and $R^{33}$ is hydrogen, lower alkyl or ($C_{3-7}$)-cycloalkyl, with a lower alcohol or an amine of formula X above or with a compound of formula Ib above, respectively, or (l) reacting a compound of the formula

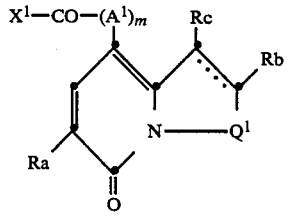   VIIIc wherein $X^1$ is a halogen atom and $A^1$, $Q^1$, Ra, Rb, Rc, m and the dotted line have the above significance, with a lower alkylmagnesium halide, or (m) dehydrohalogenating a compound of the formula

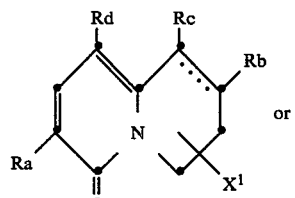   XVA or

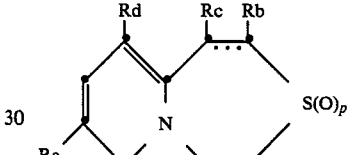   XVb wherein Ra, Rb, Rc, Rd, $X^1$, the dotted line and p have the above significance, in the presence of a base, or (n) S-oxidizing a compound of the formula

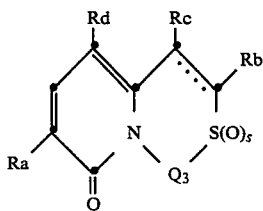   If wherein $Q^3$ is the group $-CH_2-$, $-CH_2CH_2-$ or $-CH=CH-$, s is 0 or 1 and Ra, Rb, Rc, Rd and the dotted line have the above significance, or (o) heating a compound of the formula

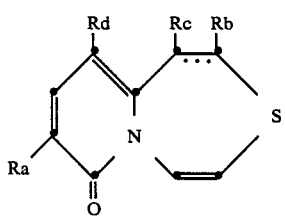   Ig wherein Ra, Rb, Rc, Rd and the dotted line have the above significance, or (p) halogenating a compound of the formula

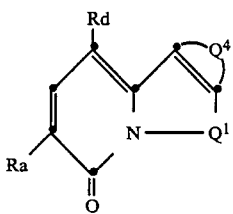 Ih wherein $Q^4$ is the group (h) or (i) above and $Q^1$, Ra and Rd have the above significance,
or the thiophene ring, or (q) reacting a compound of formula VIIIc above in the presence of a base with a compound of the formula

 XVI,

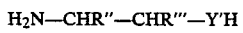 XVII or

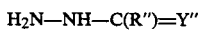 XVIII wherein Y is an oxygen atom or the group —NR'''—, Y' is an oxygen atom or the group —NH—, Y'' is an oxygen or sulfur atom and R'' and R''' each, independently, are hydrogen or lower alkyl,
and cyclizing the product obtained, or (r) reacting a compound of the formula

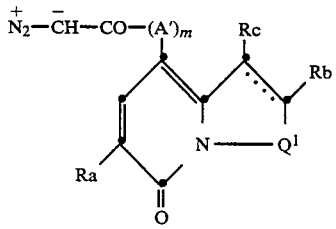 VIIId wherein A' is $C_{1-6}$-alkylene and $Q^1$, Ra, Rb, Rc, the dotted line and m have the above significance,
with a lower alcohol, or (s) decarboxylating a carboxylic acid of formula Ia in which m is 0, or (t) halogenating a compound of formula I in which Rd is hydrogen on the pyridone ring, or (u) cleaving the acetal group in a compound of the formula

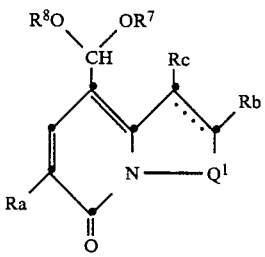 VIIIe wherein $R^7$ and $R^8$ each is lower alkyl or taken together are lower alkylene and $Q^1$, Ra, Rb, Rc and the dotted line have the above significance,
or (v) hydrogenating a compound of formula I in which $Q^1$ and the nitrogen atom taken together are the group >N—CH=CH—, or (w) reacting a compound of the formula

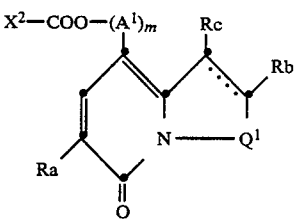 VIIIf wherein $X^2$ is phenoxy and $A^1$, $Q^1$, Ra, Rb, Rc, the dotted line and m have the above significance,
with an amine of formula X above, and (x) if desired, converting a compound of formula I obtained which has a basic substituent into a pharmaceutically acceptable acid addition salt.

In several of the above processes in accordance with the invention the reactive amino, carboxy and/or hydroxyl groups which may be present in the starting materials must be blocked by protecting groups. These instances are readily recognizable by persons skilled in the art, and the choice of protecting groups which are suitable in a given case also presents no difficulties to such persons.

Compounds of formula I in which Rd is hydrogen, cyano, nitro or the group of the formula —CO—($Q^2A^2$)$_q$—$R^1$ and q, $A^2$, $Q^2$ and $R^1$ have the above significance can be prepared in accordance with process variant (a). The reaction is conveniently carried out in an invert solvent which boils at an elevated temperature, preferably above 80° C. Suitable solvents are, for example, aromatic hydrocarbons such as benzene, toluene and xylene, in which case the reaction is preferably carried out at the reflux temperature of the solvent.

When the reaction of a compound of formula II with a compound of formula III or with phenylvinyl sulfoxide is carried out at an elevated temperature the corresponding compound of formula I is obtained directly. When a compound of formula II is reacted with a compound of formula IV there is obtained first, as the cycloaddition product, the corresponding epithio compound of the formula

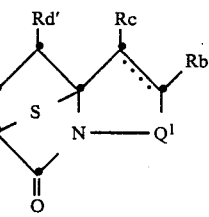 XIX wherein Ra, Rb, Rc, Rd', $Q^1$ and the dotted line have the above significance,
which is subsequently converted into the corresponding compound of formula I by treatment with a strong base. Suitable bases are, for example, the lower alkali metal alcoholates such as sodium methylate, in which case the corresponding lower alcohol is conveniently used as the solvent. The reaction is preferably carried out at the reflux temperature of the solvent.

The reaction of a compound of formula V in which R' is hydrogen with a compound of formula VI in accordance with process variant (b) can be carried out without a solvent or in the presence of a solvent which boils at an elevated temperature. Suitable solvents are, for example, aromatic hydrocarbons such as benzene, toluene and xylene. The cyclocondensation is, however, preferably carried out without a solvent in a temperature range of about 80° C. to about 150° C. The thus-obtained cyclocondensation product, namely, a compound of the formula

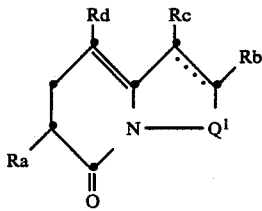

XXa wherein Ra, Rb, Rc, Rd, $Q^1$, and the dotted line have the above significance.
is subsequently dehydrogenated with a suitable oxidation agent such as manganese dioxide. Suitable solvents are, for example, aromatic hydrocarbons such as benzene, toluene and xylene. The dehydrogenation is preferably carried out at a temperature in the range of from about room temperature to the boiling temperature of the chosen solvent, preferably at the boiling temperature.

By reacting a compound of formula V in which R' is lower alkoxy in the presence of a strong base such as sodium hydride and in an inert solvent, preferably in an ether such as tetrahydrofuran, with a compound of formula VI in accordance with process variant (b) there is obtained the corresponding compound of formula I. The reaction temperature is in a range of from room temperature to the boiling temperature of the reaction mixture.

The compounds of formulas XIX and XXa also form part of the invention.

Compounds of formula I which contain an esterified carboxy group can be hydrolyzed in accordance with process variant (c), whereby the corresponding free carboxylic acids are obtained. The hydrolysis can be carried out according to known methods. The hydrolysis is preferably carried out with an alkali metal hydroxide such as sodium hydroxide and potassium hydroxide in a lower alcohol such as methanol and ethanol or in a mixture of a lower alcohol and water. The reaction temperature conveniently lies in a range of room temperature to the boiling temperature of the reaction mixture, preferably at the boiling temperature of the reaction mixture.

Compounds of formula I in which Rd is the group of the formula $-(A^1)_m-CO-O-A^{21}-R^1$ and $A^1$, $A^{21}$, $R^1$ and m have the above significance can be prepared by esterifying a carboxylic acid of formula Ia with an alcohol of formula VII in accordance with process variant (d). The esterification can be carried out, for example, in the presence of an esterification reagent in an inert organic solvent. Suitable reagents are, for example, N-methyl-2-chloropyridinium iodide and the like, organic sulfonic acid halides such as methylsulfonyl chloride, p-toluenesulfonyl chloride and mesitylenesulfonic acid chloride, and the like. Suitable solvents are, for example, halogenated hydrocarbons such as methylene chloride, chloroform and the like. Suitable bases are, for example, tertiary amines such as triethylamine, tri-n-butylamine and the like. The reaction is preferably carried out at a temperature an the range of from room temperature to the reflux temperature of the solvent.

The desired esterification can also be carried out by firstly converting the carboxylic acid of formula Ia into a reactive derivative and then reacting this with an alcohol of formula VII in the presence of a base. The corresponding carboxylic acid chlorides are preferably used as the reactive derivatives. Suitable bases are, for example, the tertiary amines mentioned previously. The reaction is preferably carried out at a temperature in the range of from about room temperature to the reflux temperature of the reaction mixture, conveniently at room temperature.

The esterification with an alcohol of formula VII in which $A^{21}$ is lower alkylene and $R^1$ is hydrogen, that is, with a lower alcohol, can also be carried out by reacting the carboxylic acid with a N,N-dimethylformamide di(lower alkyl)acetal. The reaction wit a N,N-dimethylformamide di(lower alkyl)acetal is preferably carried out in an inert solvent, for example, in an aromatic hydrocarbon such as benzene, at the reflux temperature of the reaction mixture.

Compounds of formula I in which Rd is the group $-(A^1)_m-CO-NR^2-A^{21}-R^1$ or $-(A^1)_m-CO-NR^3R^4$ and $A^1$, $A^{21}$, $R^1$, $R^2$, $R^3$, $R^4$ and m have the above significance can be prepared by reacting a carboxylic acid of formula Ia or a reactive derivative thereof with an amine of formula IX or X in accordance with process variant (e).

By reacting a carboxylic acid of formula VIIIa or a reactive derivative thereof with ammonia or a mono- or di(lower alkyl)amine in accordance with process variant (e) there can be prepared corresponding compounds of formula I in which $R^1$ is a group of the formula $-NR^3R^4$ and $R^3$ and $R^4$ taken together with the nitrogen atom are a 3- to 7-membered, saturated N-heterocycle which is optionally substituted by one or two lower alkyl groups and which is substituted by a carbamoyl or mono- or di(lower alkyl)carbamoyl group which can contain as a ring member an oxygen or sulfur atom or the group $>N-R^5$ and $R^5$ has the above significance.

If the free carboxylic acid of formula Ia or VIIIa is used as the starting material, then the amidation reaction is preferably carried out in the presence of a condensation agent such as N-methyl-2-chloropyridinium iodide in an inert organic solvent and in the presence of a base. Suitable solvents are, for example, aromatic hydrocarbons such as benzene, toluene and xylene. Suitable bases are, for example, the tertiary amines mentioned above. Preferred reactive carboxylic acid derivatives which can be reacted in the presence of a base directly with the corresponding amine are the corresponding carboxylic acid chlorides. Suitable bases are again the previously mentioned tertiary amines. Suitable solvents are, for example, aromatic hydrocarbons such as benzene, toluene and xylene and ethers such as dioxane. In both cases the reaction is preferably carried out at the reflux temperature of the reaction mixture.

In accordance with process variant (f) there can be prepared on the one hand compounds of formula I in which Rd is a group of the formula $-(A^1)_m-O-A^{21}-R^1$ and $A^1$, $A^{21}$, $R^1$ and m have the above significance, and on the other hand compounds of formula I which contain a hydroxy group which is etherified in the form of a lower alkyl ether.

The reaction of a compound of formula Ib' with a compound of formula XI or the reaction of a compound of formula I which contains a free hydroxy group with a compound of formula XII is conveniently carried out in an inert organic solvent such as N,N-dimethylformamide or the like, with a strong base, for example, an alkali metal hydride or hydroxide such as sodium hydride, potassium hydroxide and sodium hydroxide being conveniently used as the base. The reaction is conveniently carried out at a temperature in the range of from 0° C. to room temperature. The leaving group denoted by X is preferably a halogen atom, especially a chlorine, bromine or iodine atom, or an alkyl- or arylsulfonyloxy group, for example, a methanesulfonyloxy or p-toluenesulfonyloxy group. In the preparation of lower alkyl ethers X can also be a lower alkoxysulfonyloxy group, that is, the alkylating agent in this case is a di(lower alkyl) sulfate such as dimethyl sulfate.

Compounds of formula I in which Rd is a group of the formula $-(A^1)_m-Q^2-CO-R^1$ and $A^1$, $Q^2$, $R^1$ and m have the above significance can be prepared in accordance with process variant (g).

The reaction of a compound of formula Ib with a reactive derivative of a carboxylic acid of formula XIII, for example a carboxylic acid chloride, is conveniently carried out in an inert organic solvent in the presence of an acid-binding agent, for example a tertiary amine. Suitable solvents are, for example, aromatic hydrocarbons such as benzene, toluene and xylene and halogenated hydrocarbons such as methylene chloride. When $R^1$ is lower alkyl, corresponding carboxylic acid anhydrides can also be used, and pyridine can conveniently be used as the solvent and as the acid-binding agent in this case. The reaction is preferably carried out in a temperature range of about 0° C. to the boiling temperature of the solvent.

Compounds of formula I in which Rd is a group of the formula $-(A^1)_m-CH_2-NR^2A^{21}-R^1$ or $-(A^1)_m-CH_2-NR^3R^4$ and $A^1$, $A^{21}$, $R^1$, $R^2$, $R^3$, $R^4$ and m have the above significance can be prepared in accordance with process variant (h). The reaction is preferably carried out in a lower alcohol as the solvent and with sodium cyanoborohydride as the reduction agent, the reaction being conveniently carried out at room temperature and the amine being conveniently used in the form of its hydrochloride.

Compounds of formula I in which Rd is a group of the formula $-(A^1)_m-R^{12}$ and $R^{12}$ is amino, aminomethyl, hydroxymethyl or methyl and $A^1$ and m have the above significance can be prepared in accordance with process variant (i). The choice of the suitable reduction agent depends on the one hand on the starting material which is used and on the other hand on the product which is desired. A compound of formula Id in which $R^{11}$ is cyano can, for example, be reduced with diborane in tetrahydrofuran to the corresponding aminomethyl compound. A compound of formula Id in which $R^{11}$ is nitro can, for example, be reduced with sodium sulfide in a lower alcohol such as methanol to the corresponding amino compound. A compound of formula Id in which $R^{11}$ is lower alkoxycarbonyl can be reduced with lithium borohydride to the corresponding hydroxymethyl compound and the acid chloride of a compound of formula Ia can be reduced with sodium borohydride in tetrahydrofuran and/or dimethylformamide to the corresponding hydroxymethyl compound. A carboxylic acid of formula Ia can, for example, be reduced with borane/tetrahydrofuran complex or borane/methyl sulfide complex in tetrahydrofuran to the corresponding methyl compound.

Compounds of formula I in which Rd is a group of the formula $-(A^1)_m-CHO$ or $-(A^1)_m-(CO)_n-(Q-^2A^2)_q-NR^{34}R^{44}$ and $R^{34}$ and $R^{44}$ together are a 3- to 7-membered, saturated N-heterocycle which is optionally substituted by one or two lower alkyl groups and which is substituted by an oxo group and which contains as a ring member an oxygen or sulfur atom or the group $>N-R^5$ and $A^1$, $A^2$, $Q^2$, m, n and q have the above significance can be prepared in accordance with process variant (j). The oxidation of alcohols of formulas Ib' and Ie can be carried out according to methods which are known and which are familiar to any person skilled in the art. For example, the desired oxidation can be carried out with manganese dioxide in a halogenated hydrocarbon such as methylene chloride at room temperature. However, the desired oxidation can also be carried out with pyridinium chlorochromate in a halogenated hydrocarbon such as methylene chloride at room temperature or with dimethyl sulfoxide/trifluoroacetic acid anhydride in a halogenated hydrocarbon such as methylene chloride at temperatures of about —70° C.

Compounds of formula I in which Rd is a group of the formula $-(A^1)_m-NHCO-R^{13}$, $-(A^1)_m-NH-CO-NR^3R^4$ or $-(A^1)_m-Q^2-CO-NH-R^{33}$ and $R^{13}$ is lower alkoxy and $A^1$, $Q^2$, $R^3$, $R^{33}$, $R^4$ and m have the above significance can be prepared in accordance with process variant (k) by reacting an isocyanate of formula VIIIb with a lower alcohol or an amine of formula X or by reacting an isocyanate of formula XIV with a compound of formula Ib. This reaction is conveniently carried out in a inert solvent, for example in an aromatic hydrocarbon such as benzene, toluene or xylene, in a halogenated hydrocarbon such as methylene chloride or in an ether such as dioxane. The reaction is preferably carried out at a temperature in the range of from about room temperature to the boiling temperature of the reaction mixture. If an isocyanate of formula XIV in which $R^{33}$ is hydrogen is used as the starting material, then this is conveniently used in protected form. An especially suitable protecting group in this case is the trichloroacetyl group which can be removed by hydrolysis, for example with potassium carbonate in water, after the reaction has been carried out.

Compounds of formula I in which Rd is a group of the formula $-(A^1)_m-CO-R^{14}$ and $R^{14}$ is lower alkyl and $A^1$ and m have the above significance can be prepared in accordance with process variant (l). Ethers such as tetrahydrofuran and diethyl ether are preferably used as the solvent. The reaction is preferably carried out at a temperature in the range of from —78° C. to room temperature.

Compounds of formula I in which $Q^1$ and the nitrogen atom together are a group of the formula $>N-CH=CH$ (c) or $>N-CH=CH-S(O)_p$ (g) and p has the above significance can be prepared in accordance with process variant (m). This dehydrohalogenation is preferably carried out in an inert organic solvent, for example, in a halogenated lower hydrocarbon such as carbon tetrachloride or in dimethyl sulfoxide and dimethylformamide, and in the presence of a basic amine, for example, a tertiary amine such as triethylamine, or a bicyclic amidine such as 1,5-diazabicyclo[4.3.0.]non-5-ene as the base. The reaction is conveniently carried out at a temperature in the range of from room temperature to about 100° C.

Compounds of formula I in which $Q^1$ and the nitrogen atom together are a group of the formula >N—CH$_2$—S(O)$_t$—, >N—CH$_2$CH$_2$—S(O)$_t$— or >N—CH=CH—S(O)$_t$ and t is 1 or 2 can be prepared in accordance with process variant (n). This S-oxidation is preferably carried out with an oxidation agent such as m-chloroperbenzoic acid in a halogenated hydrocarbon such as methylene chloride at a temperature in the range of about −20° C. to about room temperature.

Compounds of formula I in which $Q^1$ and the nitrogen atom taken together are a group of the formula >N—CH=CH— (a) can be prepared in accordance with process variant (o). This reaction is preferably carried out in a high-boiling aromatic hydrocarbon such as xylene at the reflux temperature.

Compounds of formula I in which Rb and Rc taken together with the carbon atom denoted by α are a group of the formula >C$_α$—S—CH=CH— (h) or >C$_α$—CH=CH—S— (i) which is substituted by halogen and the dotted line is an additional bond can be prepared in accordance with process variant (p). Elementary halogen, for example elementary bromine, is preferably used as the halogenating agent. Suitable solvents are, for example, halogenated hydrocarbons such as chloroform. The halogenation is conveniently carried out at a temperature in the range of from 0° C. to about room temperature.

Compounds of formula I in which Rd is a group of the formula —(A$^1$)$_m$—R$^{15}$ and R$^{15}$ is a 5-membered, partially unsaturated or aromatic heterocycle which is attached via a carbon atom and which is optionally substituted by one or two lower alkyl groups and A$^1$ and m have the above significance can be prepared in accordance with process variant (q). The reaction of a compound of formula VIIIc with a compound of formula XVI, XVII or XVIII is conveniently carried out in an inert solvent, for example in a halogenated hydrocarbon such as methylene chloride or in an aromatic hydrocarbon such as benzene, toluene or xylene, and at a temperature in the range of from about 0° C. to the reflux temperature of the reaction mixture. Suitable bases are, for example, the tertiary amines mentioned previously. The cyclization of the thus-obtained product can be carried out according to methods which are known and which are familiar to any person skilled in the art. The cyclization can be carried out, for example, in the presence of catalytic amounts of a strong acid such as p-toluenesulfonic acid while removing the reaction water which is formed by means of a drying agent such as toluene. However, the cyclization can also be carried out by means of diethyl azodicarboxylate/triphenylphosphine in an ether such as tetrahydrofuran.

Compounds of formula I in which Rd is a group of the formula —(A')$_m$—CH$_2$—R$^{16}$, A' is C$_{1-6}$—alkyl and R$^{16}$ is lower alkoxycarbonyl and m has the above significance can be prepared in accordance with process variant (r). The reaction of a diazoketone of formula VIIId with a lower alcohol is preferably carried out in the presence of a silver catalyst such as silver oxide, the lower alcohol being preferably used as the solvent. The reaction is carried out at an elevated temperature, preferably at the boiling temperature of the reaction mixture.

Compounds of formula I in which Rd is hydrogen can be prepared in accordance with process variant (s). The decarboxylation of a carboxylic acid of formula Ia is preferably carried out by dry heating, especially by dry heating in vacuo to temperatures of about 200° to about 300° C.

Compounds of formula I in which Rd is halogen can be prepared in accordance with process variant (t). Suitable halogenating agents for the present halogenation are N-haloamides and N-haloamides such as N-chlorosuccinimide, N-bromosuccinimide, N-chloroacetamide and the like. A halogenated hydrocarbon such as methylene chloride, chloroform, carbon tetrachloride and the like is preferably used as the solvent. The reaction can be carried out at a temperature in the range of from about 0° C. to the boiling temperature of the reaction mixture. The reaction is preferably carried out at room temperature.

Compounds of formula I in which Rd is the group —CHO can be prepared by cleaving the acetal group in a compound of formula VIIIe in accordance with process variant (u). The cleavage is preferably carried out by trans-acetalization in the presence of an acid such as p-toluenesulfonic acid and a ketone such as cyclohexanone, acetone and the like. The reaction can be carried out at a temperature an the range of from room temperature to the boiling temperature of the reaction mixture.

Compounds of formula I in which $Q^1$ and the nitrogen atom together are the group >N—CH$_2$CH$_2$— can be prepared in accordance with process variant (v). The hydrogenation is conveniently carried out in the presence of a noble metal catalyst such as platinum oxide and palladium/carbon in a solvent which is suitable for such purpose, for example, in a lower alcohol or in a lower fatty acid ester such as ethyl acetate. The hydrogenation is preferably carried out at room temperature.

Compounds of formula I in which Rd is a group of the formula —(A$^1$)$_m$—OCO—NR$^3$R$^4$ can be prepared in accordance with process variant (w). Suitable solvents are, for example, ethers such as tetrahydrofuran, dioxane and diethyl ether, N,N-dimethylformamide and dimethyl sulfoxide. The reaction is conveniently carried out at room temperature.

Compounds of formula I which have one or more basic substituents can be converted into pharmaceutically acceptable acid addition salts in accordance with process variant (x). Such acid addition salts can be prepared according to methods which are known and which are familiar to any person skilled in the art. There come into cosideration not only salts with inorganic acids, but also salts with organic acids, for example hydrochlorides, hydrobramides, sulfates, nitrates, citrates, acetates, maleates, succinates, methanesulfonates, p-toluensulfonates and the like.

The compounds of formulas II, VIIIa, VIIIb, VIIIc, VIIId, VIIIe, VIIIf, XVa and XVb which are used as starting materials also form part of the invention. These substances can be prepared as described hereinafter.

The compounds of formula II can be prepared, for example, be reacting a compound of the formula

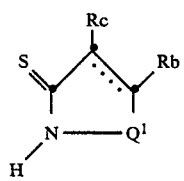

XXI wherein $Q^1$, Rb, Rc and the dotted line have the above significance,
with a compound of the formula

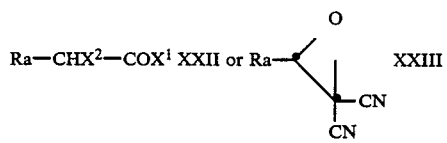

wherein $X^1$ and $X^2$ each is halogen and $R^1$ has the above significance.

The reaction of a compound of formula XXI with a compound of formula XXII in which $X^1$ preferably is chlorine and $X^2$ preferably is bromine is preferably carried out at room temperature in a halogenated hydrocarbon such as chloroform, whereupon treatment is carried out with a basic amine such as triethylamine. The reaction of a compound of formula XXI with a compound of formula XXIII is preferably carried out in an inert solvent such as acetone, N,N-dimethylformamide, dimethyl sulfoxide and the like at room temperature.

The carboxylic acids of formula VIIIa can be prepared by hydrolyzing the corresponding lower alkyl esters of formula I. This hydrolysis can be carried out according to known methods, for example in analogy to process variant (c).

The isocyanates of formula VIIIb can be prepared by treating a compound of formula Ib in which $Q^2$ is a group of the formula —NH— in an inert solvent with phosgene. Suitable solvents are, for example, halogenated hydrocarbons such as chloroform and 1,2-dichloroethane. However, the isocyanates of formula VIIIb can also be prepared by converting a carboxylic acid halide of formula VIIIc in an inert organic solvent with an azide such as sodium azide or trimethylsilyl azide into the corresponding carboxylic acid azide and rearranging this to the corresponding isocyanate by heating. Suitable solvents are, for example, ethers such as dioxane, ethylene glycol dimethyl ether, diethylene glycol dimethyl ether and the like, ketones such as ethyl methyl ketone, and the like. The rearrangement is carried out at temperatures of 80° C. and above.

The carboxylic acid halides of formula VIIIc can be prepared by treating a carboxylic acid of formula Ia with a halogenating agent. Suitable halogenating agents are, for example, thionyl chloride, oxalyl chloride, phosphorus pentachloride and the like. In a preferred embodiment, excess thionyl chloride is used and the reaction is carried out without an additional solvent at room temperature.

The diazoketones of formula VIIId can be prepared by reacting a carboxylic acid halide of formula VIIIc in an inert organic solvent with diazomethane. Suitable solvents are, for example, ethers such as tetrahydrofuran, dioxane and diethyl ether. The reaction is preferably carried out at a temperature in the range of from about 0° C. to about 10° C.

The compounds of formula VIIIe can be prepared in analogy to process variant (a), wherein, as the starting material, a compound of the formula HC.C—CH(OR$^7$-)OR$^8$ in which $R^7$ and $R^8$ have the above significance is utilized.

The compounds of formula VIIIf can be prepared by reacting a compound of formula Ib' in an inert solvent, for example in an ether such as dioxane, and in the presence of a base, for example a basic amine such as pyridine, with phenyl chloroformate.

The compounds of formula XVa can be prepared by treating a compound of formula I in which $Q^1$ and the nitrogen atom together is the group >N—CH$_2$CH$_2$— with a N-halosuccinimide such as N-bromosuccinimide. The compound of formula XVa is preferably not isolated, but is dehydrohalogenated directly, with triethylamine being preferably used as the base.

The compounds of formula XVb can be prepared by treating a compound of formula I in which $Q^1$ and the nitrogen atom together are a group of the formula >N—CH$_2$CH$_2$—SO— without additional solvent with a halogenating agent such as thionyl chloride.

The remaining compounds which are used as starting materials belong to classes of known substances. The Examples which follow hereinafter contain detailed information concerning the preparation of all starting materials.

As mentioned earlier, the compounds of formula I have valuable pharmacological properties. In particular, they display pronounced muscle relaxant, sedative-hypnotic, anticonvulsive and/or anxiolytic properties and exhibit low toxicity. These properties can be demonstrated, for example, in the antipentetrazole test which is described hereinafter and which is generally recognized for demonstrating such properties.

In this animal test, the compound under investigation is adminstered orally or intravenously to female rats and 30 minutes later there are administered intraperitioneally 120 mg/kg of pentetrazole, which causes emprosthotonus and tonic stretchings of the fore and/or hind limbs in unprotected animals 1-4 minutes after the injection. Ten (10) experimental animals are used per dosage of test substance. After counting the protected experimental animals, the ED$_{50}$ is determined according to the Prohibit method. The ED$_{50}$ is that dosage which protects 50% of the experimental animals from the spasmodic seizures caused by pentetrazole. The results which have been obtained with representative members of the class of compound defined by formula I in the experiment described previously are compiled in the following Table. Moreover, the Table contains data concerning the acute toxicity (LD$_{50}$) of some of the compounds of formula I in mg/kg in the case of single oral administration to mice.

TABLE

| Compound | ED$_{50}$ in mg/kg p.o. | LD$_{50}$ in mg/kg p.o. |
| --- | --- | --- |
| A | 2.6 | >5000 |
| B | 5.4 | >5000 |
| C | 15.9 | — |
| D | 1.2 | >5000 |
| E | 3.5 | 625 |
| F | 2.8 | 5000 |
| G | 0.12 | 2500 |
| H | 1.3 | >3000 |
| I | 5.9 | >5000 |
| K | 0.56 | >5000 |
| L | 0.22 | >5000 |
| M | 5.0 | 5000 |
| N | 0.97 | 625 |
| O | 0.49 | 5000 |
| P | 0.31 | >5000 |
| Q | 3.1 | >5000 |
| R | 0.17 | 1250 |
| S | 0.87 | 5000 |
| T | 3.8 | >5000 |
| U | 2.7 | >5000 |
| V | 0.13 | >5000 |
| W | 0.51 | >3000 |
| X | 1.1 | 5000 |
| Y | 0.41 | 5000 |

A = 10-Chloro-6,7-dihydro-N—(2-methoxyethyl)-4-oxo-3-phenyl-4H—benzo[a]quinolizine-1-carboxamide.

TABLE-continued

B = 1-[(10-Chloro-6,7-dihydro-4-oxo-3-phenyl-4H—benzo[a]-quinolizin-1-yl)carbonyl]-4-piperidinol.
C = (4,5-Dihydro-7-oxo-8-phenyl-7H—thieno[2,3-a]quinolizin-10-yl)methyl 4-morpholinecarboxylate.
D = 4-[(6,7-Dihydro-4-oxo-3-phenyl-10-chloro-4H—benzo[a]-quinolizin-1-yl)carbonyl]-2,6-dimethylmorpholine.
E = (S)—1-[(7-Oxo-8-phenyl-7H—thieno[2,3-a]quinolizin-10-yl)carbonyl]-2-pyrrolidinemethanol.
F = (S)—2-Methoxymethyl-1-[(7-oxo-8-phenyl-7H—thieno-[2,3-a]quinolizin-10-yl)carbonyl]pyrrolidine.
G = 1-[(10-Chloro-4-oxo-3-phenyl-4H—benzo[a]quinolizin-1-yl)carbonyl]-3-methoxypyrrolidine.
H = (S)—1-[(10-Chloro-4-oxo-3-phenyl-4H—benzo[a]quinolizin-1-yl)carbonyl]-2-pyrrolidinemethanol.
I = cis-4-[(4,5-Dihydro-7-oxo-8-phenyl-7H—thieno[2,3-a]-quinolizin-10-yl)carbonyl]-2,6-dimethylmorpholine.
K = 1-(10-Chloro-6,7-dihydro-4-oxo-3-phenyl-4H—benzo[a]-quinolizin-1-yl)-4-methoxypiperidine.
L = 1-[(10-Chloro-3-phenyl-4-oxo-4H—benzo[a]quinolizin-1-yl)carbonyl]-4-methoxypiperidine.
M = N—Ethyl-N—(2-methoxyethyl)-7-oxo-8-phenyl-7H—thieno[2,3-a]quinolizine-10-carboxamide.
N = N—(2-Methoxyethyl)-N—methyl-7-oxo-8-phenyl-7H—thieno-[2,3-a]quinolizine-10-carboxamide.
O = (R)—2-(Methoxymethyl)-1-[(7-oxo-8-phenyl-7H—thieno-[2,3-a]quinolizin-10-yl)carbonyl]pyrrolidine.
P = 1-[(10-Chloro-6,7-dihydro-4-oxo-3-phenyl-4H—benzo[a]-quinolizin-1-yl)carbonyl]-3-methoxypyrrolidine.
Q = 1-[(10-Chloro-6,7-dihydro-4-oxo-3-phenyl-4H—benzo[a]-quinolizin-1-yl)carbonyl]-3-ethoxypyrrolidine.
R = (R)—3-Methoxy-1-[(7-oxo-8-phenyl-7H—thieno[2,3-a]-quinolizin-10-yl)carbonyl]pyrrolidine.
S = (S)—3-Methoxy-1-[(7-oxo-8-phenyl-7H—thieno[2,3-]-quinolizin-10-yl)carbonyl]pyrrolidine.
T = (S)—1-[(10-Chloro-6,7-dihydro-4-oxo-3-phenyl-4H—benzo-[a]quinolizin-1-yl)carbonyl]-2-(methoxymethyl)pyrrolidine.
U = 1-[(4,5-Dihydro-7-oxo-8-phenyl-7H—thieno[2,3-a]quinolizin-10-yl)carbonyl]-3-methoxypyrrolidine.
V = 3-Methoxy-1-[(7-oxo-8-phenyl-7H—thieno[2,3-a]quinolizin-10-yl)carbonyl]azetidine.
W = (R)—1-[(10-Chloro-4-oxo-3-phenyl-4H—benzo[a]quinolizin-1-yl)carbonyl]-2-pyrrolidinemethanol.
X = (S)—1-[(10-Chloro-4-oxo-3-phenyl-4H—benzo[a]quinolizin-1-yl)carbonyl]-2-(methoxymethyl)pyrrolidine.
Y = (R)—1-[(10-Chloro-4-oxo-3-phenyl-4H—benzo[a]quinolizin-1-yl)carbonyl]-2-(methoxymethyl)pyrrolidine.

The compounds of formula I and the pharmaceutically acceptable acid addition salts of compounds of formula I which have a basic substituent can be used as medicaments, for example, in the form of pharmaceutical preparations. The pharmaceutical preparations can be administered orally, for example, in the form of tablets, coated tablets, dragees, hard and soft gelatin capsules, solutions, emulsions or suspension. However, the administration can also be carried out rectally, for example, in the form of suppositories, or parenterally, for example, in the form of injection solutions, For the preparation of pharmaceutical preparations, compounds of formula I, the invention can be processed with pharmaceutically inert, inorganic or organic carriers. Lactose, maize starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active substance no carriers are, however, required in the case of soft gelatin capsules. Suitable carriers for the preparation of solutions and syrups are, for example, water, polyols, saccharose, invert sugar, glucose and the like. Suitable carriers for injection solutions are, for example, water, alcohols, polyols, glycerine, vegetable oils and the like. Suitable carriers for suppositories are, for example, natural or hardened oils, waxes, fats, semi-liquid or liquid polyols and the like.

The pharmaceutical preparations can also contain preserving agents, solubilizing agents, stabilizing agents, wetting agents, emulsifying agents, sweetening agents, coloring agents, flavouring agents, salts for varying the osmotic pressure, buffers, coating agents or antioxidants. They can also contain other therapeutically valuable substances. Medicaments containing a compound of formula I of the invention and a therapeutically inert carrier as well as a process for their preparation which comprises bringing a product in accordance with the invention and, if desired, one or more other therapeutically valuable substances into a galenical form for administration also form part of the invention.

As mentioned earlier, the products in accordance with the invention can be used in the control or prevention of illnesses, especially in the control of convulsions and anxiety states, as well as for the preparation of medicaments with muscle relaxant, sedative-hypnotic, anticonvulsive and/or anxiolytic properties. The dosage can vary within wide limits and is, of course, fitted to the individual requirements in each particular case. In the case of oral administration, the daily dosage lies in a range of from about 1 mg to about 100 mg.

The following Examples serve to illustrate the invention in more detail. All temperatures given in degrees Celsius, unless otherwise stated.

EXAMPLE 1

(aa) Method A: 29.4 g of α-bromophenylacetyl chloride were added dropwise while stirring to a solution of 23.3 g of 4,5-dihydrothieno[2,3-c]pyridine-7(6H)-thione in 630 ml of chloroform, whereby care was taken that the temperature did not exceed 25°. After 30 minutes, the mixture was treated with 25.45 g of triethylamine and stirred for an additional 3 hours. The mixture was diluted with water, the organic phase was separated, washed with saturated aqueous sodium chloride solution, dried over magnesium sulfate, evaporated and the residue was chromatographed on silica gel (elution agent toluene/ethanol 95:5). There was obtained 5,6-dihydro-3-hydroxy-2-phenylthiazolo[3,2-a]thieno[2,3-c]pyridinium hydroxide (internal salt) of m.p. 225° (dec.) (from dioxane/acetonitrile).

Method B: 28.6 g of 1-phenyl-2,2-dicyano-oxirane are added while stirring to a solution of 26.35 g of 4,5-dihydrothieno[2,3-c]pyridine-7-(6H)-thione in 140 ml of dimethylformamide, whereby the solution immediately becomes deep red in color. After 16 hours, the crystalline precipitate was removed by filtration under suction and washed with ethyl acetate. There was obtained 5,6-dihydro-3-hydroxy-2-phenylthiazolo[3,2-a]thieno[2,3-c]pyridinium hydroxide (internal salt) of m.p. 208°–209°.

In an analogous manner, (ab) from 4,5-dihydrothieno[2,3-c]pyridine-7(6H)-thione and 1-(o-chlorophenyl)-2,2-dicyano-oxirane there was obtained 5,6-dihydro-3-hydroxy-2-(o-chlorophenyl)-thiazolo[3,2-a]thieno[2,3-c]pyridinium hydroxide (internal salt) of m.p. 174°–175° (from dioxane/acetonitrile);

(ac) from 4,5-dihydrothieno[2,3-c]pyridine-7(6H)-thione and 1-(m-chlorophenyl)-2,2-dicyano-oxirane there was obtained 5,6-dihydro-3-hydroxy-2-(m-chlorophenyl)-thiazolo[3,2-a]thieno[2,3-c]pyridinium hydroxide (internal salt) of m.p. 179°–181°;

(ad) from 4,5-dihydrothieno[2,3-c]pyridine-7(6H)-thione and 1-(p-chlorophenyl)-2,2-dicyano-oxirane there was obtained 5,6-dihydro-3-hydroxy-2-(p-chlorophenyl)-thiazolo[3,2-a]thieno[2,3-c]pyridinium hydroxide (internal salt) of m.p. 215° (dec.);

(ae) from 4,5-dihydrothieno[2,3-c]pyridine-7(6H)-thione and 1-(m-fluorophenyl)-2,2-dicyano-oxirane there is obtained 5,6-dihydro-3-hydroxy-2-(m-fluorophenyl)-thiazolo[3,2-a]thieno[2,3-c]pyridinium hydroxide (internal salt);

(af) from 6,7-dihydrothieno[3,2-c]pyridine-7(6H)-thione and 1-phenyl-2,2-dicyano-oxirane there was obtained 5,6-dihydro-3-hydroxy-2-phenylthiazolo[3,2-a]thieno[3,2-c]pyridinium hydroxide (internal salt) of m.p. 198°-202° (dec.);

(ag) from piperidine-2-thione and 1-(p-chlorophenyl)-2,2-dicyano oxirane there was obtained 5,6,7,8-tetrahydro-3-hydroxy-2-(p-chlorophenyl)-thiazolo[3,2-a]pyridinium hydroxide (internal salt) as an amorphous solid.

(ba) A suspension of 31.65 g of 5,6-dihydro-3-hydroxy-2-phenylthiazolo[3,2-a]thieno[2,3-c]pyridinium hydroxide (internal salt) in 770 ml of toluene was treated with 10.94 g of methyl propiolate, the mixture was heated under reflux until the reaction has finished, the reaction mixture was evaporated in vacuo and the residue was chromatographed on silica gel with toluene/ethyl acetate (9:1). There was obtained methyl 4,5-dihydro-7-oxo-8-phenyl-7H-thieno[2,3-a]quinolizine-10-carboxylate as yellow crystals of m.p. 116° (from ethyl acetate).

In an analogous manner, (bb) from 5,6-dihydro-3-hydroxy-2-phenyl-thiazolo[3,2-a]thieno[2,3-c]pyridinium hydroxide (internal salt) and ethyl propiolate there was obtained ethyl 4,5-dihydro-7-oxo-8-phenyl-7H-thieno[2,3-a]quinolizine-10-carboxylate of m.p. 126°-127° (from ethanol);

(bc) from 5,6-dihydro-3-hydroxy-2-(o-chlorophenyl)-thiazolo[3,2-a]thieno[2,3-c]pyridinium hydroxide (internal salt) and methyl propiolate there was obtained methyl 8-(o-chlorophenyl)-4,5-dihydro-7-oxo-7H-thieno[2,3-a]quinolizine-10-carboxylate of m.p. 142.5°-143.5° (from ethyl acetate);

(bd) from 5,6-dihydro-3-hydroxy-2-(m-chlorophenyl)thiazolo[3,2-a]thieno[2,3-c]pyridinium hydroxide (internal salt) and methyl propiolate there was obtained methyl 8-(m-chlorophenyl)-4,5-dihydro-7-oxo-7H-thieno[2,3-a]quinolizine-10-carboxylate of m.p. 133°-134° (from acetonitrile);

(be) from 5,6-dihydro-3-hydroxy-2-(p-chlorophenyl)-thiazolo[3,2-a]thieno[2,3-c]pyridinium hydroxide (internal salt) and methyl propiolate there was obtained methyl 8-(p-chlorophenyl)-4,5-dihydro-7-oxo-7H-thieno[2,3-a]quinolizine-10-carboxylate of m.p. 174°-175.5° (from ethyl acetate).

(bf) from 5,6-dihydro-3-hydroxy-2-(m-fluorophenyl)-thiazolo[3,2-a]thieno[2,3-c]pyridinium hydroxide (internal salt) and methyl propiolate there was obtained methyl 8-(m-fluorophenyl)-4,5-dihydro-7-oxo-7H-thieno[2,3-a]quinolizine-10-carboxylate of m.p. 132°-134° (from ethyl acetate/diisopropyl ether);

(bg) from 5,6-dihydro-3-hydroxy-2-phenyl-thiazolo[3,2-a]thieno[3,2-c]pyridinium hydroxide (internal salt) and methyl propiolate there was obtained methyl 4,5-dihydro-7-oxo-8-phenyl-7H-thieno[3,2-a]quinolizine-10-carboxylate of m.p. 172.5°-177° (from ethyl acetate).

(bh) from 5,6,7,8-tetrahydro-3-hydroxy-2-(p-chlorophenyl)-thiazolo[3,2-a]pyridinium hydroxide (internal salt) and methyl propiolate there was obtained methyl 3-(p-chlorophenyl)-6,7,8,9-tetrahydro-4-oxo-4H-quinolizine-1-carboxylate of m.p. 132°-133°.

EXAMPLE 2

(aa) 2.53 g of methyl 4,5-dihydro-7-oxo-8-phenyl-7H-thieno[2,3-a]quinolizine-10-carboxylate were added to a solution of 0.4 g of sodium hydroxide in 70 ml of methanol and the mixture was heated under reflux until the saponification has finished. After evaporation of the solvent in vacuo the residue was taken up in water and extracted with chloroform. The aqueous phase was treated with active carbon and then acidified with 1N hydrochloric acid, whereby pure 4,5-dihydro-7-oxo-8-phenyl-7H-thieno[2,3-a]quinolizine-10-carboxylic acid of m.p. 210°-210.5° (dec.) precipitated.

In an analogous manner, (ab) from methyl 8-(m-fluorophenyl)-4,5-dihydro-7-oxo-7H-thieno[2,3-a]quinolizine-10-carboxylate there was obtained 8-(m-fluorophenyl)-4,5-dihydro-7-oxo-7H-thieno[2,3-a]quinolizine-10-carboxylate acid of m.p. 233°-235°;

(ac) from methyl 4,5-dihydro-7-oxo-8-phenyl-7H-thieno[3,2-a]quinolizine-10-carboxylate there was obtained 4,5-dihydro-7-oxo-8-phenyl-7H-thieno[3,2-a]quinolizine-10-carboxylic acid of m.p. 244°-247° (dec).

(ba) 2.5 g of 4,5-dihydro-7-oxo-8-phenyl-7H-thieno[2,3-a]quinolizine-10-carboxylic acid was added portionwise while stirring to 7.5 ml of thionyl chloride, the mixture was stirred at room temperature for 1 hour, the excess thionyl chloride was removed in vacuo and the residue was dissolved in 25 ml of toluene, 1 ml of triethylamine was added thereto while stirring and the mixture was subsequently treated with 0.9 ml of 2-dimethylaminoethylamine. The reaction mixture was stirred at room temperature for 2 hours, then treated with saturated aqueous sodium bicarbonate solution and extracted three times with methylene chloride. The organic phase was dried over sodium sulfate and evaporated. The hydrochloride was prepared from the material obtained by means of methanolic hydrochloric acid. By recrystallization from methanol/diethyl ether there was obtained N-[2-(dimethylamino)ethyl]-4,5-dihydro-7-oxo-8-phenyl-7H-thieno[2,3-a]quinolizine-10-carboxamide hydrochloride as yellow crystals of m.p. 260°-261°.

In an analogous manner, (bb) from 4,5-dihydro-7-oxo-8-phenyl-7H-thieno[2,3-a]quinolizine-10-carboxylic acid and 2-dimethylaminoethanol there was obtained 2-(dimethylamino)ethyl 4,5-dihydro-7-oxo-8-phenyl-7H-thieno[2,3-a]quinolizine-10-carboxylate of m.p. 206°-207° (from ethanol/diethyl ether);

(bc) from 4,5-dihydro-7-oxo-8-phenyl-7H-thieno[2,3-a]quinolizine-10-carboxylic acid and ethyl piperidine-4-carboxylate there was obtained ethyl 1-[(4,5-dihydro-7-oxo-8-phenyl-7H-thieno[2,3-a]quinolizin-10-yl]carbonyl]-1-piperidinecarboxylate as an amorphous material;

(bd) from 4,5-dihydro-7-oxo-8-phenyl-7H-thieno[2,3-a]quinolizine-10-carboxylic acid and 1-acetylpiperazine there was obtained 1-acetyl-4-[[4,5-dihydro-7-oxo-8-phenyl-7H-thieno[2,3-a]quinolizin-10-yl]carbonyl-piperazine of m.p. 226°-227° (from dioxane);

(be) from 4,5-dihydro-7-oxo-8-phenyl-7H-thieno[2,3-a]quinolizine-10-carboxylic acid and 1-methylpiperazine there was obtained 1-[(4,5-dihydro-7-oxo-8-phenyl-7H-thieno[2,3-a]quinolizin-10-yl)carbonyl]-4-methylpiperazine hydrochloride of m.p. 280° (from methanol/diethyl ether);

(bf) from 4,5-dihydro-7-oxo-8-phenyl-7H-thieno[2,3-a]quinolizine-10-carboxylic acid and morpholine there was obtained 4-[(4,5-dihydro-7-oxo-8-phenyl-7H-thieno[2,3-a]quinolizin-10-yl)carbonyl]-morpholine of m.p. 212°–214° (from dioxane/diethyl ether):

(bg) from 4,5-dihydro-7-oxo-8-phenyl-7H-thieno[2,3-a]quinolizine-10-carboxylic acid and 4-hydroxypiperidine there was obtained 1-[[4,5-dihydro-8-phenyl-7-oxo-7H-thieno[2,3-a]quinolizin-10-yl]carbonyl]-4-piperidinol of m.p. 140°–142° (from acetonitrile/diethyl ether);

(bh) from 4,5-dihydro-7-oxo-8-phenyl-7H-thieno[2,3-a]quinolizine-10-carboxylic acid and piperazine there was obtained 1-[(4,5-dihydro-7-oxo-8-phenyl-7H-thieno[2,3-a]quinolizin-10-yl)carbonyl]-piperazine hydrochloride of m.p. 260°–271° (from ethanol/diethyl ether);

(bi) from 4,5-dihydro-7-oxo-8-phenyl-7H-thieno[2,3-a]quinolizine-10-carboxylic acid and 1,1-diethylaminoethylamine there was obtained N-[2-(diethylamino)ethyl]-4,5-dihydro-7-oxo-8-phenyl-7H-thieno[2,3-a]quinolizine-10-carboxamide hydrochloride as an amorphous material;

(bj) from 4,5-dihydro-7-oxo-8-phenyl-7H-thieno[2,3-a]quinolizine-10-carboxylic acid and thiomorpholine there was obtained 4-[(4,5-dihydro-7-oxo-8-phenyl-7H-thieno[2,3-a]quinolizin-10-yl)carbonyl]-tetrahydro-1H-1,4-thiazine of m.p. 224°–226° (from ethanol/diethyl ether);

(bk) from 4,5-dihydro-7-oxo-8-phenyl-7H-thieno[2,3-a]quinolizine-10-carboxylic acid and 2-methylaminoethanol there was obtained 4,5-dihydro-N-(2-hydroxyethyl)-N-methyl-7-oxo-8-phenyl-7H-thieno[2,3-a]quinolizine-10-carboxamide of m.p. 208°–210° (from acetonitrile);

(bl) from 4,5-dihydro-7-oxo-8-phenyl-7H-thieno[2,3-a]quinolizine-10-carboxylic acid and ethyl glycinate there was obtained ethyl N-[[4,5-dihydro-7-oxo-8-phenyl-7H-thieno[2,3-a]quinolizin-10-yl]carbonyl]glycinate of m.p. 211°–213° (from ethyl acetate/diethyl ether):

(bm) from 4,5-dihydro-7-oxo-8-phenyl-7H-thieno[2,3-a]quinolizine-10-carboxylic acid and 3-(dimethylamino-1-propylamine there was obtained N-[3-dimethylamino)propyl]-4,5-di-hydro-8-phenyl-7H-thieno[2,3-a]quinolizine-10-carboxamide hydrochloride of m.p. 261°–262° (from methanol/diethyl ether):

(bn) from 4,5-dihydro-7-oxo-8-phenyl-7H-thieno[2,3-a]quinolizine-10-carboxylic acid and 2-aminoethanol there was obtained 4,5-dihydro-N-(2-hydroxyethyl)-8-phenyl-7-oxo-7H-thieno[2,3-a]quinolizine-10-carboxamide of m.p. 228°–230° (from chloroform/hexane):

(bo) from 4,5-dihydro-7-oxo-8-phenyl-7H-thieno[2,3-a]quinolizine-10-carboxylic acid and concentrated aqueous ammonia solution there was obtained 4,5-dihydro-7-oxo-8-phenyl-7H-thieno[2,3-a]quinolizine-10-carboxamide of m.p. 281°–281.5° (from ethanol):

(bp) from 4,5-dihydro-7-oxo-8-(m-fluorophenyl)-7H-thieno[2,3-a]quinolizine-10-carboxylic acid and morpholine there was obtained 4-[[8-(m-fluorophenyl)-4,5-dihydro-7-oxo-7H-thieno[2,3-a]quinolizin-10-yl]carbonyl]morpholine of m.p. 213°–214° (from methanol):

(bq) from 4,5-dihydro-7-oxo-8-phenyl-7H-thieno[3,2-a]quinolizine-10-carboxylic acid and 2-aminoethanol there was obtained 4,5-dihydro-N-(2-hydroxyethyl)-7-oxo-8-phenyl-7H-thieno[3,2-a]quinolizine-10-carboxamide of m.p. 202°–204° (from chloroform/hexane):

(br) from 2-chloro-4,5-dihydro-7-oxo-8-phenyl-7H-thieno[2,3-a]quinolizine-10-carboxylic acid and morpholine there was obtained 4-[(2-chloro-4,5-dihydro-7-oxo-8-phenyl-7H-thieno[2,3-a]quinolizin-10-yl)carbonyl]morpholine of m.p. 190°–192°:

(bs) from 4,5-dihydro-7-oxo-8-phenyl-7H-thieno[2,3-a]quinolizine-10-carboxylic acid and cis-2,6-dimethylmorpholine there was obtained cis-4-[(4,5-dihydro-7-oxo-8-phenyl-7H-thieno[2,3-a]quinolizine-10-yl)carbonyl]-2,6-dimethylmorpholine of m.p. 221°–223°.

EXAMPLE 3

(a) 7.1 ml of tri-n-butylamine and 6.1 ml of isopropanol were added to a suspension of 2.0 g of 4,5-dihydro-7-oxo-8-phenyl-7H-thieno[2,3-a]quinolizine-10-carboxylic acid and 3.8 g of N-methyl-2-chloropyridinium iodide in 12.5 ml of methylene chloride, the reaction mixture was stirred under reflux for 24 hours, evaporated in vacuo and the residue was chromatographed on silica gel with toluene/ethyl acetate (9:1). After crystallization from methanol, there was obtained pure isopropyl 4,5-dihydro-7-oxo-8-phenyl-7H-thieno[2,3-a]quinolizine-10-carboxylate of m.p. 165.5°–166°.

In an analogous manner, (b) from 4,5-dihydro-7-oxo-8-phenyl-7H-thieno[2,3-a]quinolizine-10-carboxylic acid, N-methyl-2-chloropyridinium iodide, tri-n-butylamine and benzyl alcohol there was obtained benzyl, 4,5-dihydro-8-phenyl-7-oxo-7H-thieno[2,3-a]quinolizine-10-carboxylate of m.p. 159°–160° (from acetonitrile);

(c) from 4,5-dihydro-7-oxo-8-phenyl-7H-thieno[2,3-a]quinolizine-10-carboxylic acid, N-methyl-2-chloropyridinium iodide, tri-n-butylamine and diethylamine there was obtained N,N-diethyl-4,5-dihydro-7-oxo-8-phenyl-7H-thieno[2,3-a]quinolizine-10-carboxamide of m.p. 175°–175.5° (from isopropanol);

(d) from 4,5-dihydro-7-oxo-8-phenyl-7H-thieno[2,3-a]quinolizine-10-carboxylic acid, N-methyl-2-chloropyridinium iodide, tri-n-butylamine and cyclohexylamine there was obtained N-cyclohexyl-4,5-dihydro-7-oxo-8-phenyl-7H-thieno[2,3-a]quinolizine-10-carboxamide of m.p. 284°–284.5° (from dioxane).

EXAMPLE 4

(a) 10.82 g of 4,5-dihydro-7-oxo-8-phenyl-7H-thieno[2,3-a]quinolizine-10-carboxylic acid were added to 67 ml of thionyl chloride, the mixture was stirred at room temperature for 1 hour, the excess thionyl chloride was removed by distillation in vacuo, the acid chloride obtained was taken up in 67 ml of tetrahydrofuran and this solution was added dropwise within about 30 minutes to a suspension of 2.55 g of sodium borohydride in 67 ml of dimethylformamide. After 3 hours, the mixture was acidified with 2N hydrochloric acid while cooling and then heated to boiling for a short time. The mixture was made alkaline with 2N sodium hydroxide solution and extracted with chloroform/methanol (9:1). The organic phase was washed with saturated aqueous sodium chloride solution, dried over magnesium sulfate and evaporated in vacuo. After recrystallization from methanol, there was obtained pure 4,5-dihydro-10-(hydroxymethyl)-8-phenyl-7H-thieno[2,3-a]quinolizin-7-one of m.p. 199°–200°.

In an analogous manner, (b) from 10-chloro-6,7-dihydro-4-oxo-3-phenyl-4H-benzo[a]quinolizine-1-carboxylic acid there was obtained 6,7-dihydro-1-(hydroxymethyl)-3-phenyl-10-chloro-4H-benzo[a]quinolizin-4-one of m.p. 248°–249°;

(c) from 6,7-dihydro-4-oxo-3-phenyl-4H-benzo[a]quinolizine-1-carboxylic acid there was obtained 6,7-dihydro-1-(hydroxymethyl)-3-phenyl-4H-benzo[a]quinolizin-4-one of m.p. 175°–177°;

(d) from 1-[(10-chloro-6,7-dihydro-4-oxo-3-phenyl-4H-benzo[a]quinolizin-1-yl)carbonyl]-4-piperidinecarboxylic acid there was obtained 1-[(10-chloro-6,7-dihydro-4-oxo-3-phenyl-4H-benzo[a]quinolizin-1-yl)carbonyl]-4-piperidinemethanol of m.p. 217°–218°;

(e) from 7-oxo-8-phenyl-7H-thieno[2,3-a]quinolizine-10-carboxylic acid there was obtained 10-(hydroxymethyl)-8-phenyl-7H-thieno[2,3-a]quinolizin-7-one of m.p. 209°–216°.

EXAMPLE 5

(a) A suspension of 1.55 g of 4,5-dihydro-10-(hydroxymethyl)-8-phenyl-7H-thieno[2,3-a]quinolizin-7-one in 6.7 ml of pyridine was treated with 3.35 ml of acetic anhydride while stirring, whereby a clear solution was obtained after about 15 minutes. After stirring overnight, the precipitated yellow crystals were removed by filtration under suction and washed with ether. The filtrate was evaporated in vacuo and the residue together with the above yellow crystals were recrystallized from methanol. There was obtained pure (4,5-dihydro-7-oxo-8-phenyl-thieno[2,3-a]-quinolizin-1-yl)methyl acetate of m.p. 145°–146°.

In an analogous manner, (b) from 6,7-dihydro-1-(hydroxymethyl)-3-phenyl-10-chloro-4H-benzo[a]quinolizin-4-one there was obtained (10-chloro-6,7-dihydro-4-oxo-3-phenyl-4H-benzo[a]quinolizin-1-yl)methyl acetate of m.p. 124°–125°.

(c) from (S)-1-[(10-chloro-6,7-dihydro-4-oxo-3-phenyl-4H-benzo[a]quinolizin-1-yl)carbonyl]-2-pyrrolidinemethanol there was obtained [(S)-1-[(10-chloro-6,7-dihydro-4-oxo-3-phenyl-4H-benzo[a]quinolizin-1-yl)carbonyl]-2-pyrrolidinyl]methyl acetate of m.p. 134°–136°;

(d) from 1-[(10-chloro-6,7-dihydro-4-oxo-3-phenyl-4H-benzo[a]quinolizin-1-yl)carbonyl]-4-piperidinol there was obtained 1-[(10-chloro-6,7-dihydro-4-oxo-3-phenyl-4H-benzo[a]quinolizin-1-yl)carbonyl]-4-piperidinyl acetate of m.p. 179°–181°.

EXAMPLE 6

6.8 g of 4,5-dihydro-10-(hydroxymethyl)-8-phenyl-7H-thieno[2,3-a]quinolizin-7-one were suspended in 220 ml of methylene chloride, the suspension was treated with 68 g of manganese dioxide and the mixture was stirred at room temperature overnight. The inorganic material was removed by filtration and the filtrate was evporated. The residue was crystallized from dioxane, whereby pure 4,5-dihydro-7-oxo-8-phenyl-7H-thieno[2,3-a]quinolizine-10-carboxaldehyde of m.p. 212°–212.5° was obtained.

EXAMPLE 7

(a) A suspension of 275 mg of sodium hydride in mineral oil (55 percent) was washed twice with n-pentane. There were then added thereto 6.3 ml of dimethylformamide and subsequently dropwise within 15 minutes a solution of 1.3 g of 4,5-dihydro-10-(hydroxymethyl)-8-phenyl-7H-thieno[2,3-a]quinolizin-7-one in 20 ml of tetrahydrofuran. As soon as the evolution of hydrogen finished, 0.47 ml of methyl iodide was added thereto. The mixture was stirred at room temperature for 1 hour and then treated with water while cooling. The separated yellow precipitate was washed well with water. After recrystallization from acetonitrile, there was obtained 4,5-dihydro-10-(methoxymethyl)-8-phenyl-7H-thieno[2,3-a]quinolizin-7-one of m.p. 119.5°–120.5°.

In an analogous manner.

(b) from 4,5-dihydro-10-(hydroxymethyl)-8-phenyl-7H-thieno[2,3-a]quinolizin-7-one and ethyl iodide there was obtained 4,5-dihydro-10-(ethoxymethyl)-8-phenyl-7H-thieno[2,3-a]quinolizin-7-one of m.p. 140°–141° (from ethanol);

(c) from 10-(hydroxymethyl)-8-phenyl-7H-thieno[2,3-a]quinolizin-7-one and 2-chloroethyl methyl ether in the presence of about one equivalent of potassium iodide there was obtained 10-[(2-methoxyethoxy)-methyl]-8-phenyl-7H-thieno[2,3-a]quinolizin-7-one of m.p. 106°–107°;

(d) from 6,7-dihydro-1-(hydroxymethyl)-3-phenyl-10-chloro-4H-benzo[a]quinolizin-4-one and ethyl iodide there was obtained 10-chloro-6,7-dihydro-1-(ethoxymethyl)-3-phenyl-4H-benzo[a]quinolizin-4-one of m.p. 121°–123°.

EXAMPLE 8

A few drops of triethylamine and three 0.24 ml portions of ethyl isocyanate were added to a suspension of 1.02 g of 4,5-dihydro-10-(hydroxymethyl)-8-phenyl-7H-thieno[2,3-a]quinolizin-7-one in 11.5 ml of toluene, whereby the mixture was stirred at 85° for about 2 hours between each of the additions. After the reaction was finished, the mixture is evaporated in vacuo. By recrystallization of the residue from ethanol, there was obtained pure (4,5-dihydro-7-oxo-8-phenyl-7H-thieno[2,3-a]quinolizin-10-yl)methyl-ethylcarbamate of m.p. 136°–137°.

EXAMPLE 9

A solution of 0.92 ml of trichloroacetyl isocyanate in 14 ml of methylene chloride was added dropwise within 15 minutes to a suspension of 2.17 g of 4,5-dihydro-10-(hydroxymethyl)-8-phenyl-7H-thieno[2,3-a]quinolizin-7-one in 56 ml of methylene chloride. After 1.5 hours, the mixture was evaporated in vacuo. The residue was suspended in ether, whereupon the suspension was suction filtered and the filter residue was rinsed well with ether. After drying for a short time, the crystals obtained were suspended in 60 ml of tetrahydrofuran/methanol (1:1), whereupon the suspension was treated with 1.91 g of potassium carbonate in 14 ml of water and stirred at room temperature overnight. After removing the product by filtration under suction, washing with water and recrystallization from dioxane there was obtained pure (4,5-dihydro-7-oxo-8-phenyl-7H-thieno[2,3-a]quinolizin-10-yl)methylcarbamate of m.p. 237°–238°.

EXAMPLE 10

(a) 0.96 ml of N,N-dimethylformamide di-t-butyl acetal was added dropwise within 20 minutes to a boiling solution of 0.34 g of 4,5-dihydro-7-oxo-8-(m-fluorophenyl)-7H-thieno[2,3-a]quinolizine-10-carboxylic acid in 5 ml of toluene. The mixture was heated under reflux for an additional 30 minutes, left to stand at room temperature overnight and then washed once with water, twice with saturated aqueous sodium bicarbonate solution and once with saturated aqueous sodium chloride solution. The organic phase was dried over sodium sulfate and evaporated in vacuo. The residue was recrystallized from ethyl acetate and there was obtained tert-butyl 8-(m-fluorophenyl)-4,5-dihydro-7-oxo-7H-thieno[2,3-a]quinolizine-10-carboxylate of m.p. 135°–137°.

In an analogous manner, (b) from 4,5-dihydro-7-oxo-8-phenyl-7H-thieno[2,3-a]quinolizine-10-carboxylic acid there was obtained tert-butyl 4,5-dihydro-7-oxo-8-phenyl-7H-thieno[2,3-a]quinolizine-10-carboxylate of m.p. 166.5°–167.5° (from cyclohexane);

(c) from 4,5-dihydro-7-oxo-8-phenyl-7H-thieno[3,2-a]quinolizine-10-carboxylic acid there was obtained tert-butyl 4,5-dihydro-7-oxo-8-phenyl-7H-thieno[3,2-a]quinolizine-10-carboxylate of m.p. 200°–202° (from ethyl acetate);

(d) from 10-chloro-6,7-dihydro-4-oxo-3-phenyl-4H-benzo[a]quinolizine-1-carboxylic acid there is obtained tert-butyl 2-chloro-5,6-dihydro-8-oxo-9-phenyl-8H-benzo[a]quinolizine-1-carboxylate.

EXAMPLE 11

2.0 g of 4,5-dihydro-7-oxo-8-phenyl-7H-thieno[2,3-a]quinolizine-10-carboxylic acid and 6.2 ml of thionyl chloride were stirred at room temperature for 2 hours, whereupon the excess thionyl chloride was removed by distillation in vacuo. The residue, dried in a high vacuum, was dissolved in 20 ml of tetrahydrofuran. This solution was slowly added dropwise at −78° while stirring to a methylmagnesium bromide solution prepared from 168 mg of magnesium and 0.9 ml of a 65.5 percent solution of methyl bromide in tetrahydrofuran. After the reaction mixture has warmed to room temperature, it was stirred at this temperature overnight, then acidified with 0.1N hydrochloric acid while cooling and extracted with ether. The ether phase was washed with 10 percent aqueous potassium bicarbonate solution and saturated aqueous sodium chloride solution. It was dried over magnesium sulfate, evaporated in vacuo and the residue was chromatographed on silica gel with cyclohexane/dioxane (2:1). By recrystallization from isopropanol, there was obtained pure 10-acetyl-4,5-dihydro-8-phenyl-7H-thieno[2,3-a]quinolizin-7-one of m.p. 149°–149.5°.

EXAMPLE 12

A solution of 0.303 g of 5,6-dihydro-3-hydroxy-2-(m-fluorophenyl)-thiazolo-[3,2-a]thieno[2,3-c]pyridinium hydroxide (internal salt) and 0.145 ml of 3-butyn-2-one in 5 ml of toluene was heated under reflux for 1 hour. The solvent is evaporated in vacuo and the residue is chromatographed over silica gel with toluene/ethyl acetate (1:1). After recrystallization from ethanol, there was obtained 10-acetyl-4,5-dihydro-8-(m-fluorophenyl)-7H-thieno[2,3-a]quinolizin-7-one of m.p. 109°–110°.

EXAMPLE 13

(a) A solution of 0.1 g of ethyl-1-[[4,5-dihydro-7-oxo-8-phenyl-7H-thieno[2,3-a]quinolizin-10-yl]carbonyl]-4-piperidinecarboxylate and 0.016 g of sodium hydroxide in 2 ml of methanol was heated under reflux for 3 hours. the mixture was then evaporated in vacuo, the residue was taken up in water and extracted with chloroform. The aqueous phase was made acid with 3N hydrochloric acid and extracted with ethyl acetate. The organic phase was dried over sodium sulfate and evaporated in vacuo, and there was obtained crude 1-[[4,5-dihydro-7-oxo-8-phenyl-7H-thieno[2,3-a]-quinolizin-10-yl]carbonyl-4-piperidinecarboxylic acid.

(b) 3 g of 1-[[4,5-dihydro-7-oxo-8-phenyl-7H-thieno[2,3-a]quinolizine-10-yl]carbonyl]-4-piperidinecarboxylic acid were added portionwise to 9 ml of thionyl chloride while stirring. The mixture was stirred at room temperature for 1 hour, whereupon the excess thionyl chloride was removed in vacuo. The residue was dissolved in 30 ml of toluene. 4.8 ml of triethylamine was added thereto while stirring and the mixture was subsequently treated with 4.13 ml of a 15 percent solution of ethylamine in toluene. The reaction mixture was stirred at room temperature for 1.5 hours, then treated with water and extracted three times with methylene chloride. The organic phase was dried over sodium sulfate and evaporated. The residue was chromatographed on silica gel and the product obtained was recrystallized from methylene chloride/diethyl ethyl. There was obtained N-ethyl-1-[[4,5-dihydro-7-oxo-8-phenyl-7H-thieno[2,3-a]quinolizin-10-yl]carbonyl]-4-piperidinecarboxamide of m.p. 134°–135°.

EXAMPLE 14

0.94 g of diethyl azodicarboxylate and 0.71 g of triphenylphosphine were added to a solution of 1.0 g of 4,5-dihydro-N-(2-hydroxyethyl)-8-phenyl-7-oxo-7H-thieno[2,3-a]quinolizine-10-carboxamide in 27 ml of tetrahydrofuran, whereupon the reaction mixture was stirred for 24 hours. The mixture was then evaporated in vacuo, the residue was treated with water and extracted three times with methylene chloride. The organic phase was dried over sodium sulfate and evaporated in vacuo. The residue was chromatographed on silica gel with acetonitrile/diethyl ether (2:3). By recrystallization from dioxane, there was obtained 4,5-dihydro-10-(2-oxazolin-2-yl)-8-phenyl-7H-thieno[2,3-a]quinolizin-7-one of m.p. 211°–212°.

EXAMPLE 15

(a) 6.4 g of 5,6-dihydro-3-hydroxy-2-phenyl-thiazolo[3,2-a]thieno[2,3-c]pyridinium hydroxide (internal salt) were suspended in 225 ml of toluene, whereupon the suspension is treated with 1.75 ml of acrylonitrile and heated under reflux overnight. After cooling, the precipitated product was removed by filtration under suction and washed with toluene. Recrystallization from acetonitrile yielded pure 4,5,7,8,9,10-hexahydro-7-oxo-8-phenyl-8,10a-epithio-10aH-thieno[2,3-a]quinolizine-10-carbonitrile of m.p. 228°–229°.

(b) 2.35 g of 4,5,7,8,9,10-hexahydro-7-oxo-8-phenyl-8,10a-epithio-10aH-thieno[2,3-a]quinolizine-10-carbonitrile were added to a freshly prepared sodium methylate solution (prepared from 178 mg of sodium and 10 ml of methanol). The mixture was heated under reflux for 2 hours, whereby there initially resulted a clear solution from which a yellow product precipitated. After cooling, the precipitated 4,5-dihydro-7-oxo-8-phenyl-7H-thieno[2,3-a]quinolizinecarbonitrile was removed by filtration under suction, washed with methanol and recrystallized from ethanol/dioxane. The product has a m.p. of 189°–189.5°.

EXAMPLE 16

A solution of 1.5 g of 4,5-dihydro-7-oxo-8-phenyl-7H-thieno[2,3-a]quinolizine-10-carbonitrile in 15 ml of tetrahydrofuran was treated with 20 ml of a 1M BH₃/tetrahydrofuran solution and stirred at room temperature until the reaction was finished. The mixture was then acidified cautiously with 2N hydrochloric acid while cooling with ice, heated to boiling for a short time and made alkaline with 2N sodium hydroxide solution. The tetrahydrofuran was removed in vacuo and the aqueous residue was extracted with chloroform. The organic phase was washed with saturated sodium chloride solution, dried over magnesium sulfate and evaporated. The residue was chromatographed on silica gel with chloroform/methanol (19:1). After treatment with methanolic hydrochloric acid. there was obtained pure 10-(aminomethyl)-4,5-dihydro-8-phenyl-7H-thieno[2,3-a]quinolizin-7-one hydrochloride of m.p. 254°–255°.

EXAMPLE 17

(a) 4.27 g of 5,6-dihydro-3-hydroxy-2-phenyl-thiazolo[2,3-a]thieno[2,3-c]pyridinium hydroxide (internal salt) was suspended in 50 ml of toluene. The suspension was treated with 1.32 g of nitroethylene, stirred at room temperature, heated to 60° for a short time after 1 hour, evaporated in vacuo and the residue was chromatographed on silica gel with toluene/ethyl acetate (9:1). By crystallization from acetonitrile, there was obtained pure 4,5,9,10-tetrahydro-10-nitro-8-phenyl-8,10a-epithio-10aH-thieno[2,3-a]quinolizin-7(8H)-one of m.p. 192°–196°.

(b) 1.58 g of 4,5,9,10-tetrahydro-10-nitro-8-phenyl-8,10a-epithio-10aH-thieno[2,3-a]quinolizin-7(8H)-one were heated slowly together with 2 equivalents of sodium methylate in 30 ml of methanol. After the reaction ceases, the mixture was heated under reflux for an additional 2 hours, whereupon the solvent was removed by distillation and the residue was chromatographed on silica gel with toluene/acetone (9:1). There was obtained 4,5-dihydro-10-nitro-8-phenyl-7H-thieno[2,3-a]quinolizin-7-one of m.p. 186°–189° (from acetonitrile) and in a later fraction 10-amino-4,5-dihydro-8-phenyl-7H-thieno[2,3-a]quinolizin-7-one of m.p. 180.5°–181.5° (from toluene).

EXAMPLE 18

3.2 g of 4,5,9,10-tetrahydro-10-nitro-8-phenyl-8,10a-epithio-10aH-thieno[2,3-a]quinolizin-7(8H)-one was suspended in 300 ml of methanol. The suspension was treated while stirring with a solution of sodium methylate in methanol (prepared from 4.46 g of sodium and 5 ml of methanol) and subsequently with a solution of 14 g of sodium sulfide in 40 ml of methanol, whereby there results a dark solution which is held at 60° for 4 hours. After the methanol is removed by distillation in vacuo, the residue was taken up in water. The solution was extracted with chloroform and the organic phase was washed with saturated aqueous sodium chloride solution. The organic phase was dried over magnesium sulfate, evaporated in vacuo and the product was chromatographed on silica gel with toluene/acetone (9:1). There was obtained 10-amino-4,5-dihydro-8-phenyl-7H-thieno[2,3-a]quinolizin-7-one of m.p. 180.5°–181.5° (from toluene).

EXAMPLE 19

A solution of 0.78 g of 10-amino-4,5-dihydro-8-phenyl-7H-thieno[2,3-a]quinolizin-7-one in 16 ml of acetone was treated with 1.84 g of powdered potassium carbonate and 1.26 ml of ethyl chloroformate and the mixture was heated under reflux for 3 hours. The undissolved inorganic material removed by filtration under suction and washed with acetone. The filtrate was evaporated in vacuo. The residue was taken up in chloroform, washed with water and saturated aqueous sodium chloride solution, dried over magnesium sulfate, evaporated and the residue was chromatographed on silica gel with toluene/acetone (19:1). There was obtained 4,5-dihydro-7-oxo-8-phenyl-7H-thieno[2,3-a]quinolizine-10-di(ethylcarbamate) of m.p. 180.5°–181.5° (from ethanol) and in a later fraction 4,5-dihydro-7-oxo-8-phenyl-7H-thieno-[2,3-a]quinolizine-10-ethylcarbamate of m.p. 212°–213° (from toluene).

EXAMPLE 20

0.48 g of 4,5-dihydro-7-oxo-8-phenyl-7H-thieno[2,3-a]quinolizine-10-carboxylic acid was stirred at room temperature for 1 hour together with 1.5 ml of thionyl chloride, whereupon excess thionyl chloride was removed in vacuo. The yellow, crystalline acid chloride obtained was dried in a high vacuum overnight. This acid chloride was then dissolved in 1.5 ml of dioxane. The solution was treated with 0.3 ml of trimethylsilyl azide and stirred at 80° for 3 hours. 2.5 ml of ethanol were then added, whereupon the mixture was stirred at 85° for 4 hours. The reaction mixture was evaporated in vacuo and the residue remaining behind was chromatographed on silica gel with toluene/acetone (9:1). Crystallization from toluene yielded 4,5-dihydro-7-oxo-8-phenyl-7H-thieno[2,3-a]quinolizine-10-ethylcarbamate of m.p. 212°–213°.

EXAMPLE 21

The corresponding acid chloride was prepared from 161 g of 4,5-dihydro-7-oxo-8-phenyl-7H-thieno[2,3-a]quinolizine-10-carboxylic acid and 5 ml of thionyl chloride in analogy to the detail in Example 20. This acid chloride was dissolved in 10 ml of tetrahydrofuran, excess ethereal diazomethane solution was added dropwise thereto at 0°–5° and the reaction mixture was stirred at room temperature for 2 hours. The precipitated diazoketone was removed under suction, washed well with ether and suspended in 33 ml of methanol. The suspension was treated with 2 spatula tips of freshly prepared silver oxide and the mixture was heated under reflux for 3 hours, whereby all of the diazoketone passed into solution. After separating the silver oxide, the solution was evaporated and the residue was chromatographed on silica gel with toluene/ethyl acetate (9:1). Crystallization from methanol yielded pure methyl 4,5-dihydro-7-oxo-8-phenyl-7H-thieno[2,3-a]quinolizine-10-acetate of m.p. 147.5°–148°.

EXAMPLE 22

(a) 0.646 g of 4,5-dihydro-7-oxo-8-phenyl-7H-thieno[2,3-a]quinolizine-10-carboxylic acid was dissolved in 20 ml of tetrahydrofuran. The solution was treated at −15° with 0.4 ml of a 10M solution of borane/methyl sulfide in tetrahydrofuran, left to warm to room temperature and subsequently heated under reflux for 2 hours. After cooling to room temperature, the reaction mixture was treated with methanol and evaporated in vacuo. The mixture was heated to boiling in 2N hydrochloric acid for a short time and extracted with chloroform. The organic extracts was washed with saturated aqueous sodium bicarbonate solution, dried over magnesium sulfate and evaporated in vacuo. After recrystallization from ethyl acetate/diethyl ether there was obtained pure 4,5-dihydro-10-methyl-8-phenyl-7H-thieno-[2,3-a]quinolizin-7-one of m.p. 80.5°–81°.

In an analogous manner, (b) from 4,5-dihydro-7-oxo-8-phenyl-7H-thieno[3,2-a]quinolizine-10-carboxylic acid and borane/methyl sulfide there was obtained 4,5-dihydro-10-methyl-8-phenyl-7H-thieno[3,2-a]quinolizin-7-one of m.p. 130°–136°;

(c) from 10-chloro-6,7-dihydro-4-oxo-3-phenyl-4H-benzo[a]quinolizine-1-carboxylic acid and borane/methyl sulfide there was obtained 10-chloro-6,7-dihydro-1-methyl-3-phenyl-4H-benzo[a]quinolizin-4-one of m.p. 151°–153°.

EXAMPLE 23

2.85 g of 5,6-dihydro-3-hydroxy-2-phenyl-thiazolo[3,2-a]thieno[2,3-c]pyridinium hydroxide (internal salt) was heated under reflux overnight in 100 ml of xylene together with 1.45 ml of phenylvinyl sulfoxide, whereupon the reaction mixture was evaporated in vacuo and the residue obtained was chromatographed on silica gel with toluene/ethyl acetate (9:1). There was obtained 4,5-dihydro-8-phenyl-7H-thieno[2,3-a]quinolizin-7-one of m.p. 133°–134° (from ethyl acetate).

EXAMPLE 24

(a) A solution of 0.71 ml of 2-(diethylamino)ethylamine in 5 ml of diethyl ether was acidified with ethereal hydrochloric acid while cooling with ice. The solution was evaporated in vacuo, the hydrochloride obtained was dissolved in 5 ml of methanol and the solution was treated with 307.4 mg of 4,5-dihydro-7-oxo-8-phenyl-7H-thieno[2,3-quinolizine-10-carboxaldehyde and 62.8 mg of sodium cyanoborohydride, whereby a clear solution resulted after a short time. After stirring overnight, the mixture was evaporated in vacuo and the residue was heated in 2N hydrochloric acid for a short time. After cooling, the reaction solution was made alkaline with 2N sodium hydroxide solution and extracted three times with chloroform. The organic extract was washed with saturated aqueous sodium chloride solution, dried over magnesium sulfate and evaporated in vacuo. The residue was taken up in ethanol and the dihydrochloride was then precipitated with ethanolic hydrochloric acid. Recrystallization from acetic acid yielded 10-[[[2-(diethylamino)ethyl]amino]methyl]-4,5-dihydro-8-phenyl-7H-thieno[2,3-a]quinolizin-7-one dihydrochloride of m.p. 230°–231°.

In an analogous manner, (b) from 4,5-dihydro-7-oxo-8-phenyl-7H-thieno[2,3-a]quinolizine-10-carboxaldehyde and 2-aminoethanol hydrochloride there was obtained 4,5-dihydro-10-[[(2-hydroxyethyl)amino]methyl]-8-phenyl-7H-thieno[2,3-a]quinolizin-7-one hydrochloride of m.p. 229°–229.5° (from methanol);

(c) from 4,5-dihydro-7-oxo-8-phenyl-7H-thieno[2,3-a]quinolizine-10-carboxaldehyde and ethyl glycinate hydrochloride there was obtained ethyl N-[4,5-dihydro-7-oxo-8-phenyl-7H-thieno[2,3-a]quinolizin-10-yl)methyl]glycinate hydrochloride of m.p. 158.5°–160° (from dioxane);

(d) from 4,5-dihydro-7-oxo-8-phenyl-7H-thieno[2,3-a]quinolizine-10-carboxaldehyde and morpholine there was obtained 4,5-dihydro-10-(morpholinomethyl)-8-phenyl-7H-thieno[2,3-a]quinolizin-7-one hydrochloride of m.p. 220°–226° (from isopropanol).

EXAMPLE 25

1.8 g of methyl 4,5-dihydro-7-oxo-8-phenyl-7H-thieno[2,3-a]quinolizine-10-carboxylate are dissolved in 32 ml of chloroform, whereupon the solution was treated at 0° with 0.55 ml of bromine in 1 ml of chloroform and stirred at room temperature overnight. After washing with 2N sodium hydroxide solution and saturated sodium chloride solution, drying over magnesium sulfate and evaporation, the residue in toluene/ethyl acetate (4:1) was chromatographed on silica gel. There was obtained pure methyl 2-bromo-4,5-dihydro-7-oxo-8-phenyl-7H-thieno[2,3-a]quinolizine-10-carboxylate of m.p. 170.5°–171° (from isopropanol).

EXAMPLE 26

A solution of 1 g of 5,6-dihydro-3-hydroxy-2-phenyl-thiazolo[3,2a]thieno[3,2-c]pyridinium hydroxide (internal salt) and 0.23 g of 3-butyl-2-one in 10 ml of toluene was stirred at room temperature for 48 hours. The solution was evaporated in vacuo and the residue was chromatographed on silica gel with toluene/ethyl acetate (9:1). There was obtained pure 10-acetyl-4,5-dihydro-8-phenyl-7H-thieno-[3,2-a]quinolizin-7-one of m.p. 181°–182° (from ethyl acetate).

EXAMPLE 27

(a) A mixture of 20 g of 6,7-dihydro-4-methyl-thieno[3,2-c]pyridine and 19.8 g of methyl 2-methylenephenylacetate was heated under an argon atomosphere to 80° for 2 hours and subsequently to 110° for 48 hours. Methanol was added to the cooled reaction mixture and the product was left to crystallize out. There was obtained 4,5,8,9-tetrahydro-8-phenyl-7H-thieno[3,2-a]quinolizin-7-one of m.p. 159°–161°.

(b) A solution of 3 g of 4,5,8,9-tetrahydro-8-phenyl-7H-thieno[2,3-a]quinolizin-7-one in 30 ml of toluene was treated with 1.85 g of manganese dioxide and heated under reflux for 3 days. An additional 1 g of manganese dioxide was then added thereto and the mixture is heated under reflux overnight. It was then filtered and the filtrate was evaporated in vacuo. The residue was chromatographed on silica gel with acetonitrile. The product obtained was recrystallized from toluene. There was obtained 4,5-dihydro-8-phenyl-7H-thieno[3,2-a]quinolizin-7-one of m.p. 187°–189°.

EXAMPLE 28

(aa) Method A: 23.65 g of 3,4-dihydroisoquinoline-1(2H)-thione was dissolved in 750 ml of chloroform, whereupon the solution was treated at room temperature while cooling firstly with 54 g of α-bromophenylacetyl chloride and 90 minutes later with 53 ml of triethylamine and the mixture was stirred at room temperature overnight. The reaction mixture was washed with water, dried over magnesium sulfate and evaporated in vacuo. There was obtained 5,6-dihydro-3-hydroxy-2-phenylthiazolo[2,3-a]isoquinolinium hydroxide (internal salt) of m.p. 210° (dec.) (from acetonitrile/dioxane).

(ab) Method B: 2.96 g of 7-chloro-3,4-dihydroisoquinoline-1(2H)-thione and 3.7 g of 1-(p-chlorophenyl)-2,2-dicyanooxirane were stirred overnight in 60 ml of acetone. The separated red crystalline precipitate was removed by filtration under suction and recrystallized from dioxane. There was obtained 9-chloro-2-(p-chlorophenyl)-5,6-dihydro-3-hydroxythiazolo[2,3-a]isoquinolinium hydroxide (internal salt) of m.p. 276° (dec.).

In an analogous manner, (ac) from 7-chloro-3,4-dihydroisoquinoline-1(2H)-thione and α-bromophenylacetyl chloride (method A) or 1-phenyl-2,2-dicyanooxirane (method B) there was obtained 9-chloro-2-phenyl-5,6-dihydro-3-hydroxythiazolo[2,3-a]isoquinolinium hydroxide (internal salt) of m.p. 296° (dec.);

(ad) from 7-chloro-3,4-dihydroisoquinoline-1(2H)-thione and 1-(o-chlorophenyl)-2,2-dicyanooxirane there was obtained 9-chloro-2-(o-chlorophenyl)-5,6-dihydro-3-hydroxythiazolo[2,3-a]isoquinolinium hydroxide (internal salt) of m.p. 260°–262° (method B, dimethylformamide as the solvent);

(ba) 4.2 g of 9-chloro-2-phenyl-5,6-dihydro-3-hydroxythiazolo[2,3-a]isoquinolinium hydroxide (internal salt) were heated under reflux for 4 hours in 100 ml of toluene together with 1.32 ml of methyl propiolate. After concentration in vacuo, the residue was chromatographed on silica gel with toluene/acetone (9:1). There was obtained methyl 10-chloro-6,7-dihydro-4-oxo-3-phenyl-4H-benzo[a] quinolizine-1-carboxylate of m.p. 139°–141° (from ethyl acetate).

In an analogous manner, (bb) from 9-chloro-2-(p-chlorophenyl)-5,6-dihydro-3-hydroxythiazolo[2,3-a]isoquinolinium hydroxide (internal salt) and methyl propiolate there was obtained methyl 10-chloro-3-(p-chlorophenyl)-6,7-dihydro-4-oxo-4H-benzo[a]quinolizine-1-carboxylate of m.p. 138.5°–140.5° (from ethyl acetate);

(bc) from 9-chloro-2-(o-chlorophenyl)-5,6-dihydro-3-hydroxythiazolo[2,3-a]isoquinolinium hydroxide (internal salt) and methyl propiolate there was obtained methyl 10-chloro-3-(o-chlorophenyl)-6,7-dihydro-4-oxo-4H-benzo[a]quinolizine-1-carboxylate of m.p. 87.5–89.5° (from ethanol);

(bd) from 5,6-dihydro-3-hydroxy-2-phenyl-thiazolo[2,3-a]isoquinolinium hydroxide (internal salt) and methyl propiolate there was obtained methyl 6,7-dihydro-3-phenyl-4-oxo-4H-benzo[a]quinolizine-1-carboxylate of m.p. 196.5°–197.5° (from ethanol);

(be) from 5,6-dihydro-3-hydroxy-2-phenyl-thiazolo[2,3-a]isoquinolinium hydroxide (internal salt) and phenylvinyl sulfoxide in xylene there was obtained 6,7-dihydro-3-phenyl-4H-benzo[a]quinolizine-4-one of m.p. 139.5°–140.5° (from acetonitrile):

(bf) from 9-chloro-2-phenyl-5,6-dihydro-3-hydroxythiazolo[2,3-a]isoquinolinium hydroxide (internal salt) and ethyl propiolate there was obtained ethyl 10-chloro-6,7-dihydro-4-oxo-3-phenyl-4H-benzoquinolizine-1-carboxylate of m.p. 114°–116° (from ethanol).

EXAMPLE 29

(a) 4.08 g of 5,6-dihydro-3-hydroxy-2-phenyl-thiazolo[2,3-a]isoquinolinium hydroxide (internal salt) and 1.95 ml of acrylonitrile were heated together under reflux overnight in 250 ml of toluene. After evaporation of the solvent in vacuo, the residue was recrystallized from acetonitrile. There was obtained 1,2,3,4,6,7-hexahydro-4-oxo-3-phenyl-3,11b-epithio-11bH-benzo[a]quinolizine-1-carbonitrile of m.p. 225°–226°.

(b) 1.7 g of 1,2,3,4,6,7-hexahydro-4-oxo-3-phenyl-3,11b-epithio-11bH-benzo[a]quinolizine-1-carbonitrile were heated at reflux for 2 hours together with a sodium methylate solution (prepared from 156 mg of sodium in 40 ml of methanol). After cooling, the crystallized-out product was removed by filtration under suction and recrystallized from isopropanol. There was obtained pure 6,7-dihydro-4-oxo-3-phenyl-4H-benzo[a]quinolizine-1-carbonitrile of m.p. 204°–205°.

EXAMPLE 30

(aa) A solution of 24.51 g of methyl 10-chloro-6,7-dihydro-4-oxo-3-phenyl-4H-benzo[a]quinolizine-1-carboxylate and 3.91 g of sodium hydroxide in 267 ml of ethanol was heated under reflux overnight. The solvent was removed by evaporation in vacuo, the residue was taken up in water, extracted with chloroform, the aqueous phase was made acid with 2N hydrochloric acid and the precipitated 10-chloro-6,7-dihydro-4-oxo-3-phenyl-4H-benzo[a]quinolizine-1-carboxylic acid of m.p. 280°–283° was removed by filtration.

In an analogous manner, (ab) from methyl 6,7-dihydro-4-oxo-3-phenyl-4H-benzo[a]quinolizine-1-carboxylate and sodium hydroxide there is obtained 6,7-dihydro-4-oxo-3-phenyl-4H-benzo[a]quinolizine-1-carboxylic acid;

(ac) from 10-chloro-4-oxo-3-phenyl-4H-benzo[a]quinolizine-1-carboxylate there was obtained 10-chloro-4-oxo-3-phenyl-4H-benzo[a]quinolizine-1-carboxylic acid of m.p. 221°–222°.

(ba) 2 g of 10-chloro-6,7-dihydro-4-oxo-3-phenyl-4H-benzo[a]quinolizine-1-carboxylic acid were added portionwise while stirring to 5.7 ml of thionyl chloride. The mixture was stirred at room temperature for 1 hour, whereupon the excess thionyl chloride was removed in vacuo and the residue was dissolved in 100 ml of toluene. 0.58 ml of triethylamine was added thereto while stirring and the mixture was subsequently treated with 0.67 ml of 2-dimethylaminoethylamine. The reaction mixture was stirred at room temperature for 2 hours, treated with saturated aqueous sodium bicarbonate solution and extracted three times with methylene chloride. The organic phase was dried over sodium sulfate, filtered and evaporated. The hydrochloride was prepared from the material obtained by means of methanolic hydrochloric acid. By recrystallization from methanol/diethyl ether. there was obtained 10-chloro-N-[2-(dimethylamino)ethyl]-6,7-dihydro-4-oxo-3-phenyl-4H-benzo[a]quinolizine-1-carboxamide hydrochloride of m.p. 160°–162°.

In an analogous manner, (bb) from 10-chloro-6,7-dihydro-4-oxo-3-phenyl-4H-benzo[a]quinolizine-1-carboxylic acid and 2-dimethylaminoethanol there was obtained 2-(dimethylamino)ethyl 10-chloro-6,7-dihydro-4-oxo-3-phenyl-4H-benzo[a]quinolizine-1-carboxylate hydrochloride of m.p. 223°–225° (from methanol/diethyl ether);

(bc) from 10-chloro-6,7-dihydro-4-oxo-3-phenyl-4H-benzo[a]quinolizine-1-carboxylic acid and N-methylpiperazine there was obtained 1-[(10-chloro-6,7-dihydro-4-oxo-3-phenyl-4H-benzo[a]quinolizin-1-yl)carbonyl]-4-methylpiperazine hydrochloride of m.p. 275°–278° (from methanol/diethyl ether);

(bd) from 10-chloro-6,7-dihydro-4-oxo-3-phenyl-4H-benzo[a]quinolizine-1-carboxylic acid and morpholine there was obtained 4-[(10-chloro-6,7-dihydro-4-oxo-3-phenyl-4H-benzo[a]quinolizin-1-yl)carbonyl]morpholine of m.p. 245°–248° (from dioxane/diethyl ether);

(be) from 10-chloro-6,7-dihydro-4-oxo-3-phenyl-4H-benzo[a]quinolizine-1-carboxylic acid and 2,6-cis-dimethylmorpholine there was obtained cis-4-[(6,7-dihydro-4-oxo-3-phenyl-10-chloro-4H-benzo[a]quinolizin-1-yl)carbonyl]-2,6-dimethylmorpholine of m.p. 137°–140°;

(bf) from 10-chloro-6,7-dihydro-4-oxo-3-phenyl-4H-benzo[a]quinolizine-1-carboxylic acid and 4-piperidinol there was obtained 4-[(10-chloro-6,7-dihydro-4-oxo-3-phenyl-4H-benzo[a]quinolizin-1-yl)carbonyl]-4-piperidinol of m.p. 130°—134°;

(bg) from 10-chloro-6,7-dihydro-4-oxo-3-phenyl-4H-benzo[a]quinolizine-1-carboxylic acid and 2-methoxyethylamine there was obtained 10-chloro-6,7-dihydro-N-(2-methoxyethyl)-4-oxo-3-phenyl-4H-benzo[a]quinolizine-1-carboxamide of m.p. 157°–158°;

(bh) from 6,7-dihydro-4-oxo-3-phenyl-4H-benzo[a]quinolizine-1-carboxylic acid and 2-methoxyethylamine there was obtained 6,7-dihydro-N-(2-methoxyethyl)-4-oxo-3-phenyl-4H-benzo[a]quinolizine-1-carboxamide of m.p. 166°–167°;

(bi) from 6,7-dihydro-4-oxo-3-phenyl-4H-benzo[a]quinolizine-1-carboxylic acid and 4-piperidinol there was obtained 1-[(6,7-dihydro-4-oxo-3-phenyl-4H-benzo[a]quinolizin-1-yl)carbonyl]-4-piperidinol of m.p. 220°–222°;

(bj) from 6,7-dihydro-4-oxo-3-phenyl-4H-benzo[a]quinolizine-1-carboxylic acid and 2,6-cis-dimethylmorpholine there was obtained cis-4-[(6,7-dihydro-4-oxo-3-phenyl-4H-benzo[a]quinolizin-1-yl)carbonyl]-2,6-dimethylmorpholine of m.p. 221°–223°;

(bk) from 6,7-dihydro-4-oxo-3-phenyl-4H-benzo[a]quinolizine-1-carboxylic acid and morpholine there was obtained 4-[(6,7-dihydro-4-oxo-3-phenyl-4H-benzo[a]quinolizin-1-yl)carbonyl]morpholine of m.p. 242°–244°;

(bl) from 6,7-dihydro-4-oxo-3-phenyl-4H-benzo[a]quinolizine-1-carboxylic acid and N-methylpiperazine there was obtained 1-[(6,7-dihydro-4-oxo-3-phenyl-4H-benzo[a]quinolizin-1-yl)carbonyl]-4-methylpiperazine hydrochloride of m.p. 212°–214°;

(bm) from 10-chloro-6,7-dihydro-4-oxo-3-phenyl-4H-benzo[a]quinolizine-1-carboxylic acid and ethanolamine there was obtained 10-chloro-6,7-dihydro-N-(2-hydroxyethyl)-4-oxo-3-phenyl-4H-benzo[a]quinolizine-1-carboxamide of melting point 145°–147°;

(bn) from 10-chloro-6,7-dihydro-4-oxo-3-phenyl-4H-benzo[a]quinolizine-1-carboxylic acid and 3-pyrrolidinol there was obtained 1-[(10-chloro-6,7-dihydro-4-oxo-3-phenyl-4-H-benzo[a]quinolizin-1-yl)carbonyl]-3-pyrrolidinol of m.p. 215°–217°;

(bo) from 10-chloro-6,7-dihydro-4-oxo-3-phenyl-4H-benzo[a]quinolizine-1-carboxylic acid and 2-(S)-pyrrolidinemethanol there was obtained (S)-1-[[(10-chloro-6,7-dihydro-4-oxo-3-phenyl-4H-benzo[a]quinolizin-1-yl]carbonyl]-2-pyrrolidinemethanol of m.p. 164°–166°;

(bp) from 10-chloro-6,7-dihydro-4-oxo-3-phenyl-4H-benzo[a]quinolizine-1-carboxylic acid and tetrahydro-4H-1,4-thiazine there was obtained 4-[(10-chloro-6,7-dihydro-4-oxo-3-phenyl-4H-benzo[a]quinolizin-1-yl)carbonyl]-tetrahydro-4H-1,4-thiazine of m.p. 262°–263°;

(bq) from 10-chloro-6,7-dihydro-4-oxo-3-phenyl-4H-benzo[a]quinolizine-1-carboxylic acid and 2-(R)-pyrrolidinemethanol there was obtained (R)-1-[(10-chloro-6,7-dihydro-4-oxo-3-phenyl-4H-benzo[a]quinolizin-1-yl)carbonyl]-2-pyrrolidinemethanol of m.p. 175°–177°;

(br) from 10-chloro-6,7-dihydro-4-oxo-3-phenyl-4H-benzo[a]quinolizine-1-carboxylic acid and 2-piperidinemethanol there was obtained 1-[(10-chloro-6,7-dihydro-4-oxo-3-phenyl)-4H-benzo[a]quinolizin-1-yl)carbonyl]-2-piperidinemethanol of m.p. 214°–216°;

(bs) from 10-chloro-6,7-dihydro-4-oxo-3-phenyl-4H-benzo[a]quinolizine-1-carboxylic acid and 3-methoxypropylamine there was obtained 10-chloro-6,7-dihydro-N-(3-methoxypropyl)-4-oxo-3-phenyl-4H-benzo[a]quinolizine-1-carboxamide of m.p. 149°;

(bt) from 10-chloro-6,7-dihydro-4-oxo-3-pheny-4H-benzo[a]quinolizine-1-carboxylic acid and 1-amino-2-thiazoline there was obtained 10-chloro-N-(4,5-dihydro-2-thiazolinyl)-6,7-dihydro-4-oxo-3-phenyl-4H-benzo[a]quinolizine-1 -carboxamide of m.p. 190°–191°;

EXAMPLE 31

(aaa) 38.9 g of methyl 3,3'-dithiobis-thiophene-2-carboxylate was suspended in 1500 ml of 1N sodium hydroxide solution and 700 ml of ethanol, whereupon the suspension was heated under reflux until the reaction finished. After cooling, in an ice-bath and mixture was acidified with 25 percent hydrochloric acid, whereby the product crystallized out. By recrystallization from water, there was obtained 3,3'-dithio-bis-thiophene-2-carboxylic acid as colorless crystals of m.p. 256°–257°.

(aab) 41.3 g of 3,3'-dithiobis-thiophene-2-carboxylic acid were suspended in 340 ml of thionyl chloride, whereupon the suspension was heated under reflux for 2.5 hours. The excess thionyl chloride was removed in vacuo and the residue was suspended in 700 ml of dioxane. Ammonia was now conducted into the solution. After cooling in an ice-bath, the mixture was filtered and the crystals were stirred in 1500 ml of water for 30 minutes. The crystals were removed by crystallization. By recrystallization from n-butanol/dioxane, there was obtained 3.3'-dithiobisthiophene-2-carboxamide as colorless crystals of m.p. 222°–223°.

(aac) 77.5 g of 3,3'-dithio-bis-thiophene-2-carboxamide were suspended in 1200 ml of dioxane, whereupon the suspension was warmed to 45° under an inert gas. 46.4 g of sodium borohydride were added portionwise to the suspension at 45°–48°. After the evolution of hydrogen finished, the mixture was heated under reflux until the disulfide disappeared. 450 ml of water were now added dropwise while cooling and the mixture was subsequently acidified with 2N hydrochloric acid. After dilution of the solution with 1800 ml of water and saturation with sodium chloride, it was extracted exhaustively with ether. The combined extracts were dried over sodium sulfate, filtered and evaporated. After drying, there was obtained crude 3-mercaptothiophene-2-carboxamide of m.p. 116°–120°.

(aad) 11.1 g of 3-mercapto-thiophene-2-carboxamide, 2.2 g of 95 percent paraformaldehyde and 13.3 g of p-toluenesulfonic acid monohydrate were heated together under reflux with 300 ml of mesitylene. After the reaction finished, the mixture was left to cool and the solvent was removed in vacuo. After chromatography of the residue on silica gel and recrystallization from ethyl acetate, there was obtained 2,3-dihydro-4H-thieno[2,3-e][1,3]thiazin-4-one as yellowish crystals of m.p. 153°–155°.

(aae) 19.6 g of 2.3-dihydro-4H-thieno[2,3-e][1,3]-thiazin-4-one were heated under reflux together with 23.1 g of Lawesson reagent in 200 ml of acetonitrile until all of the starting material reacted. The reaction mixture was cooled and the crystallized-out product was removed by filtration. By recrystallization from ethyl acetate there was obtained pure 2,3-dihydro-4H-thieno[2,3-e][1,3]thiazine-4-thione of m.p. 136°–138°. Additional material can be obtained by evaporation of the mother liquor and recrystallization.

(aba) In an analogous manner, from 4,5,6,7-tetrahydro-8H-thieno[2,3-c]azepine-8-one there was obtained 4,5,6,7-tetrahydro-8H-thieno[2,3-c]azepine-8-thione of m.p. 103°-104° (from ethyl acetate.

(aca) Method A: 17.4 g of methyl 3-mercapto-thiophene-2-carboxylate was dissolved in 350 ml of toluene under an inert gas atmosphere, whereupon the solution was treated with 20.5 g of 2-aminoethyl bromide hydrobromide and then with 100 ml of 3N sodium methylate solution in methanol. The mixture was stirred at room temperature for 30 minutes and thereafter heated under reflux until the reaction finished. The mixture was evaporated in vacuo, the residue was taken up in 300 ml of water, acidified with 2N hydrochloric acid and the crystals were removed by filtration. By recrystallization from chloroform there was obtained 3,4-dihydro-thieno[2,3-f][1,4]thiazepin-5-(2H)-one as white crystals of m.p. 186°-188°.

Method B: 65.4 g of methyl 3-mercapto-thiophene-2-carboxylate were dissolved in 800 ml of ethanol, whereupon the solution was treated with 19.4 ml of ethyleneimine. After the reaction finished, the reaction mixture was cooled in an ice-bath and the hydrochloride precipitated by the introduction of dry hydrogen chloride. The crystals were removed by filtration and the filtrate evaporated, whereby additional crude product was obtained. By recrystallization from methanol/ethyl acetate there is obtained methyl 3-[(2-aminoethyl)thio]-2-thiophenecarboxylate hydrochloride as white crystals of m.p. 174°-176°.

1.0 g of methyl 3-[(2-aminoethyl)thio]-2-thiophenecarboxylate hydrochloride was suspended in 20 ml of toluene under argon, whereupon 9.4 ml of 1N sodium methylate solution in methanol were added. After the reaction finished, the mixture was evaporated in vacuo and the residue was treated with 20 ml of water. The crystals were removed by filtration, washed with water and dried. By recrystallization there was obtained 3,4-dihydrothieno-[2,3-f][1,4]thiazepin-5(2H)-one as white crystals of m.p. 186°-188°. The reaction can also be carried out with 1.1 mol equivalents of potassium tert-butylate solution in toluene.

(acb) 1.0 g of 3,4-dihydro-thieno[2,3-f][1,4]thiazepin-5(2H)-one was heated under reflux for 5 hours together with 15 ml of pyridine and 1.35 g of phosphorus pentasulfide. After cooling the mixture was poured into 90 ml of water and the crystals were removed by filtration. After chromatography on silica gel, the product was recrystallized from ethyl acetate. There was obtained 3,4-dihydro-thieno-[2,3-f][1,4]thiazepine-5(2H-thione as yellow crystals of m.p. 138°-139°.

(ada) 288 g of thieno[2,3-c]pyridine were dissolved in 5.3 l of methylene chloride and an equivalent amount of m-chloroperbenzoic aciid was added portionwise at −5° to 0°. The mixture was stirred until the reaction was completed. The addition of 800 ml of saturated ethereal hydrogen chloride solution precipitated the product as white crystals which were washed with ether. The thus-obtained thieno[2,3-c]pyridine-6-oxide hydrochloride was sufficiently pure for use in the next step, m.p. 202°.

(adb) 671.5 g of thieno[2,3-c]pyridine 6-oxide hydrochloride were suspended in 4000 ml of dioxane under argon and 655 ml of phosphorus oxychloride are added. The mixture was heated on an oil-bath until the exothermic reaction set in. After the exothermic reaction faded away, the mixture was heated to reflux for an additional 10 minutes. The mixture was concentrated in vacuo and the residue was taken up in 2000 ml of toluene. The solution was then treated with 300 ml of water while cooling slowly. The mixture was neutralized by the portionwise addition of sodium carbonate. The organic phase was separated and the aqueous phase was extracted with 1000 ml of toluene. After washing with water, the combined organic solutions were dried over sodium sulfate, filtered and evaporated, whereby crude 7-chloro-thieno[2,3-c]pyridine was obtained as a brown oil.

(adc) 4.85 g of 7-chloro-thieno[2,3-c]pyridine were dissolved in 15 ml of dimethylformamide and 3.18 g of sodium hydrogen sulfide monohydrate were added under argon. The mixture was heated to 110°-115° for one hour, an additional 1.06 g of sodium hydrogen sulfide monohydrate were added and the mixture was held at the temperature indicated above for an additional hour. The mixture was poured on to 150 ml of ice-water and acidified with 1N aqueous hydrochloric acid solution. After stirring at 2° for a short time, the yellowish crystals were removed by filtration. After recrystallization from a toluene/ethyl acetate mixture, there was obtained pure thieno[2,3-c]pyridine-7(6H)-thione, m.p. 187°-189°.

(ba) 16.7 g of thieno[2,3-c]pyridine-7(6H)-thione were suspended in 1000 ml of methylene chloride under an inert gas atmosphere, whereupon 15.3 ml of about 90 percent α-bromophenacetyl chloride were added dropwise. After completion of the addition the mixture was stirred at room temperature for about an additional half hour and then added dropwise to 27.8 ml of triethylamine. The mixture was subsequently stirred at room temperature for 30 minutes. The solution was washed twice with 750 ml of water each time, dried over sodium sulfate, filtered and evaporated in vacuo. The red crystals obtained were purified by chromatography and recrystallization from chloroform/ether/hexane. There was obtained 3-hydroxy-2-phenylthiazolo[3,2-a]thieno[2,3-c]pyridinium hydroxide (internal salt) as red crystals of m.p. 195°-200° (dec.).

In an analogous manner, (bb) from 2,3-dihydro-4H-thieno[2,3-e][1,3]thiazine-4-thione and α-bromophenacetyl chloride there was obtained 7-hydroxy-8-phenyl-5H-thiazolo[3,2-c]thieno[2,3-e][1,3]-thiazinium hydroxide (internal salt) of m.p. 194°-197° (from methanol);

(bc) from 4,5,6,7-tetrahydro-8H-thieno[2,3-c]azepine-8-thione and α-bromophenacetyl chloride there was obtained 5,6-dihydro-8-hydroxy-9-phenyl-4H-thiazolo[3,2-a]thieno-[2,3-c]azepinium hydroxide (internal salt) of m.p. 205°-208° (from chloroform/diethyl ether);

(bd) from 3,4-dihydrothieno[2,3-f][1,4]thiazepine-5(2H)-thione and α-bromophenacetyl chloride there was obtained 5,6-dihydro-8-hydroxy-9-phenyl-thiazolo[3,2-d]thieno-[2,3f][1,4]thiazepinium hydroxide (internal salt) of m.p. 196°-198° (from chloroform-diethyl ether).

(ca) 22.9 g of 3-hydroxy-2-phenylthiazolo[3,2-a]thieno-[2,3-c]pyridinium hydroxide (internal salt) and 13.6 ml of methyl propiolate were heated together under argon in 1000 ml of toluene until the starting material was completely taken up. The solvent was removed in vacuo and the residue was stirred in 500 ml of ether/methanol (9:1) for 1 hour. The yellow crystals obtained were removed by filtration under suction. There was obtained methyl 7-oxo-8-phenyl-7H-thieno[2,3-a]quinolizine-10-carboxylate of m.p. 153°-154° (dec.). An additional portion of product of m.p. 151°–152° (dec.) can be obtained by chromatography of the filtrate on silica gel.

In an analogous manner.

(cb) from 7-hydroxy-8-phenyl-5H-thiazolo[3,2-c]thieno-]2,3-e][1,3]thiazinium hydroxide (internal salt) and methyl propiolate there was obtained methyl 7-oxo-8-phenyl-5H-pyrido[1,2-c]thieno[2,3-c][1,3]thiazine-10-carboxylate of m.p. 141°–143° (from methanol);

(cc) from 5,6-dihydro-8-hydroxy-9-phenyl-4H-thiazolo[3,2-a]thieno[2,3-c]azepinium hydroxide (internal salt) and methyl propiolate there was obtained methyl 8-oxo-9-phenyl-4,5,6,8-tetrahydropyrido[1,2-a]thieno[2,3-c]azepine-11-carboxylate of m.p. 142°–144° (from ethyl acetate);

(cd) from 5,6-dihydro-8-hydroxy-9-phenyl-thiazolo[3,2-d]thieno[2,3-f][1,4]thiazepinium hydroxide (internal salt) and methyl propiolate there was obtained methyl 5,6-dihydro-8-oxo-9-phenyl-8H-pyrido[1,2-d]thieno[2,3-f][1,4]thiazepine-11-carboxylate of m.p. 158°–160° (from ethanol).

EXAMPLE 32

(aa) 1.34 g of methyl 7-oxo-8-phenyl-7H-thieno[2,3-a]quinolizine-10-carboxylate were heated under reflux and under argon with 0.45 g of potassium hydroxide in 25 ml of water/methanol. After the reaction was completed, the mixture was acidified with 2N hydrochloric acid and the yellow crystals were removed by filtration. After washing with water, the acid was dried in vacuo for several hours. There was obtained 7-oxo-8-phenyl-7H-thieno[2,3-a]quinolizine-10-carboxylic acid of m.p. 185°–186° (dec.).

In an analogous manner, (ab) from methyl 8-oxo-9-phenyl-4,5,6,8-tetrahydropyrido[1,2-a]thieno[2,3-c]azepine-11-carboxylate there was obtained 8-oxo-9-phenyl-4,5,6,8-tetrahydropyrido[1,2-a]thieno[2,3-c]azepin-11-carboxylic acid of m.p. 226°–229° (dec.);

(ac) from methyl 5,6-dihydro-8-oxo-9-phenyl-8H-pyrido[1,2-d]thieno[2,3-f][1,4]thiazepin-11-carboxylate there was obtained 5,6-dihydro-8-oxo-9-phenyl-8H-pyrido[1,2-d]thieno[2,3-f][1,4]thiazepin-11-carboxylic acid of m.p. 265°–266° (dec.; from methanol/dimethylformamide).

(ba) 0.64 g of 7-oxo-8-phenyl-7H-thieno[2,3-a]quinolizine-10-carboxylic acid were suspended in 12 ml of toluene, whereupon 0.9 ml of thionyl chloride and catalytic amounts of dimethylformamide were added at room temperature and with the exclusion of moisture. The mixture was stirred at room temperature for 1 hour and then evaporated in vacuo. the residue was taken up in 15 ml of dioxane. After the addition of 0.7 ml of morpholine, the mixture was stirred at room temperature for 1 hour. The mixture was diluted with water and the crystals were removed by filtration. By recrystallization from ethanol/dimethylformamide there was obtained 4-[(7-oxo-8-phenyl-7H-thieno[2,3-a]quinolizin-10-yl)-carbonyl]morpholine as yellow crystals of m.p. 271°–272° (dec.).

In an analogous manner, (bb) from 8-oxo-9-phenyl-4,5,6,8-tetrahydropyrido[1,2-a]thieno[2,3-c]azepin-11-carboxylic acid and morpholine there was obtained 4-[(8-oxo-9-phenyl-4,5,6,8-tetrahydropyrido[1,2-a]thieno[2,3-c]azepin-11-yl)carbonyl]morpholine of m.p. 238°–240° (from ethanol);

(bc) from 5,6-dihydro-8-oxo-9-phenyl-8H-pyrido[1,2-d]thieno[2,3-f][1,4]thiazepin-11-carboxylic acid and morpholine there was obtained 4-[(5,6-dihydro-8-oxo-9-phenyl-8H-pyrido[1,2-d]thieno[2,3-f][1,4]thiazepin-11-yl)carbonyl]morpholine of m.p. 253°–254° (from ethanol);

(bd) from 5,6-dihydro-8-oxo-9-phenyl-8H-pyrido[1,2-d]thieno[2,3-f][1,4]thiazepin-11-carboxylic acid and 2-(dimethylamino)-ethylamine there was obtained N-[2-dimethylamino)ethyl]-5,6-dihydro-8-oxo-9-phenyl-8H-pyrido[1,2-d]thieno[2,3-f][1,4]thiazepin-11-carboxamide of m.p. 155°–157° (from ethyl acetate);

(be) from 5,6-dihydro-8-oxo-9-phenyl-8H-pyrido[1,2-d]thieno[2,3-f][1,4]thiazepin-11-carboxylic acid and 2-dimethylaminoethanol there was obtained 2-(dimethylamino)ethyl 5,6-dihydro-8-oxo-9-phenyl-8H-pyrido[1,2-d]thieno[2,3-f][1,4]thiazepin-11-carboxylate of m.p. 115°–117° (from cyclohexane).

EXAMPLE 33

(a) 11.22 g of 7-oxo-8-phenyl-7H-thieno[2,3-a]quinolizine-10-carboxylic acid were suspended in 40 ml of benzene, whereupon 1.8 ml of N,N-dimethylformamide di-tert-butyl acetal were added thereto, the mixture was heated under reflux for 15 minutes, an additional 1.8 ml of the above reagent were added thereto, the mixture was again heated under reflux for 15 minutes and this procedure was repeated again. After the reaction was completed, the mixture was evaporated in vacuo. After chromatography of the residue on silica gel and recrystallization from toluene, there was obtained tert-butyl 7-oxo-8-phenyl-7H-thieno[2,3-a]quinolizine-10-carboxylate as yellow crystals of m.p. 155°–157°.

(b) In an analogous manner, from 5,6-dihydro-8-oxo-9-phenyl-8H-pyrido[1,2-d]thieno[2,3-f][1,4]-thiazepin-11-carboxylic acid and N,N-dimethylformamide di-tert-butyl acetal there was obtained tert-butyl 5,6-dihydro-8-oxo-9-phenyl-8H-pyrido[1,2-d]thieno[2,3-f][1,4]thiazepin-11-carboxylate of m.p. 185°–187° (from toluene).

EXAMPLE 34

(a) 1.93 g of 7-oxo-8-phenyl-7H-thieno[2,3-a]quinolizine-10-carboxylic acid were converted into the acid chloride with 2.65 ml of thionyl chloride as described. This acid chloride was taken up in 80 ml of dioxane, treated with 2.7 ml of N-methylpiperazine, and the mixture was then stirred at room temperature until the reaction was completed and poured into 200 ml of water. The aqueous phase was saturated with sodium chloride and extracted several times with ethyl acetate. The combined organic phases were dried over sodium sulfate, filtered and evaporated. By recrystallization from toluene there was obtained 1-methyl-4-[(7-oxo-8-phenyl-7H-thieno[2,3-a]quinolizin-10-yl)carbonyl]piperazine as yellow crystals of m.p. 233°–234° (dec.).

In an analogous manner, (b) from 8-oxo-9-phenyl-4,5,6,8-tetrahydropyrido[1,2-a]thieno[2,3-c]azepin-11-carboxylic acid and 4-piperidinol there was obtained 1-[(8-oxo-9-phenyl-4,5,6,8-tetrahydropyrido[1,2-a]thieno[2,3-c]azepin-11-yl)carbonyl]-4-piperidinol of m.p. 196°–198° (from acetonitrile).

EXAMPLE 35

3.45 g of 5,6-dihydro-8-oxo-9-phenyl-8H-pyrido[1,2-d]thieno[2,3-f][1,4]thiazepine-11-carboxylic acid were heated to 285° at 0.5 Torr, whereupon the temperature was held at 258°–262° for an additional 40 minutes. The crude product was chromatographed on silica gel. After recrystallization from acetonitrile, there was obtained 5,6-dihydro-9-phenyl-8H-pyrido[1,2-d]thieno[2,3-f][1,4]thiazepin-8-one as yellow crystals of m.p. 139°–141°.

EXAMPLE 36

4.95 g of 5,6-dihydro-9-phenyl-8H-pyrido[1,2-d]thieno[2,3-f][1,4]thiazepin-8-one were added under argon to 2.35 g of N-chlorosuccinimide in 50 ml of carbon tetrachloride. The mixture was stirred at room temperature for 2.5 hours, treated with an additional 0.21 g of N-chlorosuccinimide and stirred for an additional 1 hour. After evaporation in vacuo, the residue was chromatographed on silica gel. By recrystallization from acetonitrile, there was obtained 11-chloro-5,6-dihydro-9-phenyl-8H-pyrido[1,2-d]-thieno[2,3-f][1,4]thiazepin-8-one as yellow crystals of m.p. 179°.

EXAMPLE 37

(a) 3.55 g of 5,6-dihydro-8-oxo-9-phenyl-8H-pyrido[1,2-d]thieno[2,3-f][1,4]thiazepine-11-carboxylic acid were reacted with 20 ml of thionyl chloride in the presence of catalytic amounts of dimethylformamide. After the reaction was completed, the solvent was removed in vacuo. There was obtained the crude acid chloride as yellow crystals of m.p. 201°–204°.

(b) 0.89 g of acetamidoxime in 50 ml of methylene chloride was treated with 1.67 ml of triethylamine. The above acid chloride in 100 ml of dichloromethane was added dropwise at 21°–24° while cooling, whereupon the mixture was stirred until the reaction was completed. After washing with water, the organic phase was dried over sodium sulfate, filtered and the residue was evaporated in vacuo. The crude material was heated under reflux in the presence of catalytic amounts of p-toluenesulfonic acid together with 110 ml of toluene, whereby the reaction water which was formed was removed via a water separator. After chromatography on silica gel, the product was recrystallized from ethyl acetate, whereby there was obtained 5,6-dihydro-11-(3-methyl-1,2,4-oxadiazol-5-yl)--phenyl-8H-pyrido[1,2-d]-thieno[2,3-f][1,4]thiazepin-8-one as yelloww crystals of m.p. 183°–185°.

EXAMPLE 38

3.8 g of 2-(dimethylamino)ethyl 5,6-dihydro-8-oxo-9-phenyl-8H-pyrido[1,2-d]thieno[2,3-f][1,4]thiazepine-11-carboxylate in 90 ml of methylene chloride were treated with 9 ml of 3N ethanolic hydrochloric acid, whereupon the mixture was cooled to −10°. The mixture was treated dropwise with 1.72 g of about 90 percent m-chloroperbenzoic acid in 45 ml of methylene chloride. After warming to room temperature, the mixture was washed with 100 ml of 5 percent sodium hydrogen carbonate solution, dried over sodium sulfate, filtered and evaporated in vacuo. The residue was purified by chromatography on silica gel and then dissolved in 34 ml of methylene chloride. After the addition of 3N ethanolic hydrochloric acid until an acidic reaction was obtained, the mixture was stirred at room temperature for an additional 15 minutes. After removal of the solvent in vacuo and recrystallization from methanol, there was obtained 2-(dimethylamino)ethyl 5,6-dihydro-8-oxo-9-phenyl-8H-pyrido[1,2-d]thieno[2,3-f][1,4]thiazepine-11-carboxylate 4-oxide hydrochloride as yellow crystals of m.p. 148°–152° (dec.).

EXAMPLE 39

(a) 4 g of methyl-7-oxo-8-phenyl-pyrido[1,2-c]thieno[2,3-e][1,3]thiazine-10-carboxylate were dissolved in 100 ml of methylene chloride, whereupon the solution was cooled to 0° and a solution of 2.43 g of m-chloroperbenzoic acid in 40 ml of methylene chloride was added dropwise. After the reaction was completed, the precipitated m-chlorobenzoic acid was removed by filtration and the filtrate was washed with saturated sodium hydrogen carbonate solution and water, dried over sodium sulfate, filtered and evaporated. After chromatography on silica gel, the product was recrystallized from acetonitrile. There was obtained methyl 7-oxo-8-phenyl-pyrido[1,2-c]thieno[2,3-e]-[1,3]thiazine-10-carboxylate 4-oxide as yellow crystals of m.p. 183°–186°.

In an analogous manner, from m-chloroperbenzoic acid and:

(b) tert.Butyl 5,6-dihydro-8-oxo-9-phenyl-8H-pyrido[1,2-d]thieno[2,3-f][1,4]thiazepine-11-carboxylate there was obtained tert-butyl 5,6-dihydro-8-oxo-9-phenyl-8H-pyrido[1,2-d]thieno[2,3-f][1,4]thiazepine-11-carboxylate 4-oxide of m.p. 185°–187° (from toluene);

(c) 5,6-dihydro-9-phenyl-8H-pyrido[1,2-d]thieno[2,3-f][1,4]thiazepin-8-one there was obtained 5,6-dihydro-9-phenyl-8H-pyrido[1,2-d]thieno[2,3-f][1,4]thiazepin-8-one 4-oxide of m.p. 199°–200° (from methanol);

(d) 11-chloro-5,6-dihydro-9-phenyl-8H-pyrido[1,2-d]thieno[2,3-f][1,4]thiazepin-8-one there was obtained 11-chloro-5,6-dihydro-9-phenyl-8H-pyrido[1,2-d]thieno[2,3-f][1,4]thiazepin-8-one 4-oxide of m.p. 209°–211° (from acetonitrile);

(e) 5,6-dihydro-11-(3-methyl-1,2,4-oxadiazol-5-yl)-9-phenyl-8H-pyrido[1,2-d]thieno[2,3-f][1,4]thiazepin-8-one there was obtained 5,6-dihydro-11-(3-methyl-1,2,4-oxadiazol-5-yl)-9-phenyl-8H-pyrido[1,2-d]thieno[2,3-f][1,4]thiazepin-8-one 4-oxide of m.p. 220° (from acetonitrile);

(f) 4-[(5,6-dihydro-8-oxo-9-phenyl-8H-pyrido[1,2-d]thieno[2,3-f][1,4]thiazepin-11-yl]carbonyl]morpholine there was obtained 4-[(5,6-dihydro-8-oxo-9-phenyl-8H-pyrido[1,2-d]thieno[2,3-f][1,4]thiazepin-11-yl)carbonyl]morpholine 4-oxide of m.p. 170° (from ethanol);

(g) methyl 5,6-dihydro-8-oxo-9-phenyl-8H-pyrido[1,2-d]thieno[2,3-f][1,4]thiazepine-11-carboxylate there was obtained methyl 5,6-dihydro-8-oxo-9-phenyl-8H-pyrido[1,2-d]thieno[2,3-f][1,4]thiazepine-11-carboxylate 4-oxide of m.p. 135°–137° (from ether/n-hexane/ethyl acetate).

EXAMPLE 40

(aa) 15.7 g of methyl 5,6-dihydro-8-oxo-9-phenyl-8H-pyrido[1,2-d]thieno[2,3-f][1,4]thiazepine-11-carboxylate 4-oxide were added portionwise to 70 ml of thionyl chloride with the exclusion of moisture in such a manner that the temperature of the reaction solution is at about 35°. After completion of the addition, the mixture was stirred until the reaction was completed. The excess thionyl chloride was removed in vacuo and the residue was treated with 100 ml of water. The crystals were removed by filtration and dried, whereupon they were chromatographed on silica gel. By recrystallization from toluene, there was obtained methyl 5-chloro-5,6-dihydro-9-phenyl-8H-pyrido[1,2-d]thieno-[2,3-f][1,4]thiazepin-11-carboxylate as yellow crystals of m.p. 192°–196°.

(ab) In an analogous manner, from 11-chloro-5,6-dihydro-9-phenyl-8H-pyrido[1,2-d]thieno[2,3-f][1,4]thiazepin-8-one 4-oxide there was obtained 5,11-dichloro-5,6-dihydro-9-phenyl-8H-pyrido[1,2-d]thieno[2,3-f][1,4]thiazepin-8-one of m.p. 162°–164° (from ethyl acetate).

(ba) 6.05 g of methyl 5-chloro-5,6-dihydro-8-oxo-9-phenyl-8H-pyrido[1,2-d]thieno[2,3-f][1,4]thiazepin-11-carboxylatew ere suspended in 60 ml of dimethyl sulfoxide. 3.6 ml of 1,5-diazabicyclo[4.3.0]non-5-ene were added, whereupon the mixture was heated to 70°–75° in order to complete the reaction. The mixture was then cooled to room temperature, whereby crystals separated. The mixture was poured into 300 ml of water, and the crystals were removed by filtration and washed with water. The still moist crystals were dissolved in chloroform. The solution was dried over sodium sulfate, filtered and evaporated in vacuo. After chromatography on silica gel, there was obtained methyl 8-oxo-9-phenyl-8H-pyrido[1,2-d]thieno[2,3-f][1,4]thiazepin-11-carboxylate as yellow crystals which were recrystallized from toluene. The product then has a m.p. of 207°–210°.

(bb) In an analogous manner, from 5,11-dichloro-5,6-dihydro-9-phenyl-8H-pyrido[1,2-d]thieno(2,3-f]thiazepin-8-one there was obtained 11-chloro-9-phenyl-8H-pyrido[1,2-d]thieno[2,3-f][1,4]thiazepin-8-one of m.p. 149°–151° (from ethyl acetate).

EXAMPLE 41

6.2 g of m-chloroperbenzoic acid (content about 80%) in 130 ml of methylene chloride are added dropwise to 5.5 g of methyl 8-oxo-9-phenyl-8H-pyrido[1,2-d]thieno[2,3-f][1,4]thiazepine-11-carboxylate in 100 ml of methylene chloride. The mixture was allowed to warm to room temperature and was stirred until the reaction was completed. The mixture was washed with saturated sodium hydrogen carbonate solution and water, dried over sodium sulfate, filtered and evaporated. After chromatography on silica gel and recrystallization from toluene, there was obtained methyl 8-oxo-9-phenyl-8H-pyrido[1,2-d]thieno[2,3-f][1,4]thiazepine-11-carboxylate 4,4-dioxide as yellow crystals of m.p. 241°–243°.

EXAMPLE 42

(a) 4.4 g of methyl 8-oxo-9-phenyl-8H-pyrido[1,2-d]thieno[2,3-f][1,4]thiazepine-11-carboxylate were heated under reflux and under argon together with 90 ml of xylene until the reaction was completed. The solution was evaporated in vacuo and the residue was treated with 100 ml of n-hexane, whereupon the product was removed by filtration. By recrystallization from ethyl acetate, there was obtained methyl 7-oxo-8-phenyl-7H-thieno[2,3-a]quinolizine-10-carboxylate as yellow crystals of m.p. 153°–156°.

(b) In an analogous manner, from 11-chloro-9-phenyl-8H-pyrido[1,2-d]thieno[2,3-f][1,4]thiazepine-8-one there was obtained 10-chloro-8-phenyl-7H-thieno[2,3-a]quinolizine-7-one of m.p. 178°–180° (from ethyl acetate).

EXAMPLE 43

(a) A suspension of 0.59 g of 4,5-dihydro-10-(hydroxymethyl)-8-phenyl-7H-thieno[2,3-a]quinolizine-7-one in 15 ml of dioxane was treated with 0.38 ml of phenyl chloroformate and 0.27 ml of pyridine and stirred at room temperature for 2.5 hours. Then, 3 ml of morpholine were added and the mixture was stirred further until the reaction was completed. The mixture was diluted with chloroform, washed with 1N hydrochloric acid, 10 percent potassium bicarbonate solution and saturated sodium chloride solution, dried over magnesium sulfate and concentrated. By crystallization from ethanol, there was obtained pure (4,5-dihydro-7-oxo-8-phenyl-7H-thieno[2,3-a]quinolizin-10-yl)methyl 4-morpholine carboxylate of m.p. 163°–164°.

In an analogous manner, (b) from 4,5-dihydro-10-(hydroxymethyl)-8-phenyl-7H-thieno[2,3-a]quinolizin-7-one and N-methylpiperazine there is obtained (4,5-dihydro-7-oxo-8-phenyl-7H-thieno[2,3-a]quinolizin-10-yl)methyl 4-methyl-1-piperazine carboxylate;

(c) from 4,5-dihydro-10-(hydroxymethyl)-8-phenyl-7H-thieno[2,3-a]quinolizin-7-one and 2,6-dimethylmorpholine there was obtained 4,5-dihydro-7-oxo-8-phenyl-7H-thieno[2,3-a]quinolizin-10-yl)methyl 2,6-dimethyl-4-morpholinecarboxylate of m.p. 156°–157°;

(d) from 4,5-dihydro-10-(hydroxymethyl)-8-phenyl-7H-thieno[2,3-a]quinolizin-7-one and 3-hydroxypyrrolidine there was obtained 4,5-dihydro-7-oxo-8-phenyl-7H-thieno[2,3-a]quinolizin-10-yl)methyl 3-hydroxy-1-pyrrolidinecarboxylate of m.p. 161°–162°;

(e) from 6,7-dihydro-1-(hydroxymethyl)-3-phenyl-10-chloro-4H-benzo[a]quinolizin-4-one and 2,6-dimethylmorpholine there was obtained (10-chloro-6,7-dihydro-4-oxo-3-phenyl-4H-benzo[a]quinolizin-1-yl)methyl 2,6-dimethyl-4-morpholinecarboxylate of m.p. 159.5°–161.5°;

(f) from 6,7-dihydro-1-(hydroxymethyl)-3-phenyl-10-chloro-4H-benzo[a]quinolizin-4-one and aminoacetaldehyde dimethyl acetal there was obtained [10-chloro-6,7-dihydro-4-oxo-3-phenyl-4H-benzo[a]quinolizin-1-yl]methyl-(2,2-dimethoxyethyl)carbamate, M.S.: 468 (M);

(g) from 6,7-dihydro-1-(hydroxymethyl)-3-phenyl-10-chloro-4H-benzo[a]quinolizin-4-one and ethyl 4-piperidinecarboxylate there was obtained 1-[10-chloro-6,7-dihydro-4-oxo-4-phenyl-4H-benzo[a]quinolizin-1-yl]methyl 4-ethyl-1,4-piperidinedicarboxylate of m.p. 122.5°–123.5°;

(h) from 6,7-dihydro-1-(hydroxymethyl)-3-phenyl-10-chloro-4H-benzo[a]quinolizin-4-one and 3-pyrrolidinol there was obtained (10-chloro-6,7-dihydro-4-oxo-3-phenyl-4H-benzo[a]quinolizin-1-yl)methyl 3-hydroxy-1-pyrrolidinecarboxylate of m.p. 224°–225°;

(i) from 6,7-dihydro-1-(hydroxymethyl)-3-phenyl-10-chloro-4H-benzo[a]quinolizin-4-one and aminoacetonitrile there was obtained (10-chloro-6,7-dihydro-4-oxo-3-phenyl-4H-benzo[a]quinolizin-1-yl)methyl-(cyanomethyl)carbamate of m.p. 166°–167°;

(j) from 6,7-dihydro-1-(hydroxymethyl)-3-phenyl-10-chloro-4H-benzo[a]quinolizin-4-one and (S)-2-(hydroxymethyl)pyrrolidine there was obtained (10-chloro-6,7-dihydro-4-oxo-3-phenyl-4H-benzo[a]quinolizin-1-yl)methyl (S)-2-(hydroxymethyl)-pyrrolidinecarboxylate, M.S.: 464 (M+);

(k) from 6,7-dihydro-1-(hydroxymethyl)-3-phenyl-10-chloro-4H-benzo[a]quinolizin-4-one and 1,4-dioxane-azaspiro[4,5]decane there was obtained (10-chloro-6,7-dihydro-4-oxo-3-phenyl-4H-benzo[a]quinolizin-1-yl)methyl 1,4-dioxane--8-azaspiro[4,5]decane-8-carboxylate of m.p. 142–143;

(l) from 10-chloro-6,7-dihydro-1-(hydroxymethyl)-3-phenyl-4H-benzo[a]quinolizin-4-one and methyl (R)-prolinate there was obtained 1-[(10-chloro-6,7-dihydro- 4-oxo-3-phenyl-4H-benzo[a]quinolizin-1-yl)methyl]2-methyl(R)-1,2-pyrrolidinedicarboxylate, M.S.: 492 (M+).

EXAMPLE 44

A mixture of 0.855 g of 5,6-dihydro-3-hydroxy-2-phenylthiazolo[3,2-a]thieno[2,3-c]pyridinium hydroxide (internal salt) and 0.65 ml of 3,3-diethoxypropyne in 30 ml of cyclohexanone was stirred with a few crystals of p-toluenesulfonic acid at 130° for 3 hours under an inert gas and then concentrated in vacuo. The residue was taken up in ethyl acetate, washed with 10 percent potassium bicarbonate solution and saturated sodium chloride solution, dried over magnesium sulfate, concentrated and chromatographed on silica gel with toluene/acetonitrile (19:1). By crystallization from dioxane, there is obtained 4,5-dihydro-7-oxo-8-phenyl-7H-thieno[2,3-a]quinolizine-10-carboxaldehyde of m.p. 213°–215°.

EXAMPLE 45

(a) A solution of 100 mg of 1-[(4,5-dihydro-7-oxo-8-phenyl-7H-thieno[2,3-a]quinolizin-10-yl)carbonyl]-4-piperidinol in 5 ml of methylene chloride was treated with 51 mg of pyridinium chlorochromate. After the reaction was completed, the solvent was evaporated in vacuo and the residue was chromatographed over silica gel. The product was recrystallized from diethyl ether and there was obtained 1-[(4,5-dihydro-7-oxo-8-phenyl-7H-thieno[2,3-a]-quinolizin-10-yl)carbonyl]-4-piperidinone of m.p. 218°–220°.

In an analogous manner, (b) from 1-[[10-chloro-6,7-dihydro-4-oxo-3-phenyl-4H-benzo[a]quinolizin-1-yl]carbonyl]-4-piperidinol there was obtained 1-[[10-chloro-6,7-dihydro-4-oxo-3-phenyl-4H-benzo[a]quinolizin-1-yl]carbonyl]-4-piperidinone of m.p. 164°–166°;

(c) from 1-[[10-chloro-6,7-dihydro-4-oxo-3-phenyl-4H-benzo[a]quinolizin-1-yl]carbonyl]-3-pyrrolidinol there was obtained 1-[(10-chloro-4-oxo-3-phenyl-4H-benzo[a]quinolizin-1-yl)carbonyl]-3-pyrrolidinone of m.p. 196°–198°.

EXAMPLE 46

In analogy to the details in Example 7a), (a) from 3-hydroxy-1-[(7-oxo-8-phenyl-7H-thieno[2,3-a]quinolizin-10-yl)carbonyl]pyrrolidine and methyl iodide there was obtained 3-methoxy-1-[(7-oxo-8-phenyl-7H-thieno[2,3-a]quinolizin-10-yl)carbonyl]pyrrolidine of m.p. 179°–181°;

(b) from (S)-1-[7-oxo-8-phenyl-7H-thieno[2,3-a]quinolizin-10-yl)carbonyl]-2-pyrrolidinemethanol and methyl iodide there was obtained (S)-2-methoxymethyl-1-[(7-oxo-8-phenyl-7H-thieno[2,3-a]quinolizin-10-yl)carbonyl]pyrrolidine of m.p. 153°–155°;

(c) from 1-[(7-oxo-8-phenyl-7H-thieno[2,3-a]quinolizin-10-yl)carbonyl-4-piperidinol and methyl iodide there was obtained 4-methoxy-1-[(7-oxo-8-phenyl-7-H-thieno[2,3-a]quinolizin-10-yl)carbonyl)piperidine of m.p. 200°–203°;

(d) from N-(3-hydroxypropyl)-7-oxo-8-phenyl-7H-thieno[2,3-a]quinolizine-10-carboxamide and approximately 2 mol equivalents of NaH and methyl iodide there was obtained N-(3-methoxypropyl)-N-methyl-7H-thieno[2,3-a]quinolizine-10-carboxamide of m.p. 161°–163°;

(e) from 6,7-dihydro-1-(hydroxymethyl)-3-phenyl-10-chloro-4H-benzo[a]quinolizine-4-one there was obtained 10-chloro-6,7-dihydro-1-(methoxymethyl)-3-phenyl-4H-benzo[a]quinolizin-4-one of m.p. 154°–155°;

(f) from (R)-1-[(7-oxo-8-phenyl-7H-thieno[2,3-a]quinolizin-10-yl)carbonyl]-2-pyrrolidinemethanol and methyl iodide there was obtained (R)-2-methoxymethyl-1-[(7-oxo-8-phenyl-7H-thieno[2,3-a]quinolizin-10-yl)carbonyl]pyrrolidine of m.p. 153°–155°;

(g) from (R)-1-[(7-oxo-8-phenyl-7H-thieno[2,3-a]quinolizin-10-yl)carbonyl]-3-pyrrolidinol and methyl iodide there was obtained (R)-3-methoxy-1-[(7-oxo-8-phenyl-7H-thieno[2,3-a]quinolizin-10-yl)carbonyl]pyrrolidine of m.p. 162°–165°;

(h) from (S)-1-[(7-oxo-8-phenyl-7H-thieno[2,3-a]quinolizin-10-yl)carbonyl]-3-pyrrolidinol and methyl iodide there was obtained (S)-3-methoxy-1-[(7-oxo-8-phenyl-7H-thieno[2,3-a]quinolizin-10-yl)carbonyl]pyrrolidine of m.p. 163°–165°;

(i) from 1-[(10-chloro-4-oxo-3-phenyl-4H-benzo[a]quinolizin-1-yl)carbonyl]-3-pyrrolidinol and methyl iodide there was obtained 1-[(10-chloro-4-oxo-3-phenyl-4H-benzo[a]quinolizin-1-yl)carbonyl]-3-methoxypyrrolidine of m.p. 176°–178°;

(j) from (S)-1-[(10-chloro-4-oxo-3-phenyl-4H-benzo[a]quinolizin-1-yl)carbonyl]-2-pyrrolidinemethanol and methyl iodide there was obtained (S)-1-[(10-chloro-4-oxo-3-phenyl-4H-benzo[a]quinolizin-1-yl)carbonyl]-2-(methoxymethyl)pyrrolidine of m.p. 137°–139°;

(k) from (R)-1-[(10-chloro-4-oxo-3-phenyl-4H-benzo[a]quinolizin-1-yl)carbonyl]-2-pyrrolidinemethanol and methyl iodide there was obtained (R)-1-[(10-chloro-4-oxo-3-phenyl-4H-benzo[a]quinolizin-1-yl)carbonyl]-2-(methoxymethyl)pyrrolidine of m.p. 137°–140°;

(l) from 1-[(7-oxo-8-phenyl-7H-thieno[2,3-a]quinolizin-10-yl)carbonyl]-3-azetidinol and methyl iodide there was obtained 3-methoxy-1-[(7-oxo-8-phenyl-7H-thieno[2,3-a]quinolizin-10-yl)carbonyl]azetidine of m.p. 212°–213°;

(m) from 1-[(7-oxo-8-phenyl-7H-thieno[2,3-a]quinolizin-10-yl)carbonyl]-3-piperidinol and methyl iodide there was obtained 3-methoxy-1-[(7-oxo-8-phenyl-7H-thieno[2,3-a]quinolizin-10-yl)carbonyl]piperidine of m.p. 180°–181°;

(n) from 7-oxo-8-phenyl-N-(tetrahydro-2-furfuryl)-7H-thieno[2,3-a]quinolizine-10-carboxamide and methyl iodide there was obtained N-methyl-7-oxo-8-phenyl-N-(tetrahydro-2-furfuryl)-7H-thieno[2,3-a]quinolizine-10-carboxamide of m.p. 168°–169°;

(o) from N-(2-methoxymethyl)-7-oxo-8-phenyl-7H-thieno[2,3-a]quinolizine-10-carboxamide and ethyl iodide there was obtained N-ethyl-N-(2-methoxyethyl)-7-oxo-8-phenyl-7H-thieno[2,3-a]quinolizine-10-carboxamide of m.p. 141°–143°;

(p) from N-(2-hydroxyethyl)-7-oxo-8-phenyl-7H-thieno[2,3-a]quinolizine-10-carboxamide and about 3 equivalents of methyl iodide there was obtained N-(2-methoxyethyl)-N-methyl-7-oxo-8-phenyl-7H-thieno[2,3a]quinolizine-10-carboxamide of m.p. 126°–128°;

(q) from 1-[(10-chloro-1-oxo-3-phenyl-4H-benzo[a]quinolizin-1-yl)carbonyl]-3-azetidinol and methyl iodide there was obtained 1-[(10-chloro-4-oxo-3-phenyl-4H-benzo[a]quinolizin-1-yl)carbonyl]-3-methoxyazetidine of m.p. 175°–177°;

(r) from (S)-1-[(7-oxo-8-phenyl-7H-thieno[2,3-a]quinolizin-10-yl)carbonyl]-2-azetidinemethanol and methyl iodide there was obtained (S)-2-(methoxymethyl)-1-[(7-oxo-8-phenyl-7H-thieno[2,3-a]quinolizin-10-yl)carbonyl]azetidine of m.p. 95°–100°;

(s) from 1-[(4-oxo-3-(α,α,α-trifluoro-m-tolyl)-4H-quinolizin-1-yl)carbonyl]-3-pyrrolidinol and methyl iodide there was obtained 3-methoxy-1-[[(4-oxo-(α,α,α-trifluoro-m-tolyl)-4H-quinolizin-1-yl]carbonyl]pyrrolidine of m.p. 97°-100°.

EXAMPLE 47

In analogy to the details in Example 32ba), (a) from 7-oxo-8-phenyl-7H-thieno[2,3-a]quinolizine-10-carboxylate and N-methylpiperazine there was obtained 1-methyl-4-[(7-oxo-8-phenyl-7H-thieno[2,3-a]quinolizin-10-yl)carbonyl]piperazine of m.p. 233°-234°;

(b) from 7-oxo-8-phenyl-7H-thieno[2,3-a]quinolizine-10-carboxylic acid and 3-hydroxypyrrolidine there was obtained 3-hydroxy-1-[(7-oxo-8-phenyl-7H-thieno[2,3-a]quinolizin-10-yl)carbonyl]pyrrolidine of m.p. 254°-257°;

(c) from 7-oxo-8-phenyl-7H-thieno[2,3-a]quinolizine-10-carboxylic acid and (S)-2-pyrrolidinemethanol there was obtained (S)-1-[7-oxo-8-phenyl-7H-thieno[2,3-a]quinolizin-10-yl)-carbonyl)-2-pyrrolidinemethanol of m.p. 140°-150° (dec.);

(d) from 7-oxo-8-phenyl-7H-thieno[2,3-a]quinolizine-10-carboxylic acid and 2-methoxyethylamine there was obtained N-(2-methoxyethyl)-6-oxo-8-phenyl-7H-thieno[2,3-a]quinolizine-10-carboxamide of m.p. 201°-203°;

(e) from 7-oxo-8-phenyl-7H-thieno[2,3-a]quinolizine-10-carboxylic acid and cis-2,6-dimethylmorpholine there was obtained cis-2,6-dimethyl-4-[(7-oxo-8-phenyl-7H-thieno[2,3-a]quinolizin-10-yl)carbonyl]morpholine of m.p. >280°;

(f) from 7-oxo-8-phenyl-7H-thieno[2,3-a]quinolizine-10-carboxylic acid and 4-piperidinol there was obtained 1-[(7-oxo-8-phenyl-7H-thieno[2,3-a]quinolizin-10-yl)carbonyl]-4-piperidinol of m.p. 241°-245° (dec.);

(g) from 7-oxo-8-phenyl-7H-thieno[2,3-a]quinolizine-10-carboxylic acid and 2-aminoethanol there was obtained N-(2-hydroxyethyl)-7-oxo-8-phenyl-7H-thieno[2,3-a]quinolizine-10-carboxamide of m.p. 219°-220°;

(h) from 7-oxo-8-phenyl-7H-thieno[2,3-a]quinolizine-10-carboxylic acid and 2-(ethylamino)ethanol there was obtained N-ethyl-N-(2-hydroxyethyl)-7-oxo-8-phenyl-7H-thieno[2,3-a]quinolizine-10-carboxamide of m.p. 208°-210°;

(i) from 7-oxo-8-phenyl-7H-thieno[2,3-a]quinolizine-10-carboxylic acid and 3-amino-2-propanol there was obtained N-(3-hydroxypropyl)-7-oxo-8-phenyl-7H-thieno[2,3-a]quinolizine-10-carboxamide of m.p. 228°-230°;

(j) from 7-oxo-8-phenyl-7H-thieno[2,3-a]quinolizine-10-carboxylic acid and 2-(methylamino)ethanol there was obtained N-(2-hydroxyethyl)-N-methyl-7-oxo-8-phenyl-7H-thieno[2,3-a]quinolizine-10-carboxamide of m.p. 231°-233°;

(k) from 7-oxo-8-phenyl-7H-thieno[2,3-a]quinolizine-10-carboxylic acid and N-ethylpiperazine there was obtained 1-ethyl-4-[(7-oxo-8-phenyl-7H-thieno[2,3-a]quinolizin-10-yl)carbonyl]piperazine of m.p. 214°-215° (dec);

(l) from 4-oxo-3-(α,α,α-trifluoro-m-tolyl)-4H-quinolizine-1-carboxylic acid and 3-hydroxypyrrolidine there was obtained 1-[(4-oxo-3-(α,α,α-trifluoro-m-tolyl)-4H-quinolizin-1-yl)carbonyl]-3-pyrrolidinol of m.p. 174°;

(m) from 7-oxo-8-phenyl-7H-thieno[2,3-a]quinolizine-10-carboxylic acid and (2S,4R)-4-hydroxy-pyrrolidinemethanol there was obtained (2S,4R)-1-[(7-oxo-8-phenyl-7H-thieno[2,3-a]quinolizin-10-yl)carbonyl]-4-hydroxy-2-pyrrolidinemethanol of m.p. 154°-161°.

EXAMPLE 48

0.64 ml of dimethyl sulfoxide is dissolved in 12 ml of methylene chloride and cooled to −70° under argon. 0.94 ml of trifluoroacetic acid anhydride in 2.2 ml of methylene chloride was added dropwise. 1.75 g of 3-hydroxy-1-[(7-oxo-8-phenyl-7H-thieno[2,3-a]quinolizin-10-yl]carbonyl]pyrrolidine were added portionwise after 10 minutes. The mixture was left to warm to room temperature after 10 minutes. After the addition of 10 ml of methylene chloride, the mixture was treated dropwise with 1.87 ml of triethylamine. A small amount of insoluble material was removed by filtration and the filtrate was washed several times with water, dried with sodium sulfate, filtered and evaporated. After chromatography on silica gel, the product was recrystallized from ethanol/N,N-dimethylformamide. There was obtained 1-[(7-oxo-8-phenyl-7H-thieno[2,3-a]quinazolin-10-yl)carbonyl]pyrrolidin-3-one as yellow crystals of m.p. 256°-261° (dec.).

EXAMPLE 49

(a) 6.3 g of 1-[(7-oxo-8-phenyl-7H-thieno[2,3-a]quinolizin-10-yl)carbonyl]-3-pyrrolidinol were suspended in 80 ml of N,N-dimethylformamide and cooled to 4° under argon. There were then added thereto in succession, 2.6 ml of ethyl iodide and 1.52 g of powdered potassium hydroxide (content about 90%), the cooling bath is removed and the mixture is stirred at room temperature for 3½ hours. After again adding the same amounts of reagents, the mixture is stirred further until the reaction was completed and poured into 800 ml of 10 percent sodium chloride solution which contains 25 ml of 1N hydrochloric acid. The yellow crystals were removed by filtration and dried. After chromatography on silica gel and recrystallization, there was obtained 3-ethoxy-1-[(7-oxo-8-phenyl-7H-thieno[2,3-a]quinolizin-10-yl)carbonyl]pyrrolidine of m.p. 167°-170°.

In an analogous manner, (b) from 1-[(7-oxo-8-phenyl-7H-thieno[2,3-a]quinolizin-10-yl)carbonyl]-3-pyrrolidinol and propyl iodide there was obtained 1-[(7-oxo-8-phenyl-7H-thieno[2,3-a]quinolizin-10-yl)carbonyl]-3-propoxy-pyrrolidine of m.p. 145°-147°;

(c) from (2S,4R)-2-(hydroxymethyl)-1-[(7-oxo-8-phenyl-7H-thieno[2,3-a]quinolizin-10-yl)carbonyl]-4-pyrrolidinol and methyl iodide there was obtained (2S,4R)-1-[(7-oxo-8-phenyl-7H-thieno[2,3-a]quinolizin-10-yl)carbonyl]-4-methoxy-2-(methoxymethyl)pyrrolidine of m.p. 166°-174°;

(d) from 1-[(7-oxo-8-phenyl-7H-thieno[2,3-a]quinolizin-10-yl)carbonyl]-3-pyrrolidinol and isopropyl iodide there was obtained 3-isopropoxy-1-[(7-oxo-8-phenyl-7H-thieno[2,3-a]quinolizin-10-yl)carbonyl]pyrrolidine of m.p. 116°-119°;

(e) from N-(trans-2-hydroxycyclohexyl)-7-oxo-8-phenyl-7H-thieno[2,3-a]quinolizine-10-carboxamide and methyl iodide there was obtained N-(trans-2-methoxycyclohexyl)-N-methyl-7-oxo-8-phenyl-7H-thieno[2,3-a]quinolizine-10-carboxamide of m.p. 204°-205°;

(f) from 2-(hydroxymethyl)-1-[(7-oxo-8-phenyl-7H-thieno[2,3-a]quinolizin-10-yl)carbonyl]piperidine and methyl iodide there was obtained 2-(methoxymethyl)-1-

[(7-oxo-8-phenyl-7H-thieno[2,3-a]quinolizin-10-yl)carbonyl]piperidine of m.p. 204°–207°;

(g) from (S)-1-[(7-oxo-8-phenyl-7H-thieno[2,3-a]quinolizin-10-yl)carbonyl]-2-azetidinemethanol and methyl iodide there was obtained (S)-2-(methoxymethyl)-1-[(7-oxo-8-phenyl-7H-thieno[2,3-a]quinolizin-10-yl)carbonyl]azetidine of m.p. 95°–100°.

EXAMPLE 50

(a) 32 g of methyl 10-chloro-6,7-dihydro-4-oxo-3-phenyl-4H-benzo[a]quinolizine-1-carboxylate were heated under reflux for 16 hours in 350 ml of carbon tetrachloride with 16 g of N-bromosuccinimide in the presence of 280 mg of dibenzoyl peroxide. The mixture is left to cool and 24.3 ml of triethylamine were added thereto. The mixture was then again heated under reflux for 3 hours. After cooling, the mixture was treated with about 900 ml of methylene chloride, and the organic phase was washed once with 550 ml of 1N hydrochloric acid and thereafter dried over sodium sulfate, filtered and evaporated. The residue was purified by chromatography on silica gel and was recrystallized from ethyl acetate. There was obtained methyl 10-chloro-4-oxo-3-phenyl-4H-benzo[a]quinolizine-1-carboxylate as yellow crystals of m.p. 169°–170°.

(b) In an analogous manner, from 1-(10-chloro-6,7-dihydro-4-oxo-3-phenyl-4H-benzo[a]quinolizin-1-yl)-4-methoxypiperidine there was obtained 1-[(10-chloro-3-phenyl-4-oxo-4H-benzo[a]quinolizin-1-yl)carbonyl]-4-methoxypiperidine of m.p. 158°–162°.

EXAMPLE 51

In analogy to the details in Example 49, (a) from 1-[(10-chloro-6,7-dihydro-4-oxo-3-phenyl-4H-benzo[a]quinolizin-1-yl)carbonyl]-4-piperidinol and methyl iodide there was obtained 1-[(10-chloro-6,7-dihydro-4-oxo-3-phenyl-4H-benzo[a]quinolizin-1-yl)carbonyl]-4-methoxypiperidine of m.p. 152°–153°;

(b) from 1-[(10-chloro-6,7-dihydro-4-oxo-3-phenyl-4H-benzo[a]quinolizin-1-yl)carbonyl]-3-pyrrolidinol and methyl iodide there was obtained 1-[(10-chloro-6,7-dihydro-4-oxo-3-phenyl-4-H-benzo[a]quinolizin-1-yl)carbonyl]-3-methoxypyrrolidine of m.p. 96°–98°;

(c) from 1-[(10-chloro-6,7-dihydro-4-oxo-3-phenyl-4H-benzo[a]quinolizin-1-yl)carbonyl]-3-pyrrolidinol and ethyl iodide there was obtained 1-[(10-chloro-6,7-dihydro-4-oxo-3-phenyl-4H-benzo[a]quinolizin-1-yl)carbonyl]-3-ethoxypyrrolidine of m.p. 133°–136°;

(d) from (S)-1-[[(10-chloro-6,7-dihydro-4-oxo-3-phenyl-4H-benzo[a]quinolizin-1-yl]carbonyl]-2-pyrrolidinemethanol and methyl iodide there was obtained (S)-1-[(10-chloro-6,7-dihydro-4-oxo-3-phenyl-4H-benzo[a]quinolizin-1-yl)carbonyl]-2-(methoxymethyl)pyrrolidine of m.p. 133°–135°;

(e) from 1-[(4,5-dihydro-7-oxo-8-phenyl-7H-thieno[2,3-a]quinolizin-10-yl)carbonyl]-3-pyrrolidinol and methyl iodide there was obtained 1-[(4,5-dihydro-7-oxo-8-phenyl-7H-thieno[2,3-a]quinolizin-10-yl)carbonyl]-3-methoxypyrrolidine of m.p. 155°–156°;

(f) from (S)-1-[(4,5-dihydro-7-oxo-8-phenyl-7H-thieno[2,3-a]quinolizin-10-yl)carbonyl]-2-pyrrolidinemethanol and methyl iodide there was obtained (S)-2-(methoxymethyl)-1-[(4,5-dihydro-7-oxo-8-phenyl-7H-thieno[2,3-a]quinolizin-10-yl)carbonyl]pyrrolidine of m.p. 129°–131°;

(g) from (R)-1-[(10-chloro-6,7-dihydro-4-oxo-3-phenyl-4H-benzo[a]quinolizin-1-yl)carbonyl]-2-pyrrolidinemethanol there was obtained (R)-1-[(10-chloro-6,7-dihydro-4-oxo-3-phenyl-4H-benzo[a]quinolizin-1-yl)carbonyl]-2-(methoxymethyl)pyrrolidine of m.p. 136°–138°;

(h) from 1-[(10-chloro-6,7-dihydro-4-oxo-3-phenyl-4H-benzo[a]quinolizin-1-yl)carbonyl]-4-piperidinol and ethyl iodide there was obtained 1-(10-chloro-6,7-dihydro-4-oxo-3-phenyl-4H-benzo[a]quinolizin-1-yl)-4-ethoxypiperidine of m.p. 142°–144°;

(i) from [(4,5-dihydro-7-oxo-8-phenyl-7H-thieno[2,3-a]quinolizin-10-yl)methyl]3-hydroxy-1-pyrrolidinecarboxylate and methyl iodide there was obtained (4,5-dihydro-7-oxo-8-phenyl-7H-thieno[2,3-a]quinolizin-10-yl)methyl 3-methoxy-1-pyrrolidinecarboxylate. M.S.: 436 (M).

EXAMPLE 52

The compound described in Example 31bd) can also be prepared as follows:

0.6 g of 3,4-dihydro-thieno[2,3-f][1,4]thiazepine-5(2H)-thione and 1.0 g of α-(tosylhydrazono)phenylacetyl chloride were stirred for a long time in 50 ml of methylene chloride at room temperature and in the presence of 0.84 ml of triethylamine. The solvent was removed in vacuo and the residue was chromatographed on silica gel. There was obtained 5,6-dihydro-8-hydroxy-9-phenyl-thiazolo[3,2-d]thieno[2,3-f][1,4]thiazepinium hydroxide (internal salt) of m.p. 190°–195°.

EXAMPLE 53

70.8 mg of 7-hydroxy-8-phenylthiazolo[3,2-a]thieno[2,3-c]pyridinium hydroxide (internal salt) and 38.2 ml of N-(2-methoxyethyl)-2-propynamide were heated for a long time in toluene under argon. The solvent was removed in vacuo and the residue was chromatographed on silica gel. After recrystallization from ethyl acetate, there was obtained N-(2-methoxyethyl)-7-oxo-8-phenyl-7H-thieno[2,3-a]quinolizine-10-carboxamide as yellow crystals of m.p. 201°–202°.

EXAMPLE 54

363 mg of methyl 10-chloro-4-oxo-3-phenyl-4H-benzo[a]quinolizine-1-carboxylate were hydrogenated at room temperature in 50 ml of ethyl acetate in the presence of 36 mg of 10 percent palladium/carbon. The catalyst was removed by filtration and the solvent was removed in vacuo. The residue was purified by chromatography on silica gel and the product was crystallized from methanol. There was obtained methyl 10-chloro-6,7-dihydro-4-oxo-3-phenyl-4H-benzo[a]quinolizine-1-carboxylate of m.p. 138°–139°.

EXAMPLE 55

432 mg of (R)-1-[(10-chloro-4-oxo-3-phenyl-4H-benzo[a]quinolizin-1-yl)carbonyl]-2-pyrrolidinemethanol and 4 mg of tetrabutylammonium iodide in 2 ml of methylene chloride were held in an ultrasound bath for 30 minutes with 104 mg of sodium hydroxide in 0.1 ml of water. 0.19 ml of dimethyl sulfate was then added. After about 1 hour, an additional 0.19 ml of dimethyl sulfate was added and the mixture was allowed to react for an additional 90 minutes. The mixture was diluted with methylene chloride, washed with water, dried over sodium sulfate, filtered and evaporated. The residue was chromatographed on silica gel and the product was recrystallized from cyclohexane/ethanol. There was obtained (R)-1-[(10-chloro-4-oxo-3-phenyl-4H-benzo[a]quinolizin-1-yl)carbonyl]-2-methoxymethylpyrrolidine as yellow crystals of m.p. 137°–140°.

EXAMPLE 56

(aa) 26.2 g of methyl 3-trifluoromethylphenylacetate were dissolved in 100 ml of diethyl ether and, after the addition of 8.2 ml of methyl formate, treated with 2.76 g of sodium. The mixture was stirred at room temperature until the reaction was completed and treated with 1N hydrochloric acid while cooling. The organic phase was separated and the aqueous phase was extracted twice with ether. The combined organic phases were washed with saturated sodium chloride solution, dried over sodium sulfate, filtered and evaporated. Distillation yielded methyl 3-hydroxy-2-($\alpha,\alpha,\alpha$-trifluoro-m-tolyl)acrylate as a colorless oil of b.p. 59°–62°/0.2 mm.

In an analogous manner, (ab) from methyl m-fluorophenylacetate and methyl formate there was obtained methyl 2-(m-fluorophenyl)-3-hydroxy-acrylate of b.p. 75°–81°/0.1 mm;

(ac) from methyl p-fluorophenylacetate and methyl formate there was obtained methyl 2-(p-fluorophenyl)-3-hydroxy-acrylate of b.p. 65°–70°/0.1 mm;

(ad) from methyl p-chlorophenylacetate and methyl formate there was obtained methyl 2-(p-chlorophenyl)-3-hydroxy-acrylate of m.p. 89°–97°.

(ba) 26 g of methyl 3-hydroxy-2-($\alpha,\alpha,\alpha$-trifluoro-m-tolyl)acrylate were dissolved in 1N sodium hydroxide solution while cooling in an ice-bath and treated with 10.6 ml of dimethyl sulfate. The mixture was stirred at about 0° for about 40 hours and an additional 40 ml of 1N sodium hydroxide solution and 3.8 ml of dimethyl sulfate were added. After the reaction was completed, the mixture was diluted with water and extracted with methylene chloride. After drying with sodium sulfate, the extract was distilled, whereby methyl 3-methoxy-2-($\alpha,\alpha,\alpha$-trifluoro-m-tolyl)-acrylate was obtained as a colorless oil of b.p. 75°–90°/0.2 mm.

In an analogous manner, (bb) from methyl 2-(m-fluorophenyl)-3-hydroxy-acrylate and dimethyl sulfate there was obtained methyl 2-(m-fluorophenyl)-3-methoxy-acrylate of b.p. 80°–100°/0.1 mm;

(bc) from methyl 2-(p-fluorophenyl)-3-hydroxy-acrylate and dimethyl sulfate there was obtained methyl 2-(p-fluorophenyl)-3-methoxy-acrylate of m.p. 70°–76°;

(bd) from methyl 2-(p-chlorophenyl)-3-hydroxy-acrylate and dimethyl sulfate there was obtained 2-(p-chlorophenyl)-3-methoxy-acrylate of m.p. 53°–58°.

(ca) 8.05 g of 3,4-dihydro-thieno[2,3-f][1,4]thiazepine-5(2H)-thione were suspended in 40 ml of methylene chloride and treated under argon with a solution of 7.1 ml of diethyl bromomalonate in 40 ml of methylene chloride. After stirring for 2.5 hours, 50 ml of 10 percent potassium hydrogen carbonate solution were added thereto and the mixture was stirred for 30 minutes. The organic phase was separated and the aqueous phase was extracted twice with methylene chloride. After drying with sodium sulfate, the extract was chromatographed on silica gel, whereby diethyl [3,4-dihydrothieno[2,3-f][1,4]thiazepine-8-(5H)-ylidene]malonate was obtained in the form of slightly yellowish crystals of m.p. 87°–89° (cyclohexane).

(cb) 2.56 g of diethyl [3,4-dihydrothieno[2,3-f][1,4]thiazepin-8(5H)-ylidene]malonate was suspended in 15.6 ml of ethanol and, after the addition of 4.3 ml of 2N ethanolic sodium methylate solution, the mixture was heated to reflux until the reaction was completed. The solvent was removed in vacuo and the residue was taken up in 60 ml of water and extracted several times with methylene chloride. After washing the organic phases with water and drying with sodium sulfate, they were chromatographed on silica gel. After recrystallization, there was obtained ethyl [6,7-dihydrothieno[2,3-f][1,4]thiazepine-8-(5H)-ylidene]acetate in the form of yellowish crystals, m.p. 86°–87° (ethanol).

(d) 255 mg of ethyl [6,7-dihydrothieno[2,3-f][1,4]thiazepin-8 (5H)-ylidene]acetate were treated portion wise under argon in 3 ml of tetrahydrofuran at 2°–3° with 44 mg of an about 55 percent sodium hydride dispersion and stirred for 20 minutes. A solution of methyl 3-methoxy-2-($\alpha,\alpha,\alpha$-trifluoro-m-tolyl)acrylate in 2 ml of tetrahydrofuran were added thereto. The cooling bath was removed and the solution was stirred at room temperature for 17 hours, then heated to 45°–50° for 2 hours and finally heated to reflux for 6 hours. The solution was acidified with ethereal hydrochloric acid solution and, after evaporation, chromatographed on silica gel. The mixture of the methyl and ethyl esters was now dissolved in 6 ml of methanol and 0.14 ml of 1N sodium methylate solution was added. The mixture was stirred at room temperature for about 20 hours, acidified with methanolic hydrochloric acid and evaporated. The residue was purified by recrystallization, whereby there was obtained methyl 5,6-dihydro-8-oxo-9-($\alpha,\alpha,\alpha$-trifluoro-m-tolyl)-8H-pyrido[1,2-d]thieno-[2,3-f][1,4]thiazepine-11-carboxylate as yellowish crystals, m.p. 190°–191° (ethyl acetate).

EXAMPLE 57

In analogy to the details in Example 32ba), (a) from 7-oxo-8-phenyl-7H-thieno[2,3-a]quinolizine-10-carboxylic acid and (R)-2-pyrrolidinemethanol there was obtained (R)-1-[(7-oxo-8-phenyl-7H-thieno[2,3-a]quinolizin-10-yl)carbonyl]-2-pyrrolidinemethanol of m.p. 146°–154°;

(b) from 7-oxo-8-phenyl-7H-thieno[2,3-a]quinolizine-10-carboxylic acid and 1-(2-methoxyethyl)-piperazine there was obtained 4-(2-methoxyethyl)-1-[(7-oxo-8-phenyl-7H-thieno[2,3-a]quinolizine-10-yl)carbonyl]piperazine of m.p. 166°–168°;

(c) from 7-oxo-8-phenyl-7H-thieno[2,3-a]quinolizine-10-carboxylic acid and (R)-3-hydroxypyrrolidine there was obtained (R)-1-[(7-oxo-8-phenyl-7H-thieno[2,3-a]quinolizin-10-yl)carbonyl]-3-pyrrolidinyl of m.p. 237°–239°;

(d) from 7-oxo-8-phenyl-7H-thieno[2,3-a]quinolizine-10-carboxylic acid and (S)-3-hydroxypyrrolidine there was obtained (S)-1-[(7-oxo-8-phenyl-7H-thieno[2,3-a]quinolizin-10-yl)carbonyl]-3-pyrrolidinyl of m.p. 237°–239°;

(e) from 7-oxo-8-phenyl-7H-thieno[2,3-a]quinolizine-10-carboxylic acid and 3-hydroxyazetidine there was obtained 1-[(7-oxo-8-phenyl-7H-thieno[2,3-a]quinolizine-10-yl)carbonyl]-3-azetidinol of m.p. 240°–241°;

(f) from 7-oxo-8-phenyl-7H-thieno[2,3-a]quinolizine-10-carboxylic acid and 3-hydroxypiperidine there was obtained 1-[(7-oxo-8-phenyl-7H-thieno[2,3-a]quinolizine-10-yl)carbonyl]-3-piperidinyl of m.p. 279°–280°;

(g) from 7-oxo-8-phenyl-7H-thieno[2,3-a]quinolizine-10-carboxylic acid and 2-(hydroxymethyl)-piperidine there was obtained 2-(hydroxymethyl)-1-[(7-oxo-8-phenyl-7H-thieno[2,3-a]quinolizine-10-yl)carbonyl]piperidine of m.p. 256°–258°;

(h) from 7-oxo-8-phenyl-7H-thieno[2,3-a]quinolizine-10-carboxylic acid and trans-2-amino-cyclohexanol there was obtained N-(trans-2-hydroxycyclohexyl)-7-oxo-8-phenyl-7H-thieno[2,3-a]quinolizine-10-carboxamide of m.p. 245°–246°;

(i) from 10-chloro-4-oxo-3-phenyl-4H-benzo[a]quinolizine-1-carboxylic acid and (S)-2-pyrrolidinemethanol there was obtained (S)-1-[(10-chloro-4-oxo-3-phenyl-4H-benzo[a]quinolizine-1-yl)-carbonyl]-2-pyrrolidinemethanol of m.p. 178°–180°;

(j) from 10-chloro-4-oxo-3-phenyl-4H-benzo[a]quinolizine-1-carboxylic acid and (R)-2-pyrrolidinemethanol there was obtained (R)-1-[(10-chloro-4-oxo-3-phenyl-4H-benzo[a]quinolizine-1-yl)carbonyl]-2-pyrrolidinemethanol of m.p. 178°–181°;

(k) from 7-oxo-8-phenyl-7H-thieno[2,3-a]quinolizine-10-carboxylic acid and furfurylamine there was obtained 7-oxo-8-phenyl-N-(2-furfuryl)-7H-thieno[2,3-a]quinolizine-10-carboxamide of m.p. 187°–188°;

(l) from 7-oxo-8-phenyl-7H-thieno[2,3-a]quinolizine-10-carboxylic acid and 2-amino-2-thiazoline there was obtained 7-oxo-8-phenyl-N-(2-thiazoline-2-yl)-7H-thieno[2,3-a]quinolizine-10-carboxamide of m.p. 172°–174°;

(m) from 7-oxo-8-phenyl-7H-thieno[2,3-a]quinolizine-10-carboxylic acid and 2-aminothiazole there was obtained 7-oxo-8-phenyl-N-(2-thiazolyl)-7H-thieno[2,3-a]quinolizine-10-carboxamide of m.p. 286°–289°;

(n) from 7-oxo-8-phenyl-7H-thieno[2,3-a]quinolizine-10-carboxylic acid and 3-chloropropylamine hydrochloride in the presence of a additional equivalent of triethylamine there was obtained N-(3-chloropropyl)-7-oxo-8-phenyl-7H-thieno[2,3-a]quinolizine-10-carboxamide of m.p. 196°–198°;

(o) from 7-oxo-8-phenyl-7H-thieno[2,3-a]quinolizine-10-carboxylic acid and 2-fluoroethylamine hydrochloride in the presence of an excess of triethylamine there was obtained N-(2-fluoroethyl)-7-oxo-8-phenyl-7H-thieno[2,3-a]quinolizine-10-carboxamide of m.p. 230°–232°;

(p) from 7-oxo-8-phenyl-7H-thieno[2,3-a]quinolizine-10-carboxylic acid and 3-methoxypropylamine there was obtained N-(3-methoxypropyl)-7-oxo-8-phenyl-7H-thieno[2,3-a]quinolizine-10-carboxamide of m.p. 188°–189°;

(q) from 7-oxo-8-phenyl-7H-thieno[2,3-a]quinolizine-10-carboxylic acid and bis-(2-methoxyethyl)-amine there was obtained N,N-bis-(2-methoxyethyl)-7-oxo-8-phenyl-7H-thieno[2,3-a]quinolizine-10-carboxamide of m.p. 152°;

(r) from 7-oxo-8-phenyl-7H-thieno[2,3-a]quinolizine-10-carboxylic acid and N-(2-methoxyethyl)-aniline there was obtained N-(2-methoxyethyl)-7-oxo-8-phenyl-7H-thieno[2,3-a]quinolizine-10-carboxanilide of m.p. 143°–147°;

(s) from 10-chloro-4-oxo-3-phenyl-4H-benzo[1-]quinolizine-1-carboxylic acid and 3-hydroxy-azetidine there was obtained 1-[(10-chloro-4-oxo-3-phenyl-4H-benzo[a]quinolizin-1-yl)carbonyl]-3-azetidinol of m.p. 246°–247°.

EXAMPLE 58

A suspension of 0.676 g of 6,7-dihydro-1-(hydroxymethyl)-3-phenyl-10-chloro-4H-benzo[a]quinolizine-4-one in 18 ml of dioxane was treated with 0.6 ml of phenyl chloroformate and 0.42 ml of pyridine and stirred at room temperature for 3 hours. 1.03 g of aminoacetonitrile were then added and the mixture was stirred at 100° until carbonate was no longer present according to thin-layer chromatography. After evaporation, the residue was taken up in chloroform, washed twice with water and saturated sodium chloride solution, dried over magnesium sulfate and concentrated. Chromatography over silica gel [elution agent toluene/dioxane (9:1)] gave [[(10-chloro-6,7-dihydro-4-oxo-3-phenyl-4H-benzo[a]quinolizine-1-yl)methyl]amino]acetonitrile of m.p. 181°–183° (from methanol) as well as in a second fraction (10-chloro-6,7-dihydro-4-oxo-3-phenyl-4H-benzo[a]quinolizine-1-yl)methyl-(cyanomethyl)carbamate of m.p. 166°–167° (from toluene).

EXAMPLE 59

A suspension of 0.376 g of [[(10-chloro-6,7-dihydro-4-oxo-3-phenyl-4H-benzo[a]quinolizine-1-yl)methyl]amino]acetonitrile in 10 ml of tetrahydrofuran was treated with 0.1 ml of formic acid-acetic acid anhydride and the clear yellow solution which formed after a short time was stirred at room temperature for 45 minutes. After evaporation the residue was taken up in chloroform, washed with 10 percent potassium bicarbonate solution and saturated sodium chloride solution, dried over magnesium sulfate, concentrated and purified by chromatography on silica gel with toluene/dioxane (9:1). N-[(10-Chloro-6,7-dihydro-4-oxo-3-phenyl-4H-benzo[a]quinolizine-1-yl)methyl]-N-(cyanomethyl)formamide formed a yellow resin.

EXAMPLE 60

(a) 13.5 g of lithium aluminum hydride were suspended at about 0° in 550 ml of absolute tetrahydrofuran under argon and thereupon there was added portionwise within about a half hour methyl (S)-azetidine-2-carboxylate hydrochloride. The mixture was stirred at about 5° for 30 minutes, then at about 20° for 3 hours. Thereafter, the mixture was again cooled and 60 ml of water were added dropwise. After stirring at room temperature for 3 days, the white precipitate was removed by filtration and extracted exhaustively with chloroform. The filtrate was evaporated and distilled in vacuo together with the extract obtained above. There was obtained (S)-2-azetidinemethanol as a colorless oil of b.p. 44°–46°/0.06 Torr.

(b) In analogy to the details in Example 32ba), from 7-oxo-8-phenyl-7H-thieno[2,3-a]quinolizine-10-carboxylic acid and (S)-2-azetidinemethanol there was obtained (S)-1-[(7-oxo-8-phenyl-7H-thieno[2,3-a]quinolizine-10-yl)carbonyl]-2-azetidinemethanol of m.p. 158°–161°.

EXAMPLE 61

(a) 3.0 g of methyl α-pyridineacetate were dissolved in 27 ml of tetrahydrofuran under argon and cooled to about 2°. 0.87 g of an about 55 percent sodium hydride dispersion in oil was then added portionwise, the mixture was stirred for an additional 15 minutes and a solution of methyl 3-methoxy-2-(α,α,α-trifluoro-m-tolyl)acrylate in 27 ml of tetrahydrofuran was added dropwise. The mixture was left to warm to room temperature and the solution, which has an intensive yellow color, was poured into 220 ml of water. The mixture was acidified to pH 4 with 2N hydrochloric acid, the crystals were removed by filtration and washed with n-hexane. After recrystallization from ethyl acetate, there was obtained methyl 4-oxo-3-(α,α,α-trifluoro-m-tolyl)-4H-quinolizine-1-carboxylate as yellow crystals of m.p. 147°–148°.

In an analogous manner, (b) from methyl 3-methoxy-2-phenyl-acrylate and methyl α-pyridylacetate there was obtained methyl 4-oxo-3-phenyl-4H-quinolizine-1-carboxylate of m.p. 139°–140°;

(c) from methyl 2-(m-fluorophenyl)-3-methoxy-acrylate and methyl α-pyridylacetate there was obtained methyl 3-(m-fluorophenyl)-4-oxo-4H-quinolizine-1-carboxylate of m.p. 159°–161°;

(d) from methyl 2-(p-fluorophenyl)-3-methoxy-acrylate and methyl α-pyridylacetate there was obtained methyl 3-(p-fluorophenyl)-4-oxo-4H-quinolizine-1-carboxylate of m.p. 141°–142°;

(e) from methyl 2-(p-chlorophenyl)-3-methoxy-acrylate and methyl α-pyridylacetate there was obtained methyl 3-(p-chlorophenyl)-4-oxo-4H-quinolizine-1-carboxylate of m.p. 179°–180°.

EXAMPLE 62

(a) 0.25 g of methyl 4-oxo-3-(α,α,α-trifluoro-m-tolyl)-4H-quinolizine-1-carboxylate was suspended in 3 ml of ethanol and treated with 3 ml of 1N sodium hydroxide solution. The mixture was heated to reflux until the reaction has finished. 13 ml of water were added and the mixture was acidified with 1N hydrochloric acid. The yellow crystals were removed by filtration and dried. After recrystallization from ethyl acetate, there was obtained 4-oxo-3-(α,α,α-trifluoro-m-tolyl)-4H-quinolizine-1-carboxylic acid as yellow crystals of m.p. 228°–229°.

(b) 0.83 g of 4-oxo-3-(α,α,α-trifluoro-m-tolyl)-4H-quinolizine-1-carboxylic acid was heated to reflux in a mixture of 13 ml of concentrated hydrochloric acid and 6.5 ml of acetic acid until the reaction was completed. The solution was evaporated, whereupon 10 ml of water are added. The crystals were removed by filtration and dried. After chromatography on silica gel and recrystallization, there was obtained 3-(α,α,α-trifluoro-m-tolyl)-4H-quinolizin-4-one as yellow crystals of m.p. 110°–111° (n-hexane/toluene).

EXAMPLE A

Compound A (10-chloro-6,7-dihydro-N-(2-methoxyethyl)-4-oxo-3-phenyl-4H-benzo[a]quinolizine-1-carboxamide) can be used in a known manner as the active substance for the preparation of pharmaceutical preparations of the following composition:

| (a) Tablets | mg/tablet |
|---|---|
| Compound A | 5 |
| Lactose | 135 |
| Maize starch | 51 |
| Polyvinylpyrrolidine | 8 |
| Magnesium stearate | 1 |
| Tablet weight | 200 |

| (b) Capsules | mg/capsule |
|---|---|
| Compound A | 10 |
| Lactose | 30 |
| Maize starch | 8.5 |
| Talc | 1 |
| Magnesium stearate | 0.5 |
| Capsule fill weight | 50 |

Compounds B-Y listed hereinafter can also be used as the active substance:

B = 1-[(10-Chloro-6,7-dihydro-4-oxo-3-phenyl-4H-benzo[a]quinolizin-1-yl)carbonyl]-4-piperidinol.
C = (4,5-Dihydro-7-oxo-8-phenyl-7H-thieno[2,3-a]quinolizin-10-yl)methyl 4-morpholinecarboxylate.
D = 4-[(6,7-Dihydro-4-oxo-3-phenyl-10-chloro-4H-benzo[a]quinolizin-1-yl)carbonyl]-2,6-dimethylmorpholine.
E = (S)-1-[(7-Oxo-8-phenyl-7H-thieno[2,3-a]quinolizin-10-yl)carbonyl]-2-pyrrolidinemethanol.
F = (S)-2-Methoxymethyl-1-[(7-oxo-8-phenyl-7H-thieno-[2,3-a]quinolizin-10-yl)carbonyl]pyrrolidine.
G = 1-[(10-Chloro-4-oxo-3-phenyl-4H-benzo[a]quinolizine-1-yl)carbonyl]-3-methoxypyrrolidine.
H = (S)-1-[(10-Chloro-4-oxo-3-phenyl-4H-benzo[a]quinolizin-1-yl)carbonyl]-2-pyrrolidinemethanol.
I = cis-4-[(4,5-Dihydro-7-oxo-8-phenyl-7H-thieno[2,3-a]quinolizin-10-yl)carbonyl]-2,6-dimethylmorpholine.
K = 1-(10-Chloro-6,7-dihydro-4-oxo-3-phenyl-4H-benzo[a]quinolizin-1-yl)-4-methoxypiperidine.
L = 1-[(10-Chloro-3-phenyl-4-oxo-4H-benzo[a]quinolizin-1-yl)carbonyl]-4-methoxypiperidine.
M = N-Ethyl-N-(2-methoxyethyl)-7-oxo-8-phenyl-7H-thieno[2,3-a]quinolizine-10-carboxamide.
N = N-(2-Methoxyethyl)-N-methyl-7-oxo-8-phenyl-7H-thieno[2,3-a]quinolizine-10-carboxamide.
O = (R)-2-(Methoxymethyl)-1-[(7-oxo-8-phenyl-7H-thieno[2,3-a]quinolizin-10-yl)carbonyl]pyrrolidine.
P = 1-[(10-Chloro-6,7-dihydro-4-oxo-3-phenyl-4H-benzo[a]quinolizin-1-yl)carbonyl]-3-methoxypyrrolidine.
Q = 1-[(10-Chloro-6,7-dihydro-4-oxo-3-phenyl-4H-benzo[a]quinolizin-1-yl)carbonyl]-3-ethoxypyrrolidine.
R = (R)-3-Methoxy-1-[(7-oxo-8-phenyl-7H-thieno[2,3-a]quinolizin-10-yl)carbonyl]pyrrolidine.
S = (S)-3-Methoxy-1-[(7-oxo-8-phenyl-7H-thieno[2,3-a]quinolizin-10-yl)carbonyl]pyrrolidine.
T = (S)-1-[(10-Chloro-6,7-dihydro-4-oxo-3-phenyl-4H-benzo[a]quinolizin-1-yl)carbonyl]-2-(methoxymethyl)pyrrolidine.
U = 1-[(4,5-Dihydro-7-oxo-8-phenyl-7H-thieno[2,3-a]quinolizin-10-yl)carbonyl]-3-methoxypyrrolidine.
V = 3-Methoxy-1-[(7-oxo-8-phenyl-7H-thieno[2,3-a]quinolizin-10-yl)carbonyl]azetidine.
W = (R)-1-[(10-Chloro-4-oxo-3-phenyl-4H-benzo[a]quinolizin-1-yl)carbonyl]-2-pyrrolidinemethanol.
X = (S)-1-[(10-Chloro-4-oxo-3-phenyl-4H-benzo[a]quinolizin-1-yl)carbonyl]-2-(methoxymethyl)pyrrolidine.
Y = (R)-1-[(10-Chloro-4-oxo-3-phenyl-4H-benzo[a]quinolizin-1-yl)carbonyl]-2-(methoxymethyl)pyrrolidine.

We claim:

1. A compound of the formula

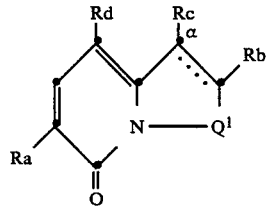

I wherein $Q^1$ and the nitrogen atom taken together is a group of the formula >N—CH$_2$CH$_2$— or >N—CH=CH—, Ra is phenyl, pyridyl or thienyl group which can be substituted by halogen, trifluoromethyl, nitro, lower alkyl or lower alkoxy, Rb and Rc together with the carbon atom denoted by α are a group of the formula >C$_\alpha$—CH=CH—CH=CH— which may be substituted by halogen, trifluoromethyl, lower alkyl, lower alkoxy, nitro, amino or mono- or di(lower alkyl)amino, and the dotted line signifies an additional bond, Rd is the group of the formula

wherein $R^1$ is hydroxy, lower alkoxy, a group of the formula —$NR^3R^4$ or an unsubstituted 5-membered, saturated, partially unsaturated or aromatic heterocycle selected from the group consisting of 2-oxazolyl, 1,2,4-oxadiazolyl, 2-thiazolyl, and 2-tetrahydrofuryl; which is attached via a carbon atom and which can be substituted by one or two lower alkyl groups and can be substituted by a $(C_{3-6})$-cyclo-alkyl, hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or alkylenedioxy group, $R^3$ and $R^4$ each, independently, is hydrogen, lower alkyl, lower alkoxyalkyl, lower dialkoxyalkyl, lower alkyl substituted by lower alkylenedioxy; lower cyanoalkyl, lower haloalkyl, lower hydroxyalkyl, lower dihydroxyalkyl, lower alkanoyl, lower alkoxycarbonyl or a $(C_{3-7})$-cycloalkyl group which can be substituted by hydroxy, lower alkoxy, lower alkanoyloxy, lower hydroxyalkyl, lower alkoxyalkyl, lower alkanoyloxyalkyl, oxo, carbamoyl, mono- or di(lower alkyl)carbamoyl or by lower alkylenedioxy or together with the nitrogen atom are an unsubstituted 3- to 7-membered, saturated N-heterocycle selected from the group consisting of azetidinyl, pyrrolidinyl, morpholinyl, thiomorpholinyl, piperazinyl, and piperidinyl; which can be substituted by one or two lower alkyl groups and can be substituted by one or two hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or lower alkylenedioxy groups and which can contain as a ring member an oxygen or sulfur atom or the group >N-$R^5$, and $R^5$ is hydrogen, lower alkyl, lower hydroxyalkyl, lower alkoxyalkyl, lower alkanoyloxyalkyl, lower alkanoyl, lower alkoxycarbonyl, carbamoyl or mono- or di(lower alkyl)carbamoyl, or a pharmaceutically acceptable acid addition salt of a compound of formula I which has one or more basic substituents.

2. A compound, in accordance with claim 1, wherein Ra is unsubstituted phenyl or phenyl substituted by halogen, trifluoromethyl, nitro, lower alkyl or lower alkoxy, Rb and Rc together with the carbon atom denoted by α is a group of the formula >$C_\alpha$—CH=CH—CH=CH— which is unsubstituted or substituted by halogen, trifluoromethyl, lower alkyl, lower alkoxy, nitro, amino or mono- or di(lower alkyl)amino and the dotted line is an additional bond, a group of the formula —$NR^3R^4$ or an unsubstituted 5-membered, partially unsaturated or aromatic heterocycle selected for the group consisting of 2-oxazolyl, 1,2,4-oxadiazolyl, 2-thiazolyl, and 2-tetrahydrofuryl; which is attached via a carbon atom and which can be substituted by one or two lower alkyl groups, $R^3$ and $R^4$ each, independently, are hydrogen, lower alkyl, $(C_{5-6})$-cycloalkyl or lower alkoxycarbonyl or together with the nitrogen atoms are an unsubstituted 5- or 6-membered, saturated N-heterocycle selected from the group consisting of azetidinyl, pyrrolidinyl, morpholinyl, thiomorpholinyl, piperazinyl, and piperidinyl; which can be substituted by one or two lower alkyl groups and which can be substituted on a carbon atom by oxo, hydroxy, lower alkoxy, lower alkoxyalkyl, lower hydroxyalkyl, lower alkoxy-carbonyl, carbamoyl or mono- or di(lower alkyl)carbamoyl or which can contain as a ring member an oxygen or sulfur atom or the group >N—$R^5$, and $R^5$ is hydrogen, lower alkyl, lower hydroxyalkyl, lower alkoxyalkyl, lower alkanoyl, lower alkoxycarbonyl, carbamoyl or mono- pr di(lower alkyl)carbamoyl.

3. A compound in accordance with claim 2 wherein Ra is unsubstituted phenyl or phenyl substituted by m-halogen or m-trifluoromethyl.

4. A compound in accordance with claim 3, wherein Ra is phenyl.

5. A compound in accordance with claim 4, wherein Rb and Rc taken together with the carbon atom denoted by α are a group of the formula >$C_\alpha$—CH=CH—CH=CH— which can be substituted by halogen, and the dotted line is an additional bond.

6. A compound in accordance with claim 5, wherein Rb and Rc taken together with the carbon atom denoted by α are the group of the formula >$C_\alpha$—CH=C-Cl—CH=CH—.

7. A compound in accordance with claim 6, wherein $R^1$ is the group —$NR^3R^4$, $R^3$ is lower alkoxyalkyl and $R^4$ is hydrogen or lower alkyl or $R^3$ and $R^4$ together with the nitrogen atom is an unsubstituted 4-, 5- or 6-membered saturated N-heterocycle selected from the group consisting of azetidinyl, pyrrolidinyl, morpholinyl, thiomorpholinyl, piperazinyl, and piperidinyl; which can be substituted by one or two lower alkyl groups and which can be substituted by a hydroxy, lower alkoxy, lower hydroxyalkyl or lower alkoxyalkyl group and which can contain as a ring member an oxygen atom.

8. A compound in accordance with claim 7, wherein $R^3$ is lower alkoxyalkyl and $R^4$ is hydrogen or lower alkyl or $R^3$ and $R^4$ taken together with the nitrogen atom are a 1-azetidinyl, 1-pyrrolidinyl, 1-piperidinyl or 4-morpholinyl group which can be substituted by one or two lower alkyl groups and which can be substituted by a hydroxy, lower alkoxy, lower hydroxyalkyl or lower alkoxyalkyl group.

9. A compound in accordance with claim 8, wherein $R^3$ is 2-(lower alkoxy)ethyl and $R^4$ is hydrogen or lower alkyl or $R^3$ and $R^4$ taken together with the nitrogen atom are 3-(lower alkoxy)-1-azetidinyl, 3-(lower alkoxy)-1-pyrrolidinyl, 2-(lower alkoxyalkyl)-1-pyrrolidinyl, 2-(lower hydroxyalkyl)-1-pyrrolidinyl, 4-hydroxy-1-piperidinyl, 4-(lower alkoxy)-1-piperidinyl; 4-morpholinyl or 2,6-di(lower alkyl)-4-morpholinyl.

10. A compound in accordance with claim 6, wherein m and q are O, n is 1 and $R^1$ is hydroxy or lower alkoxy.

11. A compound, in accordance with claim 1, 10-chloro-6,7-dihydro-N-(2-methoxyethyl)-4-oxo-3-phenyl-4H-benzo[a]quinolizine-1-carboxamide.

12. A compound, in accordance with claim 1, 1-[(10-chloro-6,7-dihydro-4-oxo-3-phenyl-4H-benzo-[a]-quinolizine-1-yl)carbonyl]-4-piperidinyl.

13. A compound, in accordance with claim 1, 4-[(6,7-dihydro-4-oxo-3-phenyl-10-chloro-4H-benzo-[a]-quinolizin-1-yl)carbonyl]-2,6-dimethylmorpholine.

14. A compound, in accordance with claim 1, 1-[(10-chloro-4-oxo-3-phenyl-4H-benzo[a]quinolizin-1-yl)-carbonyl]-3-methoxypyrrolidine.

15. A compound, in accordance with claim 1, (S)-1-[(10-chloro-4-oxo-3-phenyl-4H-benzo[a]quinolizin-1-yl)carbonyl]-2-pyrrolidinemethanol.

16. A compound, in accordance with claim 1, 1-[(10-chloro-3-phenyl-4-oxo-4H-benzo[a]quinolizine-1-yl)carbonyl]-4-methoxypiperidine.

17. A compound, in accordance with claim 1, 1-[(10-chloro-6,7-dihydro-4-oxo-3-phenyl-4H-benzo[a]quinolizin-1-yl)carbonyl]-3-methoxypyrrolidine.

18. A compound, in accordance with claim 1, 1-[(10-chloro-6,7-dihydro-4-oxo-3-phenyl-4H-benzo[a]quinolizin-1-yl)carbonyl]-3-ethoxypyrrolidine.

19. A compound, in accordance with claim 1, (S)-1-[(10-chloro-6,7-dihydro-4-oxo-3-phenyl-4H-benzo[a]quinolizin-1-yl)carbonyl]-2-(methoxymethyl)pyrrolidine.

20. A compound, in accordance with claim 1, (R)-1-[(10-chloro-4-oxo-3-phenyl-4H-benzo[a]quinolizin-1-yl)carbonyl]-2-pyrrolidinemethanol.

21. A compound, in accordance with claim 1, (S)-1-[(10-chloro-4-oxo-3-phenyl-4H-benzo[a]quinolizin-1-yl)carbonyl]-2-(methoxymethyl)pyrrolidine.

22. A compound, in accordance with claim 1, (R)-1-[(10-chloro-4-oxo-3-phenyl-4H-benzo[a]quinolizin-1-yl)carbonyl]-2-(methoxymethyl)pyrrolidine.

23. A method of treating muscle tension, stress, insomnia, anxiety or convulsions which comprises administering to a host requiring such treatment an effective amount of a compound of the formula

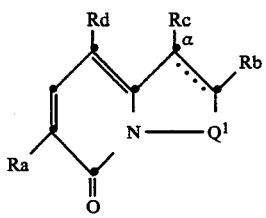   I wherein $Q^1$ and the nitrogen atom taken together is a group of the formula $>N-CH_2CH_2-$ or $>N-CH=CH-$, Ra is phenyl, pyridyl or thienyl group which can be substituted by halogen, trifluoromethyl, nitro, lower alkyl or lower alkoxy, Rb and Rc together with the carbon atom denoted by α are a group of the formula $>C_\alpha-CH=CH-CH=CH-$ which may be substituted by halogen, trifluoromethyl, lower alkyl, lower alkoxy, nitro, amino or mono- or di(lower alkyl)amino, and the dotted line signifies an additional bond, Rd is the group of the formula

wherein $R^1$ is hydroxy, lower alkoxy, a group of the formula $-NR^3R^4$ or an unsubstituted 5-membered, saturated, partially unsaturated or aromatic heterocycle selected from the group consisting of 2-oxazolyl, 1,2,4-oxadiazolyl, 2-thiazolyl, and 2-tetrahydrofuryl which is attached via a carbon atom and which can be substituted by one or two lower alkyl groups and can be substituted by a $(C_{3-6})$-cycloalkyl, hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or alkylenedioxy group, $R^3$ and $R^4$ each, independently, is hydrogen, lower akyl, lower alkoxyalkyl, lower dialkoxyalkyl, lower alkyl substituted by lower alkylenedioxy, lower cyanoalkyl, lower haloalkyl, lower hydroxyalkyl, lower dihydroxyalkyl, lower alkanoyl, lower alkoxycarbonyl or a $(C_{3-7})$-cycloalkyl group which can be substituted by hydroxy, lower alkoxy, lower alkanoyloxy, lower hydroxyalkyl, lower alkoxyalkyl, lower alkanoyl-oxyalkyl, oxo, carbamoyl, mono- or di(lower alkyl)carbamoyl or by lower alkylenedioxy or together with the nitrogen atom are an unsubstituted 3- or 7-membered, saturated N-heterocycle selected from the group consisting of azetidinyl, pyrrolidinyl, morpholinyl, thiomorpholinyl, piperazinyl, and piperidinyl which can be substituted by one or two lower alkyl groups and can be substituted by one or two hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or lower alkylenedioxy groups and which can contain as a ring member an oxygen or sulfur atom or the group $>N-R^5$, and $R^5$ is hydrogen, lower alkyl, lower hydroxyalkyl, lower alkoxyalkyl, lower alkanoyloxyalkyl, lower alkanoyl, lower alkoxycarbonyl, carbamoyl or mono- or di(lower alkyl)-carbamoyl, or a pharmaceutically acceptable acid addition salt of a compound of formula I which has one or more basic substituents.

24. A pharmaceutical composition comprising an effective amount of a compound of the formula

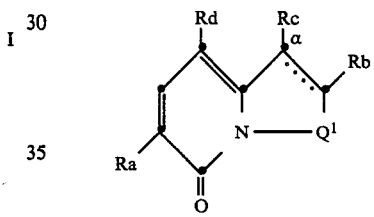   I wherein $Q^1$ and the nitrogen atom taken together is a group of the formula $>N-CH_2CH_2-$ or $>N-CH=CH-$, Ra is phenyl, pyridyl or thienyl group which can be substituted by halogen, trifluoro-methyl, nitro, lower alkyl or lower alkoxy, Rb and Rc together with the carbon atom denoted by α are a group of the formula $>C_\alpha-CH=CH-CH=CH-$ which may be substituted by halogen, trifluoromethyl, lower alkyl, lower alkoxy, nitro, amino or mono- or di(lower alkyl)amino, and the dotted line signifies an additional bond, Rd is the group of the formula

wherein $R^1$ is hydroxy, lower alkoxy, a group of the formula $-NR^3R^4$ or an unsubstituted 5-membered, saturated, partially unsaturated or aromatic heterocycle selected from the group consisting of 2-oxazolyl, 1,2,4-oxadiazolyl, 2-thiazolyl, and 2-tetrahydrofuryl which is attached via a carbon atom and which can be substituted by one or two lower alkyl groups and can be substituted by a $(C_{3-6})$cycloalkyl, hydroxyl, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or alkylenedioxy group, $R^3$ and $R^4$ each, independently, is hydrogen, lower alkyl, lower alkoxyalkyl, lower dialkoxyalkyl, lower alkylenedioxyalkyl, lower cyanoalkyl, lower haloalkyl, lower hydroxyalkyl, lower dihydroxyalkyl, lower alkanoyl, lower alkoxycarbonyl or a $(C_{3-7})$-cycloalkyl group which can be substituted by hydroxy, lower alkoxy, lower alkanoyloxy, lower hydroxyalkyl, lower alkoxyalkyl, lower alkanoyl-oxyalkyl, oxo, carbamoyl, mono- or di(lower alkyl)carbamoyl or by lower alkylenedioxy or together with the nitrogen atom are an unsubstituted 3- to 7-membered, saturated N-heterocycle selected from the group consisting of azetidinyl, pyrrolidinyl, morpholinyl, thiomorpholinyl, piperazinyl, and piperidinyl which can be substituted by one or two lower alkyl groups and can be substituted by one or two hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or lower alkylenedioxy groups and which can contain as a ring member an oxygen or sulfur atom or the group $>N-R^5$, and $R^5$ is hydrogen, lower alkyl, lower hydroxyalkyl, lower alkoxyalkyl, lower alkanoyloxyalkyl, lower alkanoyl, lower alkoxycarbonyl, carbamoyl or mono- or di(lower alkyl)carbamoyl, or a pharmaceutically acceptable acid addition salt of a compound of formula I which has one or more basic substituents, and an inert pharmaceutical carrier.

25. A pharmaceutical composition, in accordance with claim 24, wherein Ra is unsubstituted phenyl or phenyl substituted by halogen, trifluromethyl, nitro, lower alkyl or lower alkoxy, Rb and Rc together with the carbon atom denoted by α is a group of the formula $>C_\alpha-CH=CH-CH=CH-$ which is unsubstituted or substituted by halogen, trifluoromethyl, lower alkyl, lower alkoxy, nitro, amino or mono- or di(lower alkyl)amino and the dotted line is an additional bond, a group of the formula $-NR^3R^4$ or an unsubstituted 5-membered, partially unsaturated or aromatic heterocycle which is attached via a carbon atom and which can be substituted by one or two lower alkyl groups, $R^3$ and $R^4$ each, independently, are hydrogen, lower alkyl, $(C_{5-6})$-cyclo-alkyl or lower alkoxycarbonyl or together with the nitrogen atoms are an unsubstituted 5- or 6-membered, saturated N-heterocycle which can be substituted by one or two lower alkyl groups and which can be substituted on a carbon atom by oxo, hydroxy, lower alkoxy, lower alkoxyalkyl, lower hydroxyalkyl, lower alkoxycarbonyl, carbamoyl or mono- or di(lower alkyl)carbamoyl or which can contain as a ring member an oxygen or sulfur atom or the group $>N-R^5$, and $R^5$ is hydrogen, lower alkyl, lower hydroxyalkyl, lower alkoxyalkyl, lower alkanoyl, lower alkoxycarbonyl, carbamoyl or mono- pr di(lower alkyl)carbamoyl.

26. A pharmaceutical composition in accordance with claim 25, wherein Ra is unsubstituted phenyl or phenyl substituted by m-halogen or m-trifluoromethyl.

27. A pharmaceutical composition in accordance with claim 26, wherein Rb and Rc taken together with the carbon atom denoted by α are the group of the formula $-CH=CCl-CH=CH-$.

28. A pharmaceutical composition in accordance with claim 27, wherein $R^1$ is the group $-NR^3R^4$, $R^3$ is lower alkoxyalkyl and $R^4$ is hydrogen or lower alkyl or $R^3$ and $R^4$ together with the nitrogen atom is an unsubstituted 4-, 5- or 6-membered saturated N-heterocycle which can be substituted by one or two lower alkyl groups and which can be substituted by a hydroxy, lower alkoxy, lower hydroxyalkyl or lower alkoxyalkyl group and which can contain as a ring member an oxygen atom.

29. A pharmaceutical composition in accordance with claim 28, wherein $R^3$ is 2-(lower alkoxy)ethyl and $R^4$ is hydrogen or lower alkyl or $R^3$ and $R^4$ taken together with the nitrogen atom are 3-(lower alkoxy)-1-azetidinyl, 3-(lower alkoxy)-1-pyrrolidinyl, 2-(lower alkoxyalkyl)-1-pyrrolidinyl, 2-(lower hydroxyalkyl)-1-pyrrolidinyl, 4-hydroxy-1-piperidinyl, 4-(lower alkoxy)-1-piperidinyl, 4-morpholinyl or 2,6-di(lower alkyl)-4-morpholinyl.

30. A method, in accordance with claim 23, wherein Ra is unsubstituted phenyl or phenyl substituted by halogen, trifluoromethyl, nitro, lower alkyl or lower alkoxy, Rb and Rc together with the carbon atom denoted by α is a group of the formula $>C_\alpha-CH=CH-CH=CH-$ which is unsubstituted or substituted by halogen, trifluoromethyl, lower alkyl, lower alkoxy, nitro, amino or mono- or di(lower alkyl)amino and the dotted line is an additional bond, a group of the formula $-NR^3R^4$ or an unsubstituted 5-membered, partially unsaturated or aromatic heterocycle selected from the group consisting of 2-oxazolyl, 1,2,4-oxadiazolyl, 2-thiazolyl, and 2-tetrahydrofuryl which is attached via a carbon atom and which can be substituted by one or two lower alkyl groups, $R^3$ and $R^4$ each, independently, are hydrogen, lower alkyl, $(C_{5-6})$-cycloalkyl or lower alkoxycarbonyl or together with the nitrogen atoms are an unsubstituted 5- or 6-membered, saturated N-heterocycle selected from the group consisting of azetidinyl, pyrrolidinyl, morpholinyl, thiomorpholinyl, piperazinyl, and piperidinyl which can be substituted by one or two lower alkyl groups and which can be substituted on a carbon atom by oxo, hydroxyl, lower alkoxy, lower alkoxyalkyl, lower hydroxyalkyl, lower alkoxycarbonyl, carbamoyl or mono- or di(lower alkyl)carbamoyl or which can contain as a ring member an oxygen or sulfur atom or the group $>N-R^5$, and $R^5$ is hydrogen, lower alkyl, lower hydroxyalkyl, lower alkoxyalkyl, lower alkanoyl, lower alkoxycarbonyl, carbamoyl or mono- or pr di(lower alkyl)carbamoyl.

31. A method in accordance with claim 30, wherein Ra is unsubstituted phenyl or phenyl substituted by m-halogen or m-trifluoromethyl.

32. A method in accordance with claim 31, wherein Rb and Rc taken together with the carbon atom denoted by α are the group of the formula $-CH=CCl-CH=CH-$.

33. A method in accordance with claim 32, wherein $R^1$ is the group $-NR^3R^4$, $R^3$ is lower alkoxyalkyl and $R^4$ is hydrogen or lower alkyl or $R^3$ and $R^4$ together with the nitrogen atom is an unsubstituted 4-, 5- or 6-membered saturated N-heterocycle selected from the group consisting of azetidinyl, pyrrolidinyl, morpholinyl, thiomorpholinyl, piperazinyl, and piperidinyl which can be substituted by one or two lower alkyl groups and which can be substituted by a hydroxy, lower alkoxy, lower hydroxyalkyl or 1 lower alkoxyalkyl group and which can contain as a ring member an oxygen atom.

34. A method in accordance with claim 33, wherein $R^3$ is 2-(lower alkoxy)ethyl and $R^4$ is hydrogen or lower alkyl or $R^3$ and $R^4$ taken together with the nitrogen atom are 3-(lower alkoxy)-1-azetidinyl, 3-(lower alkoxy)-1-pyrrolidinyl, 2-(lower-alkoxyalkyl)-1-pyrrolidinyl, 2-(lower hydroxyalkyl)-1-pyrrolidinyl, 4-hydroxy-1-piperidinyl, 4-(lower alkoxy)-1-piperidinyl; 4-morpholinyl or 2,6-di(lower alkyl)-4-morpholinyl.

* * * * *

UNITED STATES PATENT AND TRADEMARK OFFICE
CERTIFICATE OF CORRECTION

PATENT NO. : 4,889,848

DATED : December 26, 1989

INVENTOR(S) : Ulf Fischer et al

It is certified that error appears in the above-identified patent and that said Letters Patent is hereby corrected as shown below:

ON TITLE PAGE:

[30] Foreign Application Priority Data
    November 6, 1984 [CH] Switzerland .....5304/84
    September 5, 1985 [CH] Switzerland .....3836/85

Signed and Sealed this

Third Day of December, 1991

Attest:

HARRY F. MANBECK, JR.

*Attesting Officer*      *Commissioner of Patents and Trademarks*